(12) United States Patent (10) Patent No.: US 8,207,134 B2
Sato et al. (45) Date of Patent: Jun. 26, 2012

(54) FUSED RING SPIROKETAL DERIVATIVE AND USE THEREOF AS ANTI-DIABETIC DRUG

(75) Inventors: Tsutomu Sato, Gotenba (JP); Yoshihito Ohtake, Gotenba (JP); Masahiro Nishimoto, Gotenba (JP); Takashi Emura, Gotenba (JP); Takamitsu Kobayashi, Gotenba (JP); Marina Yamaguchi, Gotenba (JP); Kyouko Takami, Gotenba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 255 days.

(21) Appl. No.: 12/375,378

(22) PCT Filed: Jul. 27, 2007

(86) PCT No.: PCT/JP2007/064802
§ 371 (c)(1),
(2), (4) Date: Mar. 22, 2010

(87) PCT Pub. No.: WO2008/013277
PCT Pub. Date: Jan. 31, 2008

(65) Prior Publication Data
US 2010/0234609 A1     Sep. 16, 2010

(30) Foreign Application Priority Data

Jul. 27, 2006   (JP) .................................. 2006-205242

(51) Int. Cl.
*A01N 43/04* (2006.01)
*A61K 31/70* (2006.01)
*C07H 1/00* (2006.01)
*C07H 3/00* (2006.01)
*C08B 37/00* (2006.01)
(52) U.S. Cl. ......................................... 514/23; 536/1.11
(58) Field of Classification Search .................. None
See application file for complete search history.

(56) References Cited

U.S. PATENT DOCUMENTS

| 7,767,651 | B2 * | 8/2010 | Kobayashi et al. ............ 514/23 |
| 2004/0053855 | A1 | 3/2004 | Fujikura et al. |
| 2005/0080022 | A1 | 4/2005 | Fujikura et al. |
| 2005/0233988 | A1 | 10/2005 | Nomura et al. |
| 2006/0217323 | A1 | 9/2006 | Patel et al. |
| 2006/0229260 | A1 | 10/2006 | Rybczynski et al. |
| 2006/0234954 | A1 | 10/2006 | Urbanski |
| 2006/0293251 | A1 | 12/2006 | Urbanski et al. |
| 2007/0275907 | A1 | 11/2007 | Chen et al. |
| 2008/0182802 | A1 | 7/2008 | Hadd et al. |
| 2009/0030006 | A1 | 1/2009 | Kobayashi et al. |

FOREIGN PATENT DOCUMENTS

| WO | 01/68660 A1 | 9/2001 |
| WO | 2005/012326 | 2/2005 |
| WO | 2006/080421 A1 | 8/2006 |

OTHER PUBLICATIONS

Stella, "Prodrugs as Therapeutics", Expert Opinion Ther. Patents (2004) 14(3), pp. 277-280.*
Adachi et al., Metabolism, vol. 49 (8), 2000, pp. 990-995.*
International Search Report in PCT/JP2007/064802.
Written Opinion (Form PCT/ISA/237) in PCT/JP2007/064802.
International Report on Patentability (Form PCT/ISA/373) in PCT/JP2007/064802.
Ahmed et al, "De novo synthesis of a galacto-papulacandin moiety via an interative dihydroxylation strategy," Tetrahedron Letters 46: 4151-4155 (2005).
Czernecki et al, "C-Glycosides. 9. Setreospecific Synthesis of C-Glycosidic Spiroketal of the Papulacandins," J. Org. Chem. 56: 6289-6292 (1991).
Danishepsky et al, "A Fully Synthetic Route to the Papulacandins. Stereo-Specific Spiroacetalization of a C-1-Arylated Methyl Glycoside," Carbohydrate Research 171:317-327 (1987).

* cited by examiner

*Primary Examiner* — Traviss C McIntosh, III
(74) *Attorney, Agent, or Firm* — Browdy and Neimark, PLLC

(57) ABSTRACT

Provided are a compound represented by Formula (I):

[Formula 1]

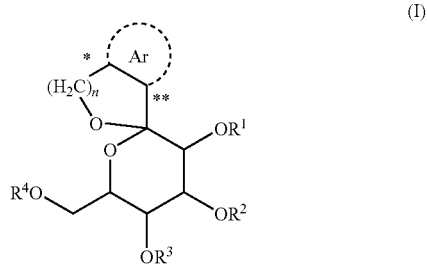

wherein $R^1$, $R^2$, $R^3$, and $R^4$ are each independently selected from a hydrogen atom, a $C_{1-6}$ alkyl group which may be substituted, a $C_{7-14}$ aralkyl group which may be substituted and —C(=O)Rx; n denotes an integer selected from 1 and 2; and ring Ar is selected from the groups represented by the following Formula (a) to (f).

[Formula 2]

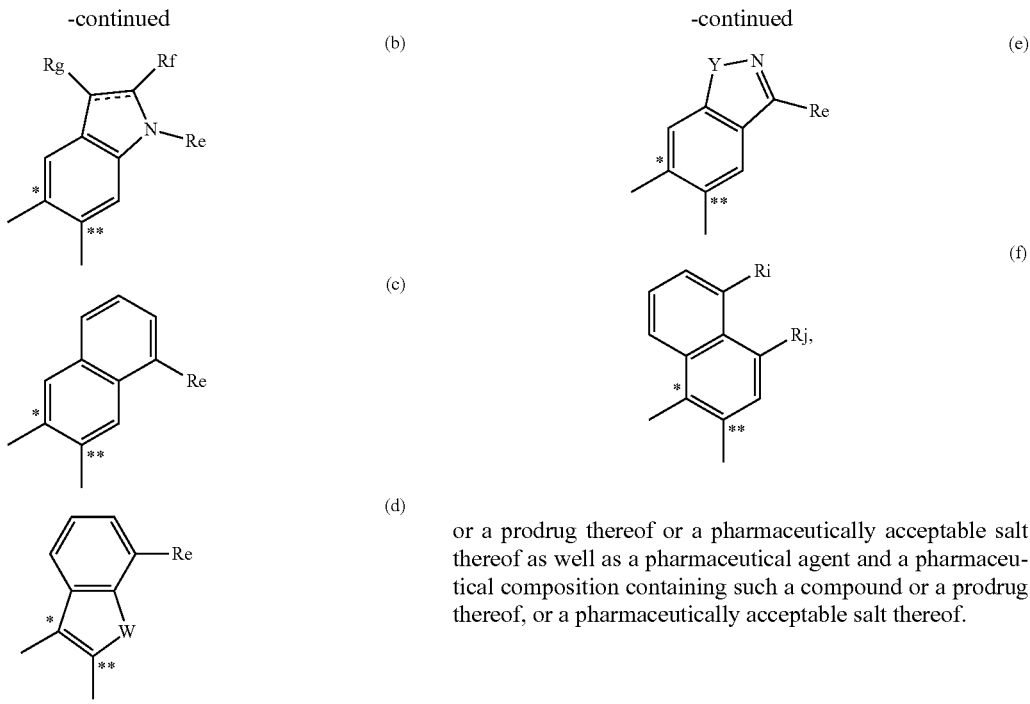
or a prodrug thereof or a pharmaceutically acceptable salt thereof as well as a pharmaceutical agent and a pharmaceutical composition containing such a compound or a prodrug thereof, or a pharmaceutically acceptable salt thereof.
16 Claims, No Drawings

US 8,207,134 B2

FUSED RING SPIROKETAL DERIVATIVE AND USE THEREOF AS ANTI-DIABETIC DRUG

TECHNICAL FIELD

The present invention relates to fused ring spiroketal derivatives useful as pharmaceutical agents, prodrugs thereof and pharmaceutically acceptable salts thereof. Particularly, the present invention relates to spiroketal derivatives which inhibit $Na^+$-glucose cotransporter 2 (SGLT2) and are thereby useful as preventive or therapeutic agents for diabetes such as insulin-dependent diabetes (Type 1 diabetes), non-insulin-dependent diabetes (Type 2 diabetes), diabetic complications and diseases caused by hyperglycaemia such as obesity, prodrugs thereof and salts thereof.

BACKGROUND ART

In late years, the number of diabetic patients has been increasing due to westernization of dietary habits, chronic lack of exercise and so on. Decrease in insulin secretion and insulin sensitivity is observed in diabetic patients, which is caused by chronic hyperglycosemia, further causes elevation of blood sugar level and leads to aggravation of symptoms. Biguanide drugs, sulfonylurea drugs, glycosidase inhibitors, insulin sensitizers, etc., have been used as therapeutic drugs for diabetes. However, side effects such as lactic acidosis as for biguanide drugs, hypoglycemia as for sulfonylurea drugs, diarrhea as for glycosidase inhibitors have been reported, and now development of therapeutic drugs for diabetes according to new action mechanism different from these drugs is eagerly demanded.

It has been reported that Phloridzin, which is a naturally-occurring glucose derivative, inhibits sodium dependent glucose cotransporter 2 (SGLT2) occurring in S1 site of the renal proximal tubule, and thereby inhibits reabsorption of excessive glucose in the kidney, promotes glucose excretion, and exhibits hypoglycemic action (refer to Non-Patent Document 1). Thereafter, up to the present, studies on the therapeutic drugs for diabetes based on SGLT2 inhibition has been extensively performed.

For example, compounds usable as inhibitors of SGLT2 are reported in JP 2000-080041 A (Patent Document 1), WO01/068,660 (Patent Document 2), WO04/007,517 (Patent Document 3), etc. However, Phloridzin and the compounds described in the above-mentioned patent applications are considered to be problematic in that when they are orally administered, they are readily hydrolyzed by glycosidase and the like present in the small intestine and the pharmacological effect thereof immediately disappears. In addition, as for Phloridzin, there has been reported that phloretin, which is the aglycone moiety thereof, strongly inhibits a sugar transporter of the facilitated diffusion type and causes bad influences such that the glucose concentration in brain decreases when phloretin is administered to a rat vein (for example, refer to Non-Patent Document 2).

Therefore, attempts to convert the compounds to prodrugs have been made for the purpose of preventing such decomposition and improving absorption efficiency. However, although it is desirable that the administered prodrugs are suitably metabolized and changed into an active compound in or in the vicinity of the target organ, there are so various metabolic enzymes in the living body and there are so many differences among individuals that stable action cannot be exhibited in many cases. Attempts to convert the glycoside bond of the compound to a carbon-carbon bond have been also made (refer to Patent Documents 4 to 21), but further improvement is demanded in the characteristics as pharmaceutical agents including activity and metabolic stability.

[Patent Document 1]
JP 2000-080041 A
[Patent Document 2]
International Publication WO01/068660
[Patent Document 3]
International Publication WO04/007517
[Patent Document 4]
US Patent Application Pub. No. 2001/041,674
[Patent Document 5]
US Patent Application Pub. No. 2002/137,903
[Patent Document 6]
International Publication WO01/027,128
[Patent Document 7]
International Publication WO02/083066
[Patent Document 8]
International Publication WO04/013118
[Patent Document 9]
International Publication WO03/099836
[Patent Document 10]
International Publication WO04/080990
[Patent Document 11]
US Patent Application Pub. No. 2005/209,166
[Patent Document 12]
International Publication WO05/085237
[Patent Document 13]
International Publication WO05/085265
[Patent Document 14]
International Publication WO05/012318
[Patent Document 15]
International Publication WO05/012326
[Patent Document 16]
US Patent Application Pub. No. 2006/063,722
[Patent Document 17]
US Patent Application Pub. No. 2006/035,841
[Patent Document 18]
US Patent Application Pub. No. 2006/074,031
[Patent Document 19]
International Publication WO06/002,912
[Patent Document 20]
International Publication WO06/008038
[Patent Document 21]
International Publication WO06/010557
[Non-Patent Document 1]
J. Clin. Invest., Vol. 93, page 397, 1994
[Non-Patent Document 2]
Stroke, Vol. 14, page 388, 1983

DISCLOSURE OF THE INVENTION

Problems to be Solved by the Invention

An object of the present invention is to provide a fused ring spiroketal derivative having preferable characteristics as a pharmaceutical agent. Particularly, an object of the present invention is to provide a fused ring spiroketal derivative having a hypoglycemic action as well as preferable characteristics as a pharmaceutical agent, such as sustained efficacy, metabolic stability or safety. Another object of the present invention is to provide a pharmaceutical composition used for the prevention or treatment of diabetes such as insulin-dependent diabetes (Type 1 diabetes) and non-insulin-dependent diabetes (Type 2 diabetes), diabetic complications and diseases caused by hyperglycaemia such as obesity.

Means for Solving the Problems

As a result of intensive investigations carried out by the present inventors to achieve the above-described objects, the present invention was completed by the discovery that fused ring spiroketal derivatives represented by Formula (I) have an excellent SGLT2 inhibitory action.

Specifically, according to one aspect of the present invention, the following compounds or prodrugs thereof, or pharmaceutically acceptable salts of said compounds or prodrugs are provided.

(1) A compound represented by Formula (I) or a prodrug thereof or a pharmaceutically acceptable salt thereof:

[Formula 1]

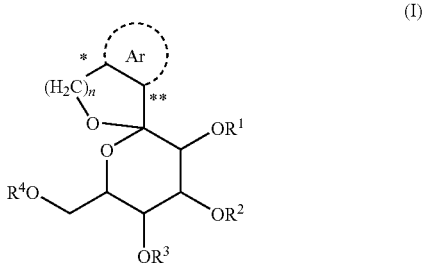

(I)

wherein $R^1$, $R^2$, $R^3$, and $R^4$ are each independently selected from a hydrogen atom, a $C_{1-6}$ alkyl group which may be substituted with one or more Ra, a $C_7$-$C_{14}$ aralkyl group which may be substituted with one or more Rb and —C(=O)Rx;

Rx is a $C_{1-6}$ alkyl group which may be substituted with one or more Ra, a aryl group which may be substituted with one or more Rb, a heteroaryl group which may be substituted with one or more Rb or a $C_{1-6}$ alkoxy group which may be substituted with one or more Ra;

n is an integer selected from 1 and 2;

Ra is each independently selected from a halogen atom, a hydroxyl group, a cyano group, a nitro group, a carboxy group, a $C_{1-6}$ alkoxy group which may be substituted with one or more Rc, an aryl group which may be substituted with one or more Rd, an aryloxy group which may be substituted with one or more Rd, a heteroaryl group which may be substituted with one or more Rd, a heteroaryloxy group which may be substituted with one or more Rd, a mercapto group, a $C_{1-6}$ alkylthio group which may be substituted with one or more Rc, a $C_{1-6}$ alkylsulfinyl group which may be substituted with one or more Rc, a $C_{1-6}$ alkylsulfonyl group which may be substituted with one or more Rc, a $C_{1-6}$ alkoxycarbonyl group which may be substituted with one or more Rc and a $C_{1-6}$ alkylcarbonyl group which may be substituted with one or more R;

Rb is each independently selected from a $C_{1-6}$ alkyl group which may be substituted with one or more Rc, a $C_{3-8}$ cycloalkyl group which may be substituted with one or more Rc, a $C_{2-6}$ alkenyl group which may be substituted with one or more Rc, a $C_{2-6}$ alkynyl group which may be substituted with one or more Rc, a $C_{7-14}$ aralkyl group which may be substituted with one or more Rd, a halogen atom, a hydroxyl group, a cyano group, a nitro group, a carboxy group, a $C_{1-6}$ alkoxy group which may be substituted with one or more Rc, an aryl group which may be substituted with one or more Rd, an aryloxy group which may be substituted with one or more Rd, a heteroaryl group which may be substituted with one or more Rd, a heteroaryloxy group which may be substituted with one or more Rd, a mercapto group, a $C_{1-6}$ alkylthio group which may be substituted with one or more Rc, a $C_{1-6}$ alkylsulfinyl group which may be substituted with one or more Rc, a $C_{1-6}$ alkylsulfonyl group which may be substituted with one or more Rc, a $C_{1-6}$ alkylcarbonyl group which may be substituted with one or more Rc, a $C_{1-6}$ alkoxycarbonyl group which may be substituted with one or more Rc, a $C_{1-3}$ alkylenedioxy group, a heterocyclyl group and a heterocyclyloxy group;

Rc is each independently selected from a halogen atom, a hydroxyl group, a cyano group, a nitro group, a carboxy group, a $C_{1-6}$ alkoxy group, an aryl group which may be substituted with one or more Rd, an aryloxy group which may be substituted with one or more Rd, a heteroaryl group which may be substituted with one or more Rd, a heteroaryloxy group which may be substituted with one or more Rd, an amino group, a $C_{1-6}$ alkylamino group and a di($C_{1-6}$ alkyl)amino group;

Rd is each independently selected from a $C_{1-6}$ alkyl group which may be substituted with one or more halogen atoms, a $C_{7-14}$ aralkyl group, a halogen atom, a hydroxyl group, a cyano group, a nitro group, an amino group, a $C_{1-6}$ alkylamino group and a di($C_{1-6}$ alkyl)amino group;

ring Ar is selected from the groups represented by the following Formula (a) to (f):

[Formula 2]

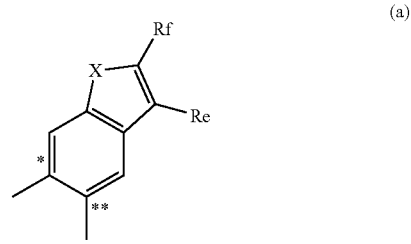

(a)

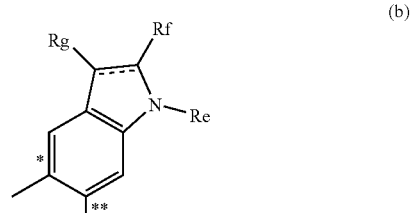

(b)

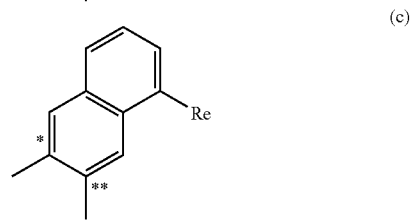

(c)

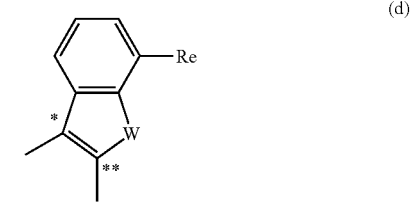

(d)

(e)

wherein X is N—Rh, O or S;

Re is a $C_{7-14}$ aralkyl group which may be substituted with one or more Rb or a $C_{5-12}$ heteroarylalkyl group which may be substituted with one or more Rb;

Rf and Rg are each independently selected from a hydrogen atom, a halogen atom and a $C_{1-6}$ alkyl group;

W is N—Rh, O or S;

Y is N—Rh, O or S;

Rh is a hydrogen atom or a $C_{1-6}$ alkyl group;

Ri and Rj are a hydrogen atom, a $C_{7-14}$ aralkyl group which may be substituted with one or more Rb or a $C_{5-12}$ heteroarylalkyl group which may be substituted with one or more Rb;

provided that, one of Ri or Rj must be a hydrogen atom; except where both Ri and Rj are a hydrogen atom; and

[Formula 3]

------ represents a single bond or a double bond, and * and ** respectively represent a bonding site, or a prodrug thereof or a pharmaceutically acceptable salt thereof.

(2) The compound according to the above (1), wherein the ring Ar is represented by the following Formula (g) to (i),

[Formula 4]

(g)

(h)

(i)

wherein Z is CH or N; and

Re is a $C_{7-14}$ aralkyl group which may be substituted with one or more Rb or a $C_{5-12}$ heteroarylalkyl group which may be substituted with one or more Rb, or a prodrug thereof or a pharmaceutically acceptable salt thereof.

(3) The compound according to either of the above (1) or (2), wherein $R^1$, $R^2$, $R^3$, and $R^4$ are each independently selected from a hydrogen atom and —C(=O)Rx, and Rx is a $C_{1-6}$ alkyl group which may be substituted with one or more Ra or a $C_{1-6}$ alkoxy group which may be substituted with one or more Ra, (4) The compound according to the above (3), wherein $R^1$, $R^2$, $R^3$, and $R^4$ are a hydrogen atom.

(5) The compound according to any of the above (1) to (4), wherein n is 1.

(6) The compound according to any of the above (1) to (4), wherein n is 2.

(7) A compound selected from:
(3'R,4'S,5S,5'S,6'R)-3-[(4-ethylphenyl)methyl]-6'-hydroxymethyl-3',4',5',6'-tetrahydro-spiro[thieno[2,3,f]isobenzofuran-5(7H),2'-[2H]pyran]-3',4',5'-triol;
(3'R,4'S,5S,5'S,6'R,7S)-1-[(4-ethylphenyl)methyl]-6'-hydroxymethyl-3',4',5',6'-tetrahydro-spiro[furo[3,4,f]indole-7(5H),2'-[2H]pyran]-3',4',5'-triol;
(1S,3'R,4'S,5'S,6'R)-8-[(4-ethylphenyl)methyl]-3,3',4,4',5',6'-hexahydro-6'-hydroxymethyl-spiro[2-oxa-9-thia-fluorene-1,2'-[2H]pyran]-3',4',5'-triol;
(3'R,4'S,5S,5'S,6'R)-6'-hydroxymethyl-3',4',5',6'-tetrahydro-3-[(4-trifluoromethylphenyl)methyl]-spiro[thieno[2,3,f]isobenzofuran-5(7H),2'-[2H]pyran]-3',4',5'-triol;
(3'R,4'S,5S,5'S,6'-hydroxymethyl-3',4',5',6'-tetrahydro-3-[(4-trifluoromethoxyphenyl)methyl]-spiro[thieno[2,3,f]isobenzofuran-5(7H),2'-[2H]pyran]-3',4',5'-triol;
(3'R,4'S,5S,5'S,6'R)-3-[(4-fluorophenyl)methyl]-6'-hydroxymethyl-3',4',5',6'-tetrahydro-spiro[thieno[2,3,f]isobenzofuran-5(7H),2'-[2H]pyran]-3',4',5'-triol;
(3'R,4'S,5S,5'S,6'R)-3-[(4-cyclopropylphenyl)methyl]-6'-hydroxymethyl-3',4',5',6'-tetrahydro-spiro[thieno[2,3,f]isobenzofuran-5(7H),2'-[2H]pyran]-3',4',5'-triol;
(3'R,4'S,5S,5'S,6'R)-6'-hydroxymethyl-3-[(4-methylphenyl)methyl]-3',4',5',6'-tetrahydro-spiro[thieno[2,3,f]isobenzofuran-5(7H),2'-[2H]pyran]-3',4',5'-triol;
(3'R,4'S,5S,5'S,6'R)-6'-hydroxymethyl-3-[(4-isopropylphenyl)methyl]-3',4',5',6'-tetrahydro-spiro[thieno[2,3,f]isobenzofuran-5(7H),2'-[2H]pyran]-3',4',5'-triol;
(3'R,4'S,5S,5'S,6'R)-3-[(5-ethylthiophen-2-yl)methyl]-6'-hydroxymethyl-3',4',5',6'-tetrahydro-spiro[thieno[2,3,f]isobenzofuran-5(7H),2'-[2H]pyran]-3',4',5'-triol;
(3'R,4'S,5S,5'S,6'R)-3-[(benzothiophen-2-yl)methyl]-6'-hydroxymethyl-3',4',5',6'-tetrahydro-spiro[thieno[2,3,f]isobenzofuran-5(7H),2'-[2H]pyran]-3',4',5'-triol;
(3'R,4'S,5S,5'S,6'R)-3-[(4-ethylphenyl)methyl]-6'-hydroxymethyl-2-methyl-3',4',5',6'-tetrahydro-spiro[thieno[2,3,f]isobenzofuran-5(7H),2'-[2H]pyran]-3',4',5'-triol;

(3'R,4'S,5S,5'S,6'R)-2-chloro-3-[(4-ethylphenyl)methyl]-6'-hydroxymethyl-3',4',5',6'-tetrahydro-spiro[thieno[2,3,f]isobenzofuran-5(7H),2'-[2H]pyran]-3',4',5'-triol;

(3'R,4'S,5S,5'S,6'R)-3-(4-ethylphenyl) -6'-hydroxymethyl-3',4',5',6'-tetrahydro-spiro[thieno[2,3,f]isobenzofuran-5(7H),2'-[2H]pyran]-3',4',5'-triol;

(3'R,4'S,5'S,6'R,7S)-6'-hydroxymethyl-3',4',5',6'-tetrahydro-1-[(4-trifluoromethoxyphenyl)methyl]-spiro[furo[3,4,f]indole-7(5H),2'-[2H]pyran]-3',4',5'-triol;

(3'R,4'S,5'S,6'R,7S)-1-[(4-fluorophenyl)methyl]-6'-hydroxymethyl-3',4',5',6'-tetrahydro-spiro[furo[3,4,f]indole-7(5H),2'-[2H]pyran]-3',4',5'-triol;

(3'R,4'S,5'S,6'R,7S)-6'-hydroxymethyl-3',4',5',6'-tetrahydro-1-[(4-trifluoromethylphenyl)methyl]-spiro[furo[3,4,f]indole-7(5H),2'-[2H]pyran]-3',4',5'-triol;

(3'R,4'S,5'S,6'R,7S)-6'-hydroxymethyl-1-[(4-methylphenyl)methyl]-3',4',5',6'-tetrahydro-spiro[furo[3,4,f]indole-7(5H),2'-[2H]pyran]-3',4',5'-triol;

(3'R,4'S,5'S,6'R,7S)-1-[(4-cyclopropylphenyl)methyl]-6'-hydroxymethyl-3',4',5',6'-tetrahydro-spiro[furo[3,4,f]indole-7(5H),2'-[2H]pyran]-3',4',5'-triol;

(3'R,4'S,5'S,6'R,7S)-6'-hydroxymethyl-1-[(4-n-propylphenyl)methyl]-3',4',5',6'-tetrahydro-spiro[furo[3,4,f]indole-7(5H),2'-[2H]pyran]-3',4',5'-triol;

(3'R,4'S,5'S,6'R,7S)-1-[(5-ethylthiophen-2-yl)methyl]-6'-hydroxymethyl-3',4',5',6'-tetrahydro-spiro[furo[3,4,f]indole-7(5H),2'-[2H]pyran]-3',4',5'-triol;

(3'R,4'S,5'S,6'R,7S)-6'-hydroxymethyl-1-[(4-isopropylphenyl)methyl]-3',4',5',6'-tetrahydro-spiro[furo[3,4,f]indole-7(5H),2'-[2H]pyran]-3',4',5'-triol;

(3'R,4'S,5'S,6'R,7S)-1-[(5-fluorobenzothiophen-2-yl)methyl]-6'=hydroxymethyl-3',4',5',6'-tetrahydro-spiro[furo[3,4,f]indole-7(5H),2'-[2H]pyran]-3',4',5'-triol;

(3'R,4'S,5'S,6'R,7S)-1-[(benzothiophen-2-yl)methyl]-6'-hydroxymethyl-3',4',5',6'-tetrahydro-spiro[furo[3,4,f]indole-7(5H),2'-[2H]pyran]-3',4',5'-triol;

(3'R,4'S,5'S,6'R,7S)-1-[2-(4-ethylphenyl)ethyl]-6'-hydroxymethyl-3',4',5',6'-tetrahydro-spiro[furo[3,4,f]indole-7(5H),2'-[2H]pyran]-3',4',5'-triol;

(3'R,4'S,5'S,6'R,7S)-3-chloro-1-[(4-ethylphenyl)methyl]-6'-hydroxymethyl-3',4',5',6'-tetrahydro-spiro[furo[3,4,f]indole-7(5H),2'-[2H]pyran]-3',4',5'-triol;

(1S,3'R,4'S,5'S,6'R)-3,3',4,4',5',6'-hexahydro-6'-hydroxymethyl-8-[(4-isopropylphenyl)methyl]-spiro[2-oxa-9-thiafluorene-1,2'-[2]pyran]-3',4',5'-triol;

(1S,3'R,4'S,5'S,6'R)-3,3',4,4',5',6'-hexahydro-6'-hydroxymethyl-8-[(4-methylphenyl)methyl]-spiro[2-oxa-9-thiafluorene-1,2'-[2]pyran]-3',4',5'-triol;

(3'R,4'S,5S',6'R)-3-[(4-ethylphenyl)methyl]-6'-hydroxymethyl-3',4',5',6'-tetrahydro-spiro[furo[3,4,f]indazole-5(1H,7H),2'-[2H]pyran]-3',4',5'-triol;

(3'R,4'S,5S,5'S,6'R)-3-[(4-ethylphenyl)methyl]-6'-hydroxymethyl-3',4',5',6'-tetrahydro-spiro[furo[3,4,f]benzoisoxazole-5(7H),2'-[2H]pyran]-3',4',5'-triol;

(3'R,4'S,5S,5'S,6'R)-3-[(4-ethylphenyl)methyl]-6'-hydroxymethyl-3',4',5',6'-tetrahydro-spiro[furo[3,4,f]benzoisothiazole-5(7H),2'-[2H]pyran]-3',4',5'-triol;

(3S,3'R,4'S,5'S,6'R)-5-[(4-ethylphenyl)methyl]-6'-hydroxymethyl-3',4',5',6'-tetrahydro-spiro[benz[g]isobenzofuro-3(1H),2'-[2H]pyran]-3',4',5'-triol; and (3'R,4'S,5'S,6'R,8S)-1-[(4-ethylphenyl)methyl]-6'-hydroxymethyl-3',4',5',6'-tetrahydro-spiro[furo[3,4 μg]naphthalene-8(6H),2'-[2H]pyran]-3',4',5'-triol;

, or a prodrug thereof or a pharmaceutically acceptable salt thereof.

(8) A compound represented by Formula (Ia):

[Formula 5]

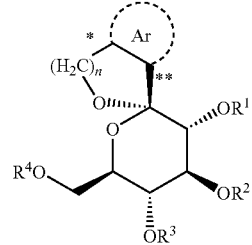

(Ia)

wherein $R^1$, $R^2$, $R^3$, and $R^4$ are each independently selected from a hydrogen atom, a $C_{1-6}$ alkyl group which may be substituted with one or more Ra, a $C_{7-14}$ aralkyl group which may be substituted with one or more Rb and —C(=O)Rx;

Rx is a $C_{1-6}$ alkyl group which may be substituted with one or more Ra, an aryl group which may be substituted with one or more Rb, a heteroaryl group which may be substituted with one or more Rb or a $C_{1-6}$ alkoxy group which may be substituted with one or more Ra;

n is an integer selected from 1 and 2;

Ra is each independently selected from a halogen atom, a hydroxyl group, a cyano group, a nitro group, a carboxy group, a $C_{1-6}$ alkoxy group which may be substituted with one or more Rc, an aryl group which may be substituted with one or more Rd, an aryloxy group which may be substituted with one or more Rd, a heteroaryl group which may be substituted with one or more Rd, a heteroaryloxy group which may be substituted with one or more Rd, a mercapto group, a $C_{1-6}$ alkylthio group which may be substituted with one or more Rc, a $C_{1-6}$ alkylsulfinyl group which may be substituted with one or more Rc, a $C_{1-6}$ alkylsulfonyl group which may be substituted with one or more Rc, a $C_{1-6}$ alkoxycarbonyl group which may be substituted with one or more Rc and a $C_{1-6}$ alkylcarbonyl group which may be substituted with one or more R;

Rb is each independently selected from a $C_{1-6}$ alkyl group which may be substituted with one or more Rc, a $C_{3-8}$ cycloalkyl group which may be substituted with one or more Rc, a $C_{2-6}$ alkenyl group which may be substituted with one or more Rc, a $C_{2-6}$ alkynyl group which may be substituted with one or more Rc, a $C_{7-14}$ aralkyl group which may be substituted with one or more Rd, a halogen atom, a hydroxyl group, a cyano group, a nitro group, a carboxy group, a $C_{1-6}$ alkoxy group which may be substituted with one or more Rc, an aryl group which may be substituted with one or more Rd, an aryloxy group which may be substituted with one or more Rd, a heteroaryl group which may be substituted with one or more Rd, a heteroaryloxy group which may be substituted with one or more Rd, a mercapto group, a $C_{1-6}$ alkylthio group which may be substituted with one or more Rc, a $C_{1-6}$ alkylsulfinyl group which may be substituted with one or more Rc, a $C_{1-6}$ alkylsulfonyl group which may be substituted with one or more Rc, a $C_{1-6}$ alkylcarbonyl group which may be substituted with one or more Rc and a $C_{1-6}$ alkoxycarbonyl group which may be substituted with one or more Rc, a $C_{1-3}$ alkylenedioxy group, a heterocyclyl group and a heterocyclyloxy group;

Rc is each independently selected from a halogen atom, a hydroxyl group, a cyano group, a nitro group, a carboxy group, a $C_{1-6}$ alkoxy group, an aryl group which may be substituted with one or more Rd, an aryloxy group which may be substituted with one or more Rd, a heteroaryl group which may be substituted with one or more Rd, a heteroaryloxy group which may be substituted with one or more Rd, an amino group, a $C_{1-6}$ alkylamino group and a di($C_{1-6}$ alkylamino group;

Rd is each independently selected from a $C_{1-6}$ alkyl group which may be substituted with one or more halogen atoms, a $C_{7-14}$ aralkyl group, a halogen atom, a hydroxyl group, a cyano group, a nitro group, an amino group, a $C_{1-6}$ alkylamino group and a di($C_{1-6}$ alkyl)amino group;

ring Ar is selected from the groups represented by the following Formula (a) to (f),

[Formula 6]

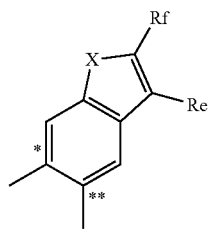
(a)

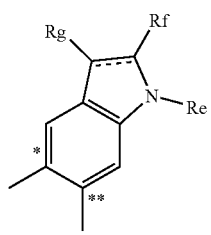
(b)

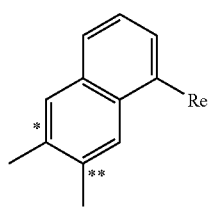
(c)

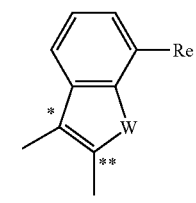
(d)

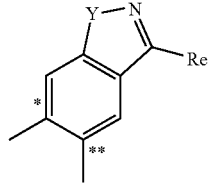
(e)

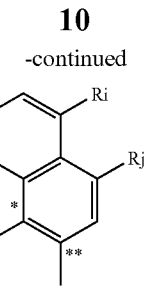
(f)

wherein X is N—Rh, O or S;
Re is a $C_{7-14}$ aralkyl group which may be substituted with one or more Rb or a $C_{5-12}$ heteroarylalkyl group which may be substituted with one or more Rb;
Rf and Rg are each independently selected from a hydrogen atom, a halogen atom and a $C_{1-6}$ alkyl group;
W is N—Rh, O or S;
Y is N—Rh, O or S;
Rh is a hydrogen atom or a $C_{1-6}$ alkyl group;
Ri and Rj are a hydrogen atom, a $C_{7-14}$ aralkyl group which may be substituted with one or more Rb or a $C_{5-12}$ heteroarylalkyl group which may be substituted with one or more Rb;
provided that, one of Ri or Rj must be a hydrogen atom; except where both Ri and Rj are a hydrogen atom; and
[Formula 7]

represents a single bond or a double bond, and * and ** respectively represent a bonding site,
or a prodrug thereof or a pharmaceutically acceptable salt thereof.

According to another aspect of the present invention, the following pharmaceutical compositions are provided.

(9) A pharmaceutical composition comprising a compound described in the above (1) to (8), or a prodrug thereof or a pharmaceutically acceptable salt thereof, which is used as a Na$^+$-glucose cotransporter inhibitor.

(10) A pharmaceutical composition comprising a compound described in the above (1) to (8), or a prodrug thereof or a pharmaceutically acceptable salt thereof, which is used for prevention or treatment of diabetes, hyperglycaemia, diabetic complications caused thereby or obesity.

(11) The pharmaceutical composition according to the above (10), wherein the diabetes is insulin-dependent diabetes (Type 1 diabetes) or non-insulin-dependent diabetes (Type 2 diabetes).

According to another aspect of the present invention, a pharmaceutical composition comprising a compound representedly Formula (I) or (Ia), or a prodrug thereof or a pharmaceutically acceptable salt thereof, which is used for prevention or treatment of diabetes (for example, insulin-dependent diabetes (Type 1 diabetes) or non-insulin-dependent diabetes (Type 2 diabetes)), hyperglycemia, diabetic complications caused thereby, or obesity is provided.

According to still another aspect of the present invention, there is provided a method for preventing or treating diabetes (for example, insulin-dependent diabetes (Type 1 diabetes) or non-insulin-dependent diabetes (Type 2 diabetes)), hyperglycemia, or diabetic complications caused thereby, or obesity comprising administering to a patient of an effective therapeutic dose of the compound represented by Formula (I) or (Ia), or a prodrug thereof or pharmaceutically acceptable salt thereof.

In the above-described Formula (I) or (Ia), examples of the groups represented by $R^1$, $R^2$, $R^3$, and $R^4$ include a hydrogen atom, a $C_{1-6}$ alkyl group, a $C_{1-6}$ alkoxy $C_{1-6}$ alkyl group, a $C_{7-14}$ aralkyl group, a $C_{1-6}$ alkylcarbonyl group, a $C_{7-14}$ aralkylcarbonyl group, a $C_{1-6}$ alkoxycarbonyl group and a $C_{7-14}$ aralkyloxycarbonyl group. These groups may also be substituted with one or more substituents each independently selected from a halogen atom, a hydroxyl group, a alkoxy group, a $C_{1-6}$ alkylcarbonyl group, a carboxy group, an amino group and a substituted amino group. A hydrogen atom is especially preferred as $R^1$, $R^2$, $R^3$, and $R^4$.

In the above-described Formula (I) and (Ia), the ring Ar is selected from the groups represented by the following Formula (a) to (f).

[Formula 8]

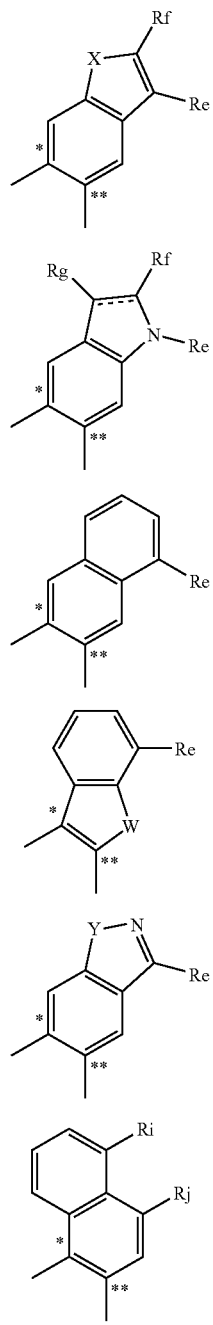

Preferred groups represented by Formula (a) include, for example, 3-[(4-ethylphenyl)methyl]benzothiophenyl group, 3-[(4-methylphenyl)methyl]benzothiophenyl group, 3-[(4-methoxyphenyl)methyl]benzothiophenyl group, 3-[(4-(methylthio)phenyl)methyl]benzothiophenyl group, 3-[(4-isopropylphenyl)methyl]benzothiophenyl group, 3-[(4-ethylphenyl)methyl]-2-methylbenzothiophenyl group, 2-chloro-3-[(4-ethylphenyl)methyl]benzothiophenyl group, 3-[(4-ethylphenyl)methyl]benzofuranyl group, 3-[(4-methylphenyl)methyl]benzofuranyl group, 3-[(4-methoxyphenyl)methyl]benzofuranyl group, 3-[(4-(methylthio)phenyl)methyl]benzofuranyl group, 3-[(4-isopropylphenyl)methyl]benzofuranyl group, 3-[(4-ethylphenyl)methyl]-2-methylbenzofuranyl group, 2-chloro-3-[(4-ethylphenyl)methyl]benzofuranyl group, 3-[(4-ethylphenyl)methyl]indolyl group, 3-[(4-methylphenyl)methyl]indolyl group, 3-[(4-methoxyphenyl)methyl]indolyl group, 3-[(4-(methylthio)phenyl)methyl]indolyl group, 3-[(4-isopropylphenyl)methyl]indolyl group, 3-[(4-ethylphenyl)methyl]-2-methylindolyl group, 2-chloro-3-[(4-ethylphenyl)methyl]indolyl group, 3-[(4-ethylphenyl)methyl]-1-methylindolyl group, 3-[(4-methylphenyl)methyl]-1-methylindolyl group, 3-[(4-methoxyphenyl)methyl]-1-methylindolyl group, 3-[(4-(methylthio)phenyl)methyl]-1-methylindolyl group, 3-[(4-isopropylphenyl)methyl]-1-methylindolyl group, 1,2-dimethyl-3-[(4-ethylphenyl)methyl]-indolyl group and 2-chloro-3-[(4-ethylphenyl)methyl]-1-methylindolyl group. Especially preferable compounds are those wherein X is S. Specifically, 3-[(4-ethylphenyl)methyl]benzothiophenyl group is preferred. Further, it is preferred that Rf is independently H, $CH_3$ or Cl. In addition, Re is preferably 4-ethylphenylmethyl group.

Preferred groups represented by Formula (b) include, for example, 1-[(4-ethylphenyl)methyl]indolyl group, 1-[(4-methylphenyl)methyl]indolyl group, a 1-[(4-methoxyphenyl)methyl]indolyl group, 1-[(4-(methylthio)phenyl)methyl]indolyl group, 1-[(4-isopropylphenyl)methyl]indolyl group, 1-[(4-ethylphenyl)methyl]indolinyl group, 1-[(4-methylphenyl)methyl]indolinyl group, 1-[(4-methoxyphenyl)methyl]indolinyl group, 1-[(4-(methylthio)phenyl)methyl]indolinyl group, 1-[(4-isopropylphenyl)methyl]indolinyl group, 1-[(4-ethylphenyl)methyl]-2-methylindolyl group, 1-[(4-methylphenyl)methyl]-2-methylindolyl group, 1-[(4-methoxyphenyl)methyl]-2-methylindolyl group, 1-[(4-(methylthio)phenyl)methyl]-2-methylindolyl group, 1-[(4-isopropylphenyl)methyl]-2-methylindolyl group, 2-chloro-1-[(4-ethylphenyl)methyl]indolyl group, 2-chloro-1-[(4-methylphenyl)methyl]indolyl group, 2-chloro-1-[(4-methoxyphenyl)methyl]indolyl group, 2-chloro-1-[(4-(methylthio)phenyl)methyl]indolyl group and 2-chloro-1-[(4-isopropylphenyl)methyl]indolyl group. Specifically, 1-[(4-ethylphenyl)methyl]indolyl group is preferred. It is especially preferable for Rf and Rg to be each independently H, $CH_3$ or Cl. In addition, Re is preferably 4-ethylphenylmethyl group, and

[Formula 9]

────── is preferably a double bond.

Preferred groups represented by Formula (c) include, for example, 8-[(4-ethylphenyl)methyl]naphthyl group, 5-[(4-methylphenyl)methyl]naphthyl group, 8-[(4-methoxyphenyl)methyl]naphthyl group, 8-[(4-(methylthio)phenyl)methyl]naphthyl group and 8-[(4-isopropylphenyl)methyl]naphthyl group. Specifically, 8-[(4-ethylphenyl)methyl]naphthyl group is preferred.

Preferred groups represented by Formula (d) include, for example, 7-[(4-ethylphenyl)methyl]benzothiophenyl group, 7-[(4-methylphenyl)methyl]benzothiophenyl group, 7-[(4-methoxyphenyl)methyl]benzothiophenyl group, 7-[(4-(methylthio)phenyl)methyl]benzothiophenyl group, 7-[(4-isopropylphenyl)methyl]benzothiophenyl group, 7-[(4-ethylphenyl)methyl]-2-methylbenzothiophenyl group, 2-chloro-7-[(4-ethylphenyl)methyl]benzothiophenyl group, 7-[(4-ethylphenyl)methyl]benzofuranyl group, 7-[(4-methylphenyl)methyl]benzofuranyl group, 7-[(4-methoxyphenyl)methyl]benzofuranyl group, 7-[(4-(methylthio)phenyl)methyl]benzofuranyl group, 7-[(4-isopropylphenyl)methyl]benzofuranyl group, 7-[(4-ethylphenyl)methyl]-2-methylbenzofuranyl group, 2-chloro-7-[(4-ethylphenyl)methyl]benzofuranyl group, 7-[(4-ethylphenyl)methyl]indolyl group, 7-[(4-methylphenyl)methyl]indolyl group, 7-[(4-methoxyphenyl)methyl]indolyl group, 7-[(4-(methylthio)phenyl)methyl]indolyl group, 7-[(4-isopropylphenyl)methyl]indolyl group, 7-[(4-ethylphenyl)methyl]-1-methylindolyl group, 7-[(4-methylphenyl)methyl]-1-methylindolyl group, 7-[(4-methoxyphenyl)methyl]-1-methylindolyl group, 7-[(4-(methylthio)phenyl)methyl]-1-methylindolyl group, 7-[(4-isopropylphenyl)methyl]-1-methylindolyl group, 1,2-dimethyl-7-[(4-ethylphenyl)methyl]indolyl group and 2-chloro-7-[(4-ethylphenyl)methyl]-1-methylindolyl group. Especially preferable compounds are those wherein W is S. Specifically, 7-[(4-ethylphenyl)methyl]benzothiophenyl group is preferred. In addition, Re is preferably 4-ethylphenylmethyl group.

Preferred groups represented by Formula (e) include, for example, 3-[(4-ethylphenyl)methyl]benzoisoxazolyl group, 3-[(4-methylphenyl)methyl]benzoisoxazolyl group, 3-[(4-methoxyphenyl)methyl]benzoisoxazolyl group, 3-[(4-(methylthio)phenyl)methyl]benzoisoxazolyl group, 3-[(4-isopropylphenyl)methyl]benzoisoxazolyl group, 3-[(4-ethylphenyl)methyl]benzoisothiazolyl group, 3-[(4-methylphenyl)methyl]benzoisothiazolyl group, 3-[(4-methoxyphenyl)methyl]benzoisothiazolyl group, 3-[(4-(methylthio)phenyl)methyl]benzoisothiazolyl group, 3-[(4-isopropylphenyl)methyl]benzoisothiazolyl group, 3-[(4-ethylphenyl)methyl]indazolyl group, 3-[(4-methylphenyl)methyl]indazolyl group, 3-[(4-methoxyphenyl)methyl]indazolyl group, 3-[(4-(methylthio)phenyl)methyl]indazolyl group, 3-[(4-isopropylphenyl)methyl]indazolyl group. Specifically, 3-[(4-ethylphenyl)methyl]benzoisoxazolyl group, 3-[(4-ethylphenyl)methyl]benzoisothiazolyl group or 3-[(4-ethylphenyl)methyl]indazolyl group is preferred.

Preferred groups represented by Formula (f) include, for example, 5-[(4-ethylphenyl)methyl]naphthyl group, 5-[(4-methylphenyl)methyl]naphthyl group, 5-[(4-methoxyphenyl)methyl]naphthyl group, 5-[(4-(methylthio)phenyl)methyl]naphthyl group, 5-[(4-isopropylphenyl)methyl]naphthyl group, 4-[(4-ethylphenyl)methyl]naphthyl group, 4-[(4-methylphenyl)methyl]naphthyl group, 4-[(4-methoxyphenyl)methyl]naphthyl group, 4-[(4-(methylthio)phenyl)methyl]naphthyl group and 4-[(4-isopropylphenyl)methyl]naphthyl group. Specifically, 5-[(4-ethylphenyl)methyl]naphthyl group or 4-[(4-ethylphenyl)methyl]naphthyl group is preferred.

The term "$C_{1-6}$ alkyl group" in the present specification means a linear or branched alkyl group having 1 to 6 carbon atoms. Examples include methyl, ethyl, n-propyl, 1-propyl, n-butyl, s-butyl, i-butyl, t-butyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl, 2-ethylbutyl and the like. Examples of a preferred $C_{1-6}$ alkyl group include a linear or branched alkyl group having 1 to 3 carbon atoms. Especially preferred are methyl and ethyl.

The term "$C_{2-6}$ alkenyl group" in the present specification means a linear or branched alkenyl group having 2 to 6 carbon atoms. Examples include ethenyl (vinyl), 1-propenyl, 2-propenyl (allyl), propen-2-yl, 3-butenyl (homoallyl) and the like.

The term "$C_{2-6}$ alkynyl group" in the present specification means a linear or branched alkynyl group having 2 to 6 carbon atoms. Examples include ethynyl, 1-propynyl, 2-propynyl, 1-butynyl, 2-butynyl, 3-butynyl and the like.

The term "$C_{3-8}$ cycloalkyl group" in the present specification means a cyclic alkyl group having 3 to 8 carbon atoms. Examples include cyclopropyl, cyclobutyl, cyclopentyl, cyclohexyl, cycloheptyl, cyclooctyl and the like.

The term "$C_{1-6}$ alkoxy group" in the present specification means an alkyloxy group having as an alkyl moiety a linear or branched alkyl group having 1 to 6 carbon atoms. Examples include methoxy, ethoxy, n-propoxy, I-propoxy, n-butoxy, s-butoxy, i-butoxy, t-butoxy, n-pentoxy, 3-methylbutoxy, 2-methylbutoxy, 1-methylbutoxy, 1-ethylpropoxy, n-hexyloxy, 4-methylpentoxy, 3-methylpentoxy, 2-methylpentoxy, 1-methylpentoxy, 3-ethylbutoxy and the like.

The term "$C_{7-14}$ aralkyl group" in the present specification means an arylalkyl group which includes an aryl group and has 7 to 14 carbon atoms. Examples include benzyl, 1-phenethyl, 2-phenethyl, 1-naphthylmethyl, 2-naphthylmethyl and the like.

The term "$C_{5-12}$ heteroarylalkyl group" in the present specification means an arylalkyl group which includes one or more heteroatoms independently selected from an oxygen atom, a nitrogen atom and a sulfur atom, and which has 5 to 12 carbon atoms. Examples include 2-thienylmethyl group, 3-thienylmethyl group, 2-furylmethyl group, 2-benzothiophenylmethyl group, 2-benzofuranylmethyl group, 2-indolylmethyl group, 5-benzothiophenylmethyl group, 6-benzothiophenylmethyl group, 3-quinolinylmethyl group, 3-isoquinolinylmethyl group, 6-quinolinylmethyl group, 7-quinolinylmethyl group, 6-isoquinolinylmethyl group, 7-isoquinolinylmethyl group and the like.

The term "aryl group" in the present specification means an aryl group having an aromatic hydrocarbon ring having 6 to 10 carbon atoms. Examples include phenyl, 1-naphthyl, 2-naphthyl and the like.

The term "heteroaryl group" in the present specification means a 5- to 10-membered aromatic heterocycle which includes one or more heteroatoms independently selected from an oxygen atom, a nitrogen atom and a sulfur atom. Examples include furyl, thienyl, pyrrolyl, imidazolyl, pyrazolyl, oxazolyl, isoxazolyl, thiazolyl, isothiazolyl, oxadiazolyl, thiadiazolyl, triazolyl, tetrazolyl, pyridinyl, pyrimidinyl, pyrazinyl, pyridazinyl, benzothiophenyl, benzofuranyl, indolyl, quinolinyl, isoquinolinyl and the like. Preferred heteroaryl groups are a thienyl group and a benzothiophenyl group.

The term "aryloxy group" in the present specification means an aryloxy group having as an aryl moiety the above-defined aromatic hydrocarbon group having 6 to 10 carbon atoms. Examples include phenoxy, 1-naphthoxy, 2-naphthoxy and the like.

The term "heteroaryloxy group" in the present specification means an heteroaryloxy group having as a heteroaryl moiety the above-defined 5- to 10-membered aromatic heterocycle which includes one or more heteroatoms independently selected from an oxygen atom, a nitrogen atom and a sulfur atom. Examples include furyloxy, thienyloxy, pyrrolyloxy, imidazolyloxy, pyrazolyloxy, oxazolyloxy, isoxazolyloxy, thiazolyloxy, isothiazolyloxy, oxadiazolyloxy, thiadiazolyloxy, triazolyloxy, tetrazolyloxy, pyridinyloxy, pyrimidinyloxy, pyrazinyloxy, pyridazinyloxy, indolyloxy, quinolinyloxy, isoquinolinyloxy and the like. A preferred heteroaryloxy group is a 5- or 6-membered heteroaryloxy group.

The term "$C_{1-6}$ alkylamino group" in the present specification means an alkylamino group having as an alkyl moiety a linear or branched alkyl group having 1 to 6 carbon atoms. Examples include methylamino, ethylamino, n-propylamino, i-propylamino, n-butylamino, s-butylamino, I-butylamino, t-butylamino, n-pentylamino, 3-methylbutylamino, 2-methylbutylamino, 1-methylbutylamino, 1-ethylpropylamino, n-hexylamino, 4-methylpentylamino, 3-methylpentylamino, 2-methylpentylamino, 1-methylpentylamino, 3-ethylbutylamino, 2-ethylbutylamino and the like.

The term "di($C_{1-6}$ alkyl)amino group" in the present specification means a dialkylamino group having as two alkyl moieties linear or branched alkyl groups each having 1 to 6 carbon atoms. The two alkyl moieties may be the same or different. Examples of the "di($C_{1-6}$ alkyl)amino group" may include dimethylamino, diethylamino, di-n-propylamino, di-i-propylamino, di-n-butylamino, methyl-n-butylamino, methyl-s-butylamino, methyl-i-butylamino, methyl-t-butylamino, ethyl-n-butylamino, ethyl-s-butylamino, ethyl-i-butylamino, ethyl-t-butylamino and the like.

The term "$C_{1-6}$ alkylthio group" in the present specification means an alkylthio group having as an alkyl moiety a linear or branched alkyl group having 1 to 6 carbon atoms. Examples include methylthio, ethylthio, n-propylthio, i-propylthio, n-butylthio, s-butylthio, i-butylthio, t-butylthio, n-pentylthio, 3-methylbutylthio, 2-methylbutylthio, 1-methylbutylthio, 1-ethylpropylthio, n-hexylthio, 4-methylpentylthio, 3-methylpentylthio, 2-methylpentylthio, 1-methylpentylthio, 3-ethylbutylthio, 2-ethylbutylthio and the like.

The term "$C_{1-6}$ alkylsulfinyl group" in the present specification means an alkylsulfinyl group (—SO—$C_{1-6}$ alkyl) having as an alkyl moiety a linear or branched alkyl group having 1 to 6 carbon atoms. Examples include methylsulfinyl, ethylsulfinyl, n-propylsulfinyl, i-propylsulfinyl, n-butylsulfinyl, s-butylsulfinyl, i-butylsulfinyl, t-butylsulfinyl, n-pentylsulfinyl, 3-methylbutylsulfinyl, 2-methylbutylsulfinyl, 1-methylbutylsulfinyl, 1-ethylpropylsulfinyl, n-hexylsulfinyl, 4-methylpentylsulfinyl, 3-methylpentylsulfinyl, 2-methylpentylsulfinyl, 1-methylpentylsulfinyl, 3-ethylbutylsulfinyl, 2-ethylbutylsulfinyl and the like.

The term "$C_{1-6}$ alkylsulfonyl group" in the present specification means an alkylsulfonyl group having as an alkyl moiety a linear or branched alkyl group having 1 to 6 carbon atoms. Examples include methylsulfonyl, ethylsulfonyl, n-propylsulfonyl, i-propylsulfonyl, n-butylsulfonyl, s-butylsulfonyl, i-butylsulfonyl, t-butylsulfonyl, n-pentylsulfonyl, 3-methylbutylsulfonyl, 2-methylbutylsulfonyl, 1-methylbutylsulfonyl, 1-ethylpropylsulfonyl, n-hexylsulfonyl, 4-methylpentylsulfonyl, 3-methylpentylsulfonyl, 2-methylpentylsulfonyl, 1-methylpentylsulfonyl, 3-ethylbutylsulfonyl, 2-ethylbutylsulfonyl and the like.

Examples of the term "—C(=O)—Rx" in the present specification include a $C_{1-6}$ alkylcarbonyl group, a $C_{7-14}$ aralkylcarbonyl group, a $C_{1-6}$ alkoxycarbonyl group, a $C_{7-14}$ aralkyloxycarbonyl group and the like.

The term "$C_{1-6}$ alkoxycarbonyl group" in the present specification means a formula —C(=O)—O—$C_{1-6}$ alkyl group. Examples include methoxycarbonyl group, ethoxycarbonyl group, tert-butoxycarbonyl group, an isobutyloxycarbonyl group and the like. A preferred example of the $C_{1-6}$ alkoxycarbonyl group is methoxycarbonyl group.

The term "$C_{1-6}$ alkylcarbonyl group" in the present specification means a formula —(C=O)—$C_{1-6}$ alkyl group. Examples include acetyl group, propionyl group, butyryl group, isobutyryl group, pivaloyl group and the like. A preferred example of the $C_{1-6}$ alkylcarbonyl group is acetyl group.

The term "$C_{1-6}$ alkyloxy $C_{1-6}$ alkyl group" in the present specification means a formula —$C_{1-6}$ alkyl-O—$C_{1-6}$ alkyl group. Examples include methoxymethyl group, ethoxymethyl group, 1-ethoxymethyl group and the like. A preferred example of the $C_{1-6}$ alkyloxy $C_{1-6}$ alkyl group is methoxymethyl group.

Examples of the "$C_{7-14}$ aralkylcarbonyl group" in the present specification include benzylcarbonyl group, naphthylmethylcarbonyl group and the like. A preferred example of the $C_{7-14}$ aralkylcarbonyl group is benzylcarbonyl group.

Examples of the "$C_{7-14}$ aralkyloxycarbonyl group" in the present specification include benzyloxycarbonyl group, naphthylmethyloxycarbonyl group and the like. A preferred example of the $C_{7-14}$ aralkyloxycarbonyl group is benzyloxycarbonyl group.

Examples of the halogen atom in the present specification include a fluorine atom, a chlorine atom, a bromine atom, an iodine atom and the like.

The "$C_{1-3}$ alkylenedioxy group" in the present specification is a divalent group represented by the formula —O—($C_{1-3}$ alkylene)-O—. Examples thereof include methylenedioxy group, ethylenedioxy group, dimethylmethylenedioxy group and the like.

The term "heterocyclyl group" in the present specification means a 4- to 7-membered heterocycle group which may be completely saturated or partially or completely unsaturated and which includes one or more heteroatoms independently selected from an oxygen atom, a nitrogen atom and a sulfur atom. Examples include azetidinyl, pyrrolidinyl, piperidinyl, piperadinyl, pyrrolyl, imidazolyl, imidazolinyl, pyrazolyl, pyrazolinyl, oxazolinyl, morpholinyl, thiomorpholinyl, pyridinyl, pyrazinyl, pyrimidinyl, pyridazinyl, hexamethyleneimino, furyl, tetrahydrofuryl, thienyl, tetrahydrothienyl, dioxolanyl, oxathiolanyl, dioxanyl and the like. The substitution site of the heterocycle group is not especially limited so long as a carbon atom or a nitrogen atom which can be substituted thereon.

The term "heterocyclyloxy group" in the present specification means an oxy group linked with a 4- to 7-membered heterocycle which may be completely saturated or partially or completely unsaturated and which includes one or more heteroatoms independently selected from an oxygen atom, a nitrogen atom and a sulfur atom. Examples include azetidinyloxy, pyrrolidinyloxy, piperidinyloxy, piperadinyloxy, pyrrolyloxy, imidazolyloxy, imidazolinyloxy, pyrazolyloxy, pyrazolinyloxy, oxazolinyloxy, morpholinyloxy, thiomorpholinyloxy, pyridinyloxy, pyrazinyloxy, pyrimidinyloxy, pyridazinyloxy, hexamethyleneiminoxy, furyloxy, tetrahydrofuryloxy, thienyloxy, tetrahydrothienyloxy, dioxolanyloxy, oxathiolanyloxy, dioxanyloxy and the like. The substitution site of the heterocycle group is not especially limited so long as a carbon atom or a nitrogen atom which can be substituted thereon.

In addition, the compound according to the present invention may include mixtures of various stereoisomers such as tautomers and enantiomers or an isolated substance.

The compounds of the present invention may form acid addition salts. The compounds may form salts with a base depending on the kind of the substituent. Such salts specifically include acid addition salts with mineral acids such as hydrochloric acid, hydrobromic acid, hydroiodic acid, sulfuric acid, nitric acid, phosphoric acid; organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid; and acidic amino acids such as aspartic acid and glutamic acid. The salts formed with bases include salts with inorganic bases such as sodium, potassium, magnesium, calcium and aluminum; salts with organic bases such as methylamine, ethylamine, ethanolamine; salts with basic amino acids such as lysin, ornithine and ammonium salts.

Furthermore, hydrates, pharmaceutically acceptable various solvates and crystal polymorphs are included in the compounds of the present invention.

It is noted that the compound according to the present invention is not limited to the compounds described in the following examples. The present invention includes all spiroketal derivatives represented by the above-described Formula (I) and pharmaceutically acceptable salts thereof.

The present invention also includes so-called prodrugs which are compounds metabolized in the living body and converted into the compounds of the above Formula (I) and pharmaceutically acceptable salts thereof. Groups to form prodrugs of the compounds of the present invention include groups described in Prog. Med. Vol. 5, pages 2157-2161 (1985) and groups described in "Iyakuhin no Kaihatsu" ("Development of medicinal drugs"), Vol. 7 (molecular design), pages 163-198, Hirokawa Shoten published in 1990.

The compounds of the present invention can be produced by applying various kinds of a publicly known synthesis method in accordance with characteristics based on the basic structure or the kind of the substituents. Depending on the kind of functional groups, it may be preferable in terms of production technology to protect a functional group with a suitable protecting group at the stage of raw materials or intermediates, and desired compounds can be obtained by removing the protecting group in the later steps. Examples of the functional groups needed to be protected in the production process include a hydroxyl group and a carboxy group and examples of the protecting groups thereof include the protecting groups described in Greene and Wuts, "Protective Groups in Organic Synthesis", second edition. The protecting group to be used and reaction conditions at the time of introducing and removing the protecting group can be appropriately selected based on the conventional technology such as those described in the above-mentioned documents.

The compounds of the present invention have inhibitory activity on sodium dependent glucose cotransporter 2 (SGLT2) involved in glucose reabsorption in the kidney (J. Clin. Invest., Vol. 93, page 397, 1994). Inhibition of SGLT2 suppresses reabsorption of sugar, causes excretion of excessive sugar to outside the body and thereby leads to therapeutic effect on the diabetes and to an effect of improving insulin resistance by correcting hyperglycosemia without giving load on β cells of the pancreas.

Therefore, according to one aspect of the present invention, there is provided a pharmaceutical agent to prevent or treat diseases or conditions which can be improved by inhibiting the activity of SGLT2, for example, diabetes, diabetes-related diseases and diabetic complications are provided.

Here, the "diabetes" includes Type 1 diabetes, Type 2 diabetes, the other types of diabetes by specific causes. The "diabetes-related diseases" includes, for example, obesity, hyperinsulinemia, abnormality of glucose metabolism, hyperlipidemia, hypercholesterolemia, hypertriglyceridemia, lipidosis, hypertension, congestive heart failure, edema, hyperuricemia and gout.

The "diabetic complications" include both acute and chronic complications. Examples of "acute complications" include hyperglycemia (ketoacidosis, etc.), infectious diseases (infection in the skin, soft tissue, biliary system, respiratory system, urinary tract, etc.) and examples of "chronic complication" include microangiopathy (nephropathy, retinopathy), arteriosclerosis (atherosclerosis, myocardial infarction, cerebral infarction, lower limbs arterial occlusion, etc.), neuropathy (in sensory nerve, motor nerves, autonomous nerve, etc.), foot gangrene. Major diabetic complications include diabetic retinopathy, diabetic nephropathy and diabetic neuropathy.

The compounds of the present invention can be used together with therapeutic drugs for diabetes, or diabetic complications, having different action mechanism other than SGLT2 activity inhibitor, antihyperlipemic drugs, or antihypertensive drug, etc. Additive effect can be expected by combining the compounds of the present invention with the other drugs as compared with the effect obtained by singly using the respective drugs for the above-mentioned diseases.

Examples of the "therapeutic drug for diabetes or diabetic complications" which can be used together include insulin sensitivity enhancing drugs (PPARγ agonist, PPARα/γ agonist, PPARδ agonist, PPARα/γ/δ agonist), glycosidase inhibitors, biguanide drugs, insulin secretion enhancers, insulin formulation, glucagon receptor antagonists, insulin receptor kinase enhancers, tripeptidyl peptidase II inhibitors, dipeptidyl peptidase IV inhibitors, protein tyrosine phosphatase-1B inhibitors, glycogen phosphorylase inhibitors, glucose-6-phosphatase inhibitors, gluconeogenesis inhibitors, fructose bisphosphatase inhibitors, pyruvic acid dehydrogenase inhibitors, glucokinase activators, D-chiro-inositol, glycogen synthetase kinase-3 inhibitors, glucagons-like peptide-1, glucagons-like peptide-1 analogues, glucagons-like peptide-1 agonists, amylin, amylin analogues, amylin agonists, glucocorticoid receptor antagonists, 11β-hydroxysteroid dehydrogenase inhibitors, aldose reductase inhibitors, protein kinase C inhibitors, γ-aminobutyric acid receptor antagonists, sodium channel antagonists, transcription factor NF-κB inhibitors, IKKβ inhibitors, lipid peroxidase inhibitors, N-acetylated-α-linked-acid-dipeptidase inhibitors, insulin-like growth factor-I, platelet-derived growth factors (PDGF), platelet-derived growth factor (PDGF) analogues, epidermal growth factors (EGF), nerve growth factors, carnitine derivatives, uridine, 5-hydroxy-1-methyl hydantoin, EGB-761, bimoclomol, sulodexide, Y-128 and TAR-428.

The "therapeutic drug for diabetes or diabetic complications" can be exemplified as follows.

Metoformine hydrochloride and fenformine are included as "biguanide drugs".

Among insulin secretion enhancers, examples of sulphonylurea drugs include glyburide (glibenclamide), glipizide, gliclazide, chlorpropamide and examples of non-sulphonylurea drugs include nateglinide, repaglinide and mitiglinide.

The "insulin formulation" include genetic recombinant human insulin and animal origin insulin. They are classified into three types by duration of action, and include immediate-acting type (human insulin, human neutral insulin), intermediate-acting type (insulin-human isofen insulin aqueous suspension, human neutral insulin-human isofen insulin aqueous suspension, human insulin zinc aqueous suspension, insulin zinc aqueous suspension) and sustained-acting type (huma crystalline insulin zinc suspension).

The "glycosidase inhibitors" include acarbose, voglibose and miglitol.

Among "insulin sensitivity enhancing drugs", PPARγ agonists include troglitazone, pioglitazone, rosiglitazone, PPARα/γ dual agonists include MK-767 (KRP-297), Tesaglitazar, LM4156, LY510929, DRF-4823, TY-51501, and PPARδ agonists include GW-501516.

The "tripeptidyl peptidase II inhibitors" include UCL-139.

The "dipeptidyl peptidase IV inhibitors" include NVP-DPP728A, LAF-237, MK-0431, P32/98 and TSL-225.

The "aldose reductase inhibitors" include ascorbyl gamolenate, tolrestat, epalrestat, fidarestat, sorbynyl, ponalrestat, risarestat and zenarestat.

The "γ-aminobutyric acid receptor antagonists" include topiramate.

The "sodium channel antagonists" include mexiletine hydrochloride.

The "transcription factor NF-κB inhibitors" include dexlipotam.

The "lipid peroxidase inhibitors" include tirilazad mesylate.

The "N-acetylated-α-linked-acid-dipeptidase inhibitors" include GPI-5693.

The "carnitine derivatives" include carnitine, levacecamine hydrochloride.

The "antihyperlipemic drugs and antihypertensive drugs" which can be used together include, for example, hydroxymethylglutaryl coenzyme A reductase inhibitors, fibrate compounds, $β_3$-adrenaline receptor agonists, AMPK activators, acyl coenzyme A:cholesterol transacylase inhibitors, probcol, thyroid hormone receptor agonists, cholesterol absorption inhibitors, lipase inhibitors, microsome triglyceride transfer protein inhibitors, lipoxygenase inhibitors, carnitine palmitoyltransferase inhibitors, squalene synthetase inhibitors, low-density lipoprotein receptor enhancers, nicotine acid derivatives, bile acid adsorbing drugs, sodium conjugate bile acid transporter inhibitors, cholesterol ester transportation protein inhibitors, angiotensin converting enzyme inhibitors, angiotensin II receptor antagonists, endothelin converting enzyme inhibitors, endothelin receptor antagonists, diuretic drugs, calcium antagonists, vasodilatory hypotensive agents, sympatholytic drugs, central hypotensive agents, $α_2$-adrenaline receptor agonists, antiplatelets, uric acid generation inhibitors, uric acid excretion enhancers, urine alkalizer, anorectic drugs, ACE inhibitors, adiponectin receptor agonists, GPR40 agonists, GPR40 antagonists.

The therapeutic drugs for hyperlipemia and antihypertensive drugs can be exemplified as follows.

The "hydroxymethylglutaryl coenzyme A reductase inhibitors" include fluvastatin, lovastatin, pravastatin, cerivastatin and pitavastatin.

The "fibrate compounds" include bezafibrate, beclobrate and binifibrate.

The "squalene synthetase inhibitors" include TAK-475, α-phosphonosulphonate derivatives (specification of U.S. Pat. No. 5,712,396).

The "acyl coenzyme A: cholesterol transacylase inhibitors" include CI-1011, NTE-122, FCE-27677, RP-73163, MCC-147 and DPU-129.

The "low-density lipoprotein receptor enhancers" include MD-700 and LY-295427.

The "microsome triglyceride transfer protein inhibitors" (MTP inhibitors) include compounds described in the specifications of U.S. Pat. Nos. 5,739,135, 5,712,279 and 5,760,246.

The "anorectic drugs" include adrenaline-noradrenalin agonists (mazindol, ephedrine, etc.), serotonin agonists (selective serotonin reuptake inhibitors, for example, fluvoxamine, etc.), adrenaline-serotonin agonists (sibutramine, etc.), melanocortin-4 receptor (MC4R) agonists, α-melanocyte stimulating hormones (α-MCH), leptin, cocaine- and amphetamine-regulated transcript (CART).

The "thyroid hormone receptor agonists" include liothyronine sodium, repothyroxine sodium.

The "cholesterol absorption inhibitors" include ezetimibe.

The "lipase inhibitors" include orlistat.

The "carnitine palmitoyltransferase inhibitors" include etomoxir.

The "nicotine acid derivatives" include nicotinic acid, nicotinic acid amides, nicomol, nicorandils.

The "bile acid adsorbing drugs" include cholestyramine, cholestyirane and colesevelam hydrochloride.

The "angiotensin converting enzyme inhibitors" include captoril, enalapril maleate, alacepril and cilazapril.

The "angiotensin II receptor antagonists" include candesartan cilexetil, losartan potassium and eprosartan mesylate.

The "endothelin converting enzyme inhibitors" include CGS-31447, CGS-35066.

The "endothelin receptor antagonists" include L-749805, TBC-3214 and BMS-182874.

For example, it is considered to be preferable that the compounds of the present invention are used in combination with at least one kind of drugs selected from the group consisting of insulin sensitivity enhancing drugs (PPARγ agonists, PPARα/γ agonists, PPARδ agonists, PPARα/γ/δ agonists, etc.), glycosidase inhibitors, biguanide drugs, insulin secretion enhancers, insulin formulations and dipeptidyl peptidase IV inhibitors in the treatment of diabetes and the like.

Alternatively, it is considered to be preferable that the compounds of the present invention are used in combination with at least one kind of drugs selected from the group consisting of hydroxymethylglutaryl coenzyme A reductase inhibitors, fibrate compounds, squalene synthetase inhibitors, acyl coenzyme A:cholesterol transacylase inhibitors, low-density lipoprotein receptor enhancers, microsome triglyceride transfer protein inhibitors and anorectic drugs.

The pharmaceutical agent of the present invention can be systemically or topically administered orally or parenterally, for example, intrarectally, subcutaneously, intramuscularly, intravenously and percutaneously.

For the purpose of using a compound of the present invention as a pharmaceutical agent, it can be in a form of a solid composition, a liquid composition or any other form of composition, and a suitable form is selected as required. The pharmaceutical agent of the present invention can be produced by blending a pharmaceutically acceptable carrier with a compound of the present invention. Specifically, excipients, expanders, binding agents, disintegrating agents, coating agents, sugar-coating agents, pH regulators, resolvents or aqueous or a non-aqueous solvents, which are commonly used, may be added to prepare tablets, pills, capsules, granules, powders, powdered drugs, liquid drugs, emulsion, suspension, injection agents by conventional formulation techniques. Examples of excipients and expanders include lactose, magnesium stearate, starch, talc, gelatin, agar, pectin, Arabian gum, olive oil, sesame oil, cocoa butter, ethyleneglycol and other materials commonly used.

In addition, the compounds of the present invention can be formulated by forming a inclusion compound with α-, β- or γ-cyclodextrin or methylated cyclodextrin.

The dose of the compounds of the present invention varies depending on disease, symptoms, weight, age, sex, administration route, etc. but 0.1 to 1000 mg/kg weight/day for an adult is preferable and 0.1-200 mg/kg weight/day is more preferable, which can be administered once a day or divided into multiple doses a day.

The compound of the present invention can be synthesized, for example, by a production process shown below.

The compound wherein ring Ar is represented by Formula (a) can be synthesized according to the following Scheme 1, Scheme 1
[Formula 10]
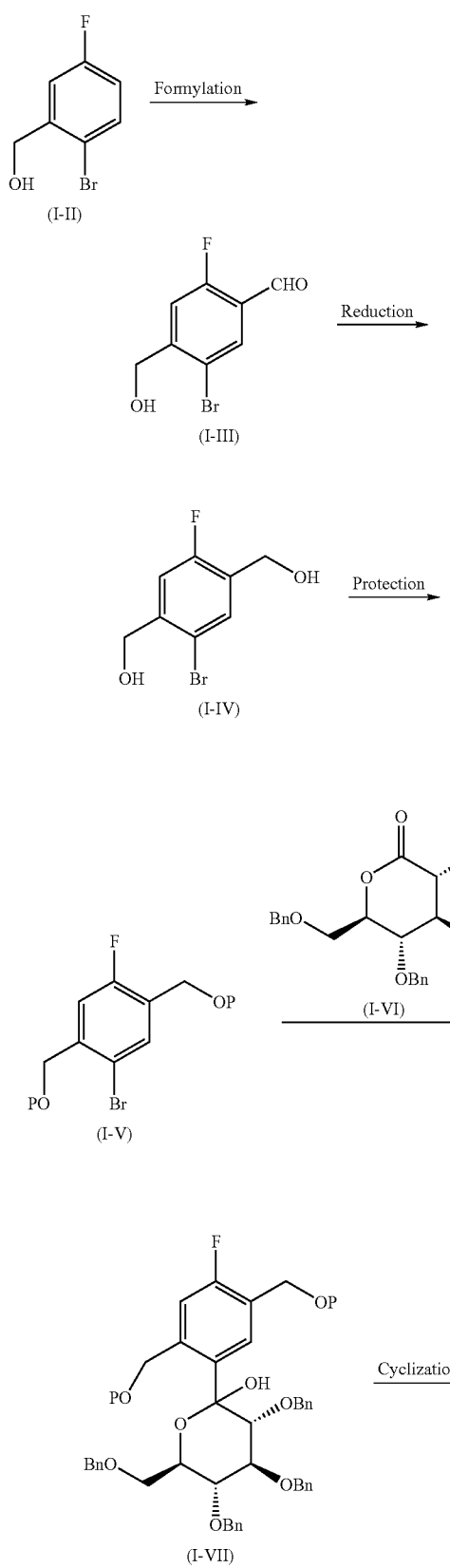
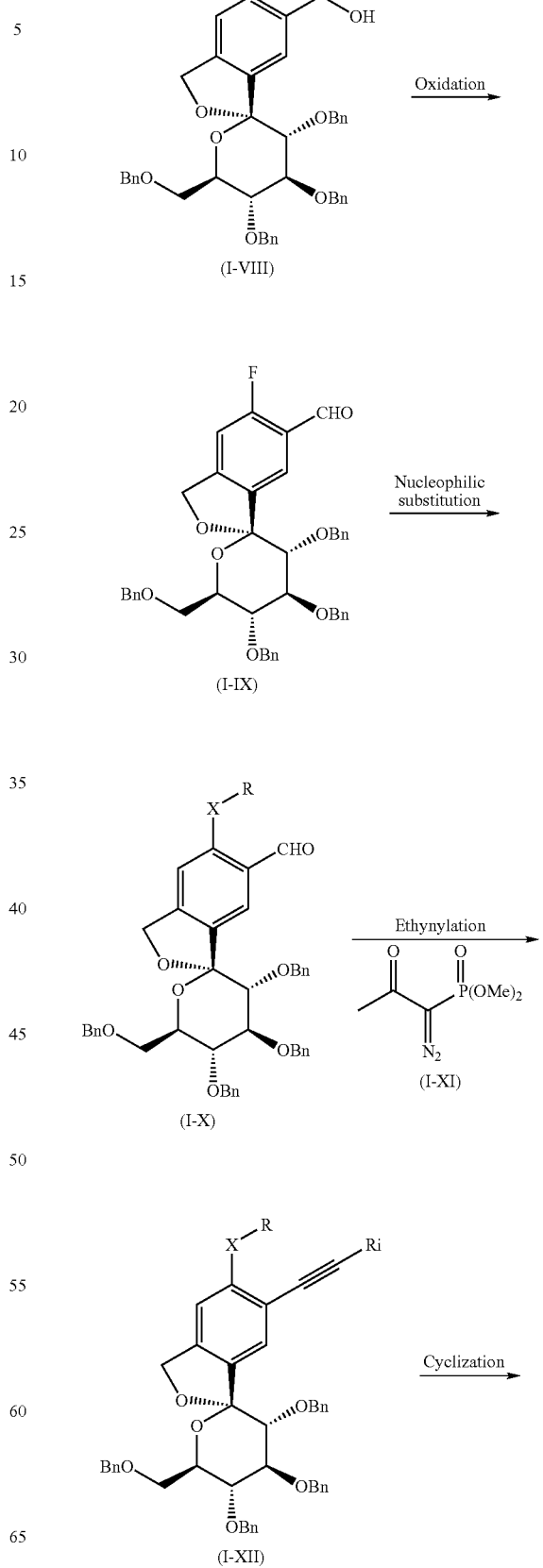

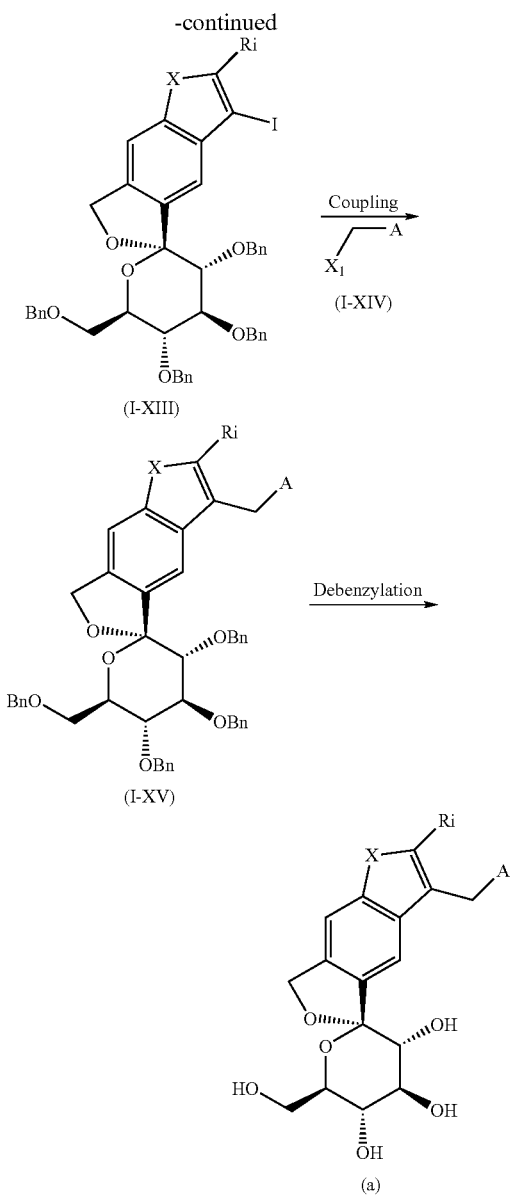

wherein A is an aromatic ring which may have a substituent(s); P is a protecting group of a hydroxyl group; Ri represents a hydrogen atom, a halogen atom, a $C_{1-6}$ alkyl group or a silyl group which may have a substituent(s); R represents a methyl group or an ethyl group; X represents an oxygen atom, a nitrogen atom or a sulfur atom; $X_1$ represents a halogen atom or a boron atom, silicon atom, magnesium atom, zinc atom, tin atom or the like, each of which have a substituent(s).

The reaction converting Compound (I-II) to Compound (I-III) can be achieved using a suitable secondary amine and a suitable alkyllithium in a suitable solvent to carry out selective lithiation at the ortho-position to the fluorine atom in the aromatic ring followed by a subsequent reaction with a suitable electrophile. Examples of a suitable solvent include tetrahydrofuran (THF), diethyl ether, dimethoxyethane, diethoxyethane, dioxane and the like, and tetrahydrofuran and dimethoxyethane are preferred. Examples of a suitable secondary amine include diethylamine, diisopropylamine, dicyclohexylamine, tetramethylpiperidine and the like, and tetramethylpiperidine is preferred. Examples of a suitable alkyllithium include n-butyllithium, sec-butyllithium, tert-butyllithium, methyllithium and the like, and n-butyllithium is preferred. Examples of a suitable electrophile include N,N-dimethylformamide, N-formylmorpholine, N-formylpiperidine and the like, and N,N-dimethylformamide is preferred. The reaction can generally be carried out at about −78° C. to about 25° C. (room temperature), and preferably at about −78° C. to about 0° C., for about 10 minutes to about 2 hours, and preferably for about 30 minutes. Further, Compound (I-II) can be synthesized according to the method described in, for example, J. Org. Chem., 70, p. 756, 2005.

The reaction converting Compound (I-III) to Compound (I-IV) can be achieved by reducing a formyl group with a suitable reducing agent in a suitable solvent. Examples of a suitable solvent include THF, diethyl ether, methanol, ethanol, dichloromethane, 1,2-dichloroethane, toluene, xylene and the like. Examples of a suitable reducing agent include sodium borohydride, lithium borohydride, sodium cyanoborohydride, lithium aluminum hydride, diisopropylaluminum hydride, diborane, a borane-THF complex, a borane-dimethylsulfide complex and the like, and sodium borohydride is preferred. The reaction can generally be carried out at about −78° C. to about 25° C. (room temperature), and preferably at about 0° C. to about 25° C. (room temperature), for about 10 minutes to about 1 hour, and preferably for about 10 minutes.

The reaction converting Compound (I-IV) to Compound (I-V) can be achieved by a reaction with a suitable protecting group introducing reagent in a suitable solvent. Examples of a suitable solvent include THF, diethyl ether, N,N-dimethylformamide, dichloromethane, 1,2-dichloroethane, toluene, xylene and the like. Examples of a suitable protecting group introducing reagent include a reagent for introducing a protecting group which can be removed under acidic conditions, such as trityl chloride, tert-butyldimethylsilyl chloride, methoxymethyl chloride, 3,4-dihydro-2H-pyran, 2-methoxypropene and the like, and 2-methoxypropene is preferred. The reaction can generally be carried out at about −20° C. to about 50° C., and preferably at about 0° C. to about 25° C. (room temperature), for about 10 minutes to 5 hours, and preferably for about 1 hour.

The reaction converting Compound (I-V) to Compound (I-VII) can be achieved by a reaction with a suitable alkyllithium reagent in a suitable solvent, followed by a reaction with Compound (I-VI). Examples of a suitable solvent include THF, diethyl ether, dimethoxyethane, diethoxyethane, dichloromethane, toluene and the like, and THF and toluene are preferred. Examples of a suitable alkyllithium include n-butyllithium, sec-butyllithium, tert-butyllithium, methyllithium and the like, and n-butyllithium is preferred. The reaction can generally be carried out at about −78° C. to about 25° C. (room temperature) for about 10 minutes to about 2 hours, and preferably for about 1 hour. Further, Compound (I-VI) can be synthesized according to the method described in, for example, Carbohydr. Res., 260, p. 243, 1994.

The reaction converting Compound (I-VII) to Compound (I-VIII) can be achieved by a reaction with a suitable acid catalyst in a suitable solvent, while carrying out deprotecting step. Examples of a suitable solvent include THF, dimethoxyethane, diethoxyethane, dichloromethane, toluene, methanol, ethanol, isopropanol and the like, and a mixed solvent of THF and methanol is preferred. Examples of a suitable acid catalyst include p-toluenesulfonic acid, pyridinium p-toluenesulfonic acid, methanesulfonic acid, trifluoromethanesulfonic acid, trifluoroacetic acid, camphorsulphonic acid, hydrochloric acid, sulfuric acid, acetic acid and the like, and p-toluenesulfonic acid is preferred. The reaction can generally be carried out at about −78° C. to about 100° C., and preferably at about 0° C. to about 60° C., for about 10 minutes to about 24 hours, and preferably for about 2 hours. Further, in this step the resulting spiro moiety undergoes isomerization at the same time as cyclization, whereby the compound is obtained as a single product having a desired configuration.

The reaction converting Compound (I-VIII) to Compound (I-IX) can be achieved by a reaction with a suitable oxidizing agent in a suitable solvent. Examples of a suitable solvent include dichloromethane, 1,2-dichloroethane, toluene, xylene and the like, and dichloromethane is preferred. Examples of a suitable oxidizing agent include a Dess-Martin reagent, TPAP-NMO, DMSO-acetic anhydride, DMSO-oxalyl chloride, manganese dioxide, chromic acid-sulfuric acid, $SO_3$-pyridine and the like, and manganese dioxide is preferred. The reaction can generally be carried out at about −78° C. to about 40° C., and preferably at about 0° C. to about 25° C. (room temperature) for about 10 minutes to about 24 hours, and preferably for about 2 hours.

The reaction converting Compound (I-IX) to Compound (I-X) can be achieved by a reaction with a suitable nucleophilic reagent in a suitable solvent. Examples of a suitable solvent include THF, dimethoxyethane, diethoxyethane, dioxane, N,N-dimethylformamide, N,N-dimethylacetamide, dichloromethane, 1,2-dichloroethane, toluene, xylene and the like, and N,N-dimethylformamide and N,N-dimethylacetamide are preferred. Examples of a suitable nucleophilic reagent include sodium thiomethoxide, sodium methoxide and the like. The reaction can generally be carried out at about 0° C. to about 120° C., and preferably at about 0° C. to about 25° C. (room temperature) for about 10 minutes to about 5 hours, and preferably for about 30 minutes.

The reaction converting Compound (I-X) to Compound (I-XII) can be achieved by a reaction with a suitable base and a suitable ethynylating agent in a suitable solvent. Examples of a suitable solvent include THF, dimethoxyethane, diethoxyethane, dioxane, dichloromethane, 1,2-dichloroethane, toluene, xylene, methanol, ethanol and the like, and a mixed solvent of THF and methanol is preferred. Examples of a suitable base include potassium carbonate, sodium carbonate, sodium hydroxide, potassium hydroxide and the like. Examples of a suitable ethynylating agent include dimethyl (1-diazo-2-oxopropyl)phosphonate (I-XI). The reaction can generally be carried out at about 0° C. to about 120° C., and preferably at about 0° C. to about 25° C. (room temperature) for about 10 minutes to about 5 hours, and preferably for about 30 minutes. Further, the ethynylating agent (I-XI) can be synthesized according to the method described in, for example, Eur. J. Org. Chem., p. 821, 2003.

The reaction converting Compound (I-XII) to Compound (I-XIII) can be achieved by a reaction with iodine in a suitable solvent. Examples of a suitable solvent include dichloromethane, 1,2-dichloroethane and the like, and dichloromethane is preferred. The reaction can generally be carried out at about −20° C. to about 50° C., and preferably at about 0° C. to about 25° C. (room temperature), for about 10 minutes to about 4 hours, and preferably for about 15 minutes.

The reaction converting Compound (I-XIII) to Compound (I-XV) can be achieved by a reaction with a suitable alkylating agent (I-XIV) in the presence of a suitable transition metal catalyst, a suitable ligand and a suitable base in a suitable solvent. Examples of a suitable solvent include THF, dimethoxyethane, diethoxyethane, dioxane, N,N-dimethylformamide, N,N-dimethylacetamide, DMSO, 1,2-dichloroethane, toluene, xylene, ethanol, acetonitrile and the like. Examples of a suitable transition metal catalyst include palladium, nickel, cobalt chloride, iron and the like. Examples of a suitable ligand include triphenylphosphine, tri(tert-butyl) phosphine, 2,2'-bis(diphenylphosphino)-1,1'-binaphthalene (BINAP), 1,2-bis(diphenylphosphino)ethane (dppe), 1,3-bis (diphenylphosphino)propane (dppp), 1,4-bis(diphenylphosphino)butane (dppb), 1,1'-bis(diphenylphosphino)ferrocene (dppf) and the like. Examples of a suitable base include potassium acetate, sodium acetate, potassium phosphate, sodium phosphate, dipotassium hydrogen phosphate, sodium hydroxide, potassium hydroxide, sodium carbonate, potassium carbonate, cesium carbonate, triethylamine, diisopropylethylamine, 1,8-diazabicyclo[5,4,0]-7-undecene (DBU), 1,5-diazabicyclo-[4,3,0]-5-nonene (DBN), sodium tert-butoxide, potassium tert-butoxide, tetramethylguanidine and the like. Examples of a suitable alkylating agent include alkylboronic acid, alkylboronic acid dialkyl ester, an alkylmagnesium halide, dialkylzinc, alkyllithium, alkyltin, alkylsilane and the like. The reaction can generally be carried out at about 0° C. to about 200° C., and preferably at about 25° C. (room temperature) to about 100° C., for about 10 minutes to about 24 hours, and preferably for about 3 hours.

The reaction converting Compound (I-XV) to the compound wherein ring Ar is represented by Formula (a) can be achieved by a reaction with a suitable debenzylating reagent in a suitable solvent. Examples of a suitable solvent include THF, ethyl acetate, methanol, ethanol, dichloromethane and the like. Examples of a suitable debenzylating reagent include palladium on carbon and hydrogen gas, palladium hydroxide on carbon and hydrogen gas, Raney nickel and hydrogen gas, boron trichloride, boron tribromide, ethanethiol sodium salt, trimethylsilyl iodide and the like, and preferred examples are palladium on carbon and hydrogen gas, and boron trichloride. The reaction can generally be carried out at about −78° C. to about 100° C., and preferably at about −78° C. to room temperature, for about 1 hour to about 24 hours, and preferably for about 3 hours.

The compound wherein ring Ar is represented by Formula (b) can be produced according to the following Scheme 2,

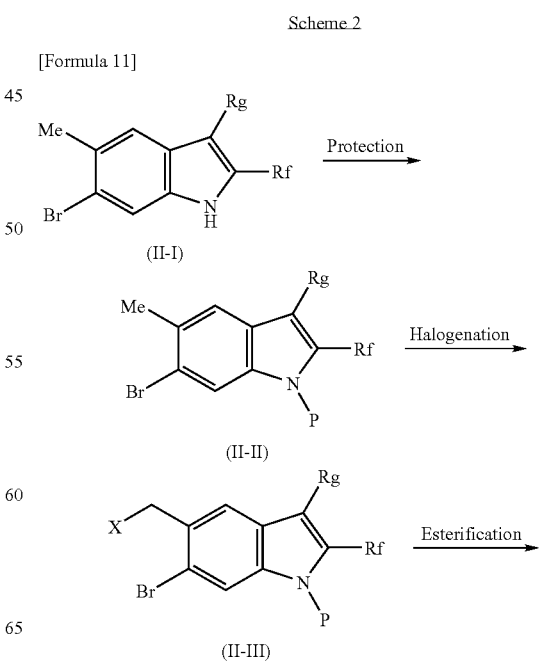

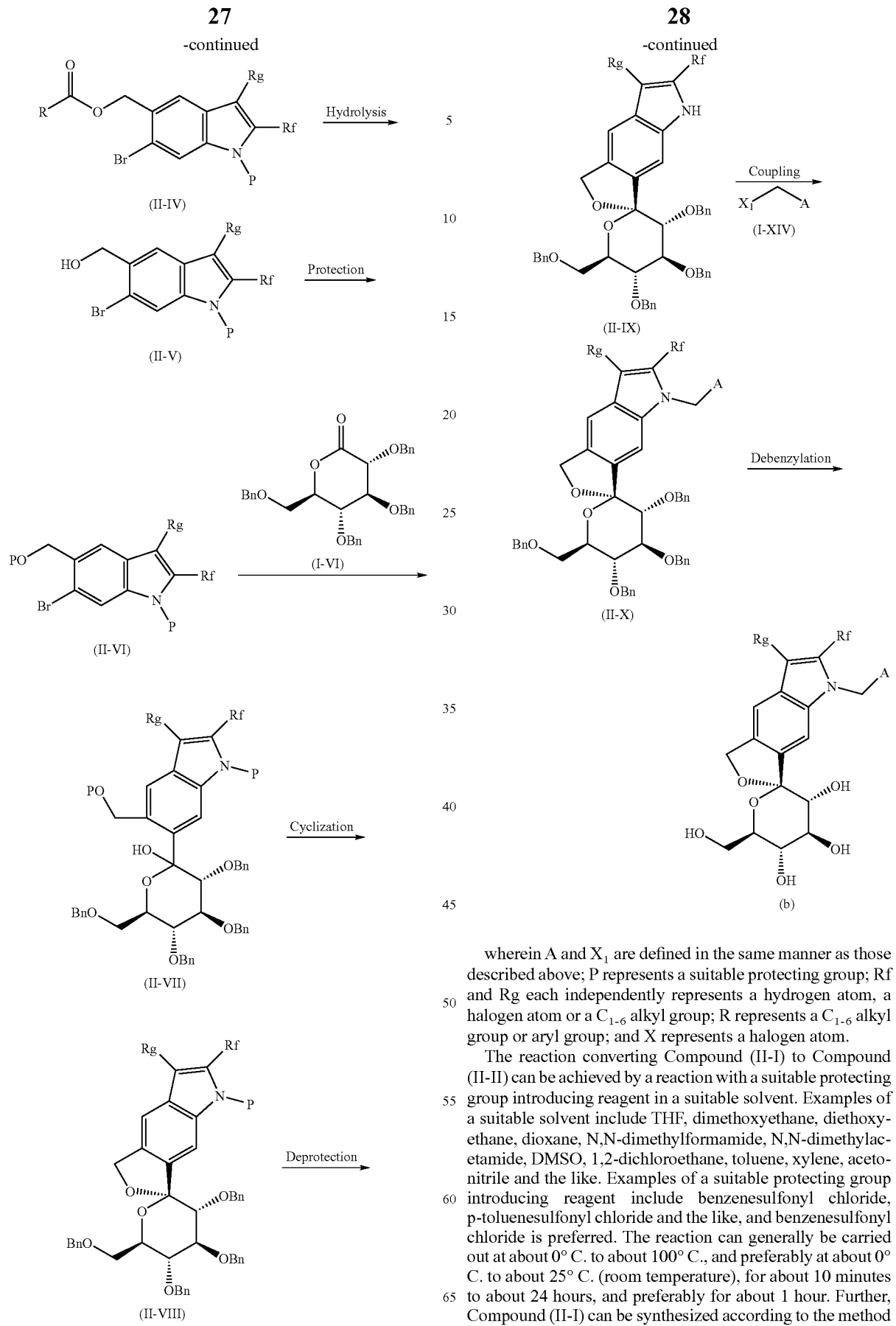

wherein A and $X_1$ are defined in the same manner as those described above; P represents a suitable protecting group; Rf and Rg each independently represents a hydrogen atom, a halogen atom or a $C_{1-6}$ alkyl group; R represents a $C_{1-6}$ alkyl group or aryl group; and X represents a halogen atom.

The reaction converting Compound (II-I) to Compound (II-II) can be achieved by a reaction with a suitable protecting group introducing reagent in a suitable solvent. Examples of a suitable solvent include THF, dimethoxyethane, diethoxyethane, dioxane, N,N-dimethylformamide, N,N-dimethylacetamide, DMSO, 1,2-dichloroethane, toluene, xylene, acetonitrile and the like. Examples of a suitable protecting group introducing reagent include benzenesulfonyl chloride, p-toluenesulfonyl chloride and the like, and benzenesulfonyl chloride is preferred. The reaction can generally be carried out at about 0° C. to about 100° C., and preferably at about 0° C. to about 25° C. (room temperature), for about 10 minutes to about 24 hours, and preferably for about 1 hour. Further, Compound (II-I) can be synthesized according to the method described in, for example, Synlett, 10, p. 1594, 1999.

The reaction converting Compound (II-II) to Compound (II-III) can be achieved by a reaction with a suitable halogenating reagent in the presence of a suitable radical initiator in a suitable solvent. Examples of a suitable solvent include dichloromethane, 1,2-dichloroethane, carbon tetrachloride, benzene, nitrobenzene, heptane and the like, and carbon tetrachloride is preferred. Examples of a suitable radical initiator include 2,2'-azobis(isobutyronitrile) (AIBN), benzoyl peroxide, tert-butyl peroxide, triethylborane and the like, and AIBN is preferred. Examples of a suitable halogenating reagent include N-chloromosuccinimide (NCS), N-bromosuccinimide (NBS), 1,3-dichloro-5,5-dimethylhydantoin, 1,3-dibromo-5,5-dimethylhydantoin and the like, and NBS is preferred. The reaction can generally be carried out at about −78° C. to about 100° C., and preferably at about 80° C., for about 10 minutes to about 12 hours, and preferably for about 1 hour.

The reaction converting Compound (II-III) to Compound (II-IV) can be achieved by a reaction with a suitable metal salt of a carboxylic acid in a suitable solvent. Examples of a suitable solvent include THF, dimethoxyethane, diethoxyethane, dioxane, N,N-dimethylformamide, N,N-dimethylacetamide, dimethylsulfoxide (DMSO), 1,2-dichloroethane, toluene, xylene, acetonitrile and the like, and N,N-dimethylformamide is preferred. Examples of a suitable metal salt of a carboxylic acid include sodium acetate, potassium acetate, cesium acetate, sodium benzoate, potassium benzoate and the like, and sodium acetate is preferred. The reaction can generally be carried out at about 0° C. to about 100° C., and preferably at about 80° C., for about 10 minutes to about 24 hours, and preferably for about 2 hours.

The reaction converting Compound (II-IV) to Compound (II-V) can be achieved by a reaction with a suitable base in a suitable solvent. Examples of a suitable solvent include THF, dimethoxyethane, diethoxyethane, dioxane, 1,2-dichloroethane, toluene, xylene, acetonitrile, methanol, ethanol and the like, and methanol is preferred. Examples of a suitable base include lithium hydroxide, sodium hydroxide, potassium hydroxide, barium hydroxide, tetrabutylammonium hydroxide, potassium carbonate, sodium carbonate and the like, and potassium carbonate is preferred. The reaction can generally be carried out at 0° C. to room temperature, and preferably at room temperature, for about 10 minutes to about 12 hours, and preferably for about 1 hour.

The reaction converting Compound (II-V) to Compound (II-VI) can be achieved according to the same conditions as those in the above-described reaction in which Compound (I-V) was synthesized from Compound (I-IV).

The reaction converting Compound (II-VI) to Compound (II-VII) can be achieved according to the same conditions as those in the above-described reaction in which Compound (I-VII) was synthesized from Compound (I-V).

The reaction converting Compound (II-VII) to Compound (II-VIII) can be achieved according to the same conditions as those in the above-described reaction in which Compound (I-VIII) was synthesized from Compound (I-VII).

The reaction converting Compound (II-VIII) to Compound (II-IX) can be achieved by a reaction with a suitable deprotecting reagent that is appropriate for the protecting group on the nitrogen atom in a suitable solvent. Examples of a suitable solvent include THF, dimethoxyethane, diethoxyethane, dioxane, N,N-dimethylformamide, N,N-dimethylacetamide, DMSO, 1,2-dichloroethane, toluene, xylene, acetonitrile, methanol, ethanol and the like, and a mixed solvent of THF and ethanol is preferred. Examples of a suitable deprotecting reagent include sodium hydroxide, potassium hydroxide and the like, and potassium hydroxide is preferred. The reaction can generally be carried out at about 0° C. to about 100° C., and preferably at about 25° C. (room temperature) to about 50° C., for about 10 minutes to 24 hours, and preferably for about 3 hours.

The reaction converting Compound (II-IX) to Compound (II-X) can be achieved by a reaction with a suitable base and a suitable benzyl halide derivative in a suitable solvent. Examples of a suitable solvent include THF, dimethoxyethane, diethoxyethane, dioxane, N,N-dimethylformamide, N,N-dimethylacetamide, DMSO, 1,2-dichloroethane, toluene, xylene, acetonitrile and the like, and N,N-dimethylformamide is preferred. Examples of a suitable base include sodium hydride, potassium hydride, sodium hydroxide, potassium hydroxide and the like, and sodium hydride is preferred. Examples of a suitable benzyl halide derivative include para-substituted benzyl bromide, para-substituted benzyl chloride, meta-substituted benzyl bromide, meta-substituted benzyl chloride, ortho-substituted benzyl bromide, ortho-substituted benzyl chloride and the like. The reaction can generally be carried out at about 0° C. to about 100° C., and preferably at about 0° C. to about 25° C. (room temperature), for about 10 minutes to 12 hours, and preferably for about 2 hours.

The reaction converting Compound (II-X) to the compound wherein ring Ar is represented by Formula (b) can be achieved according to the same conditions as those in the above-described reaction in which the compound wherein ring Ar is represented by Formula (a) was synthesized from Compound (I-XV).

The synthetic intermediate (XVII: Rf and Rg are a hydrogen atom, P is a benzenesulfonyl group) of Scheme 2 can also be produced according to the method of the following Scheme 2',

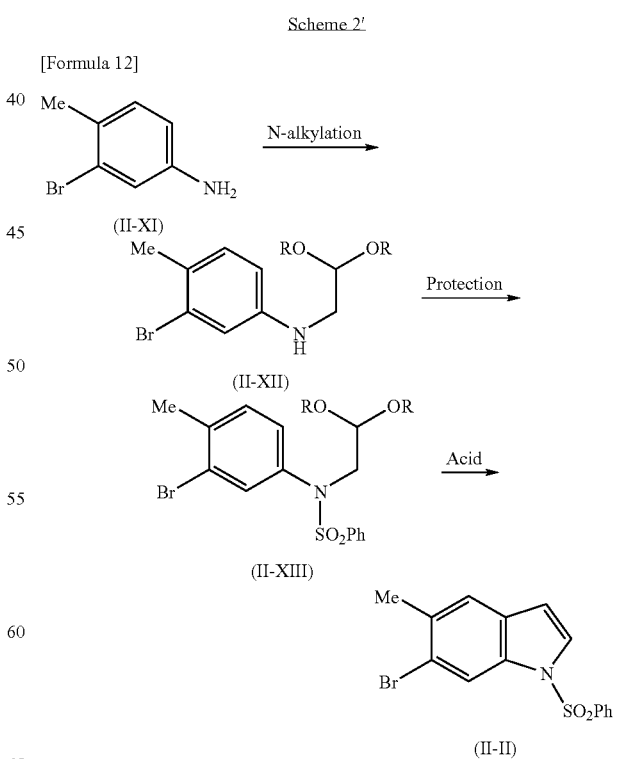

wherein R represents a $C_{1-6}$ alkyl group.

The reaction converting Compound (II-XI) to Compound (II-XII) can be achieved by a reaction with a suitable base and a suitable haloacetaldehyde dialkylacetal in a suitable solvent. Examples of a suitable solvent include ethanol, methanol, THF, dimethoxyethane, diethoxyethane, dioxane, N,N-dimethylformamide, N,N-dimethylacetamide, DMSO, 1,2-dichloroethane, toluene, xylene, acetonitrile and the like, and ethanol is preferred. Examples of a suitable base include triethylamine, diisopropylethylamine, N-methylmorpholine, pyridine, sodium carbonate, potassium carbonate and the like, and triethylamine is preferred. Examples of a suitable haloacetaldehyde dialkylacetal include bromoacetaldehyde dimethylacetal, chloroacetaldehyde dimethylacetal, bromoacetaldehyde diethylacetal, chloroacetaldehyde diethylacetal, 2-bromomethyl-1,3-dioxolane, 2-chloromethyl-1,3-dioxolane and the like, and bromoacetaldehyde dimethylacetal is preferred. The reaction can generally be carried out at about 0° C. to about 170° C., and preferably at about 25° C. (room temperature) to about 150° C., for about 1 hour to about 24 hours.

The reaction converting Compound (II-XII) to Compound (II-XIII) can be achieved by a reaction with a suitable base and benzenesulfonyl chloride in a suitable solvent. Examples of a suitable solvent include dichloromethane, 1,2-dichloroethane, THF, dimethoxyethane, diethoxyethane, dioxane and the like, and dichloromethane is preferred. Examples of a suitable base include pyridine, triethylamine, diisopropylethylamine, N-methylmorpholine, 4-(N,N-dimethylamino)pyridine, sodium carbonate, potassium carbonate and the like, and pyridine is preferred. The reaction can generally be carried out at about 0° C. to about 100° C., and preferably at about 0° C. to about 25° C. (room temperature), for about 10 minutes to 24 hours.

The reaction converting Compound (II-XIII) to Compound (II-II) can be achieved by a treatment with a suitable acid in a suitable solvent. Examples of a suitable solvent include toluene, benzene, dichloromethane, 1,2-dichloroethane and the like, and toluene is preferred. Examples of a suitable acid include titanium tetrachloride, aluminum chloride, tin tetrachloride, polyphosphoric acid and the like, and titanium tetrachloride is preferred. The reaction can generally be carried out at about 0° C. to about 150° C., and preferably at about 25° C. (room temperature) to about 130° C., for about 10 minutes to about 12 hours.

The synthetic intermediate (II-IX: Rf and Rg are a hydrogen atom) of Scheme 2 can also be produced according to the method of the following Scheme 2", Scheme 2"

[Formula 13]

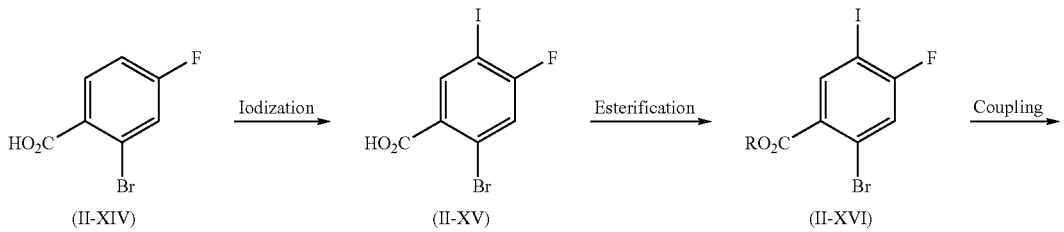

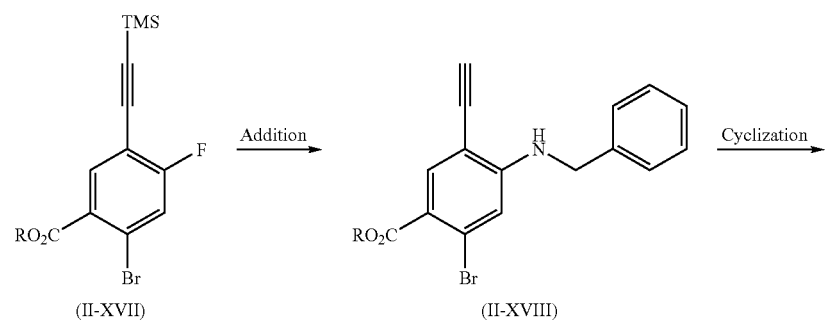

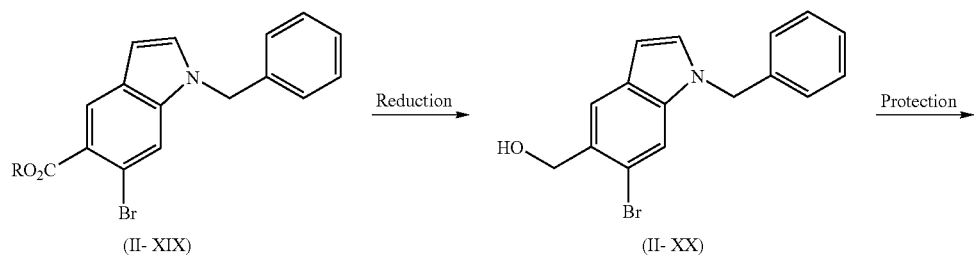

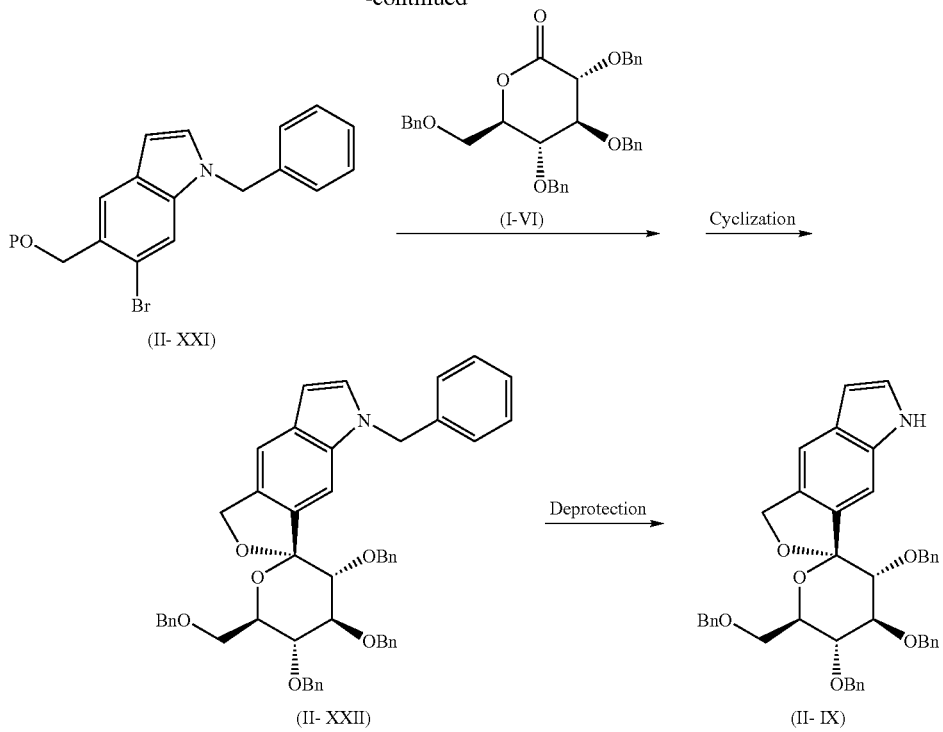

wherein P represents a suitable protecting group and R represents a $C_{1-6}$ alkyl group.

The reaction converting Compound (II-XIV) to Compound (II-XV) can be achieved by a reaction with a suitable iodizing agent in the presence of a suitable acid. Examples of a suitable acid include trifluoromethanesulfonic acid, sulfuric acid, fuming sulfuric acid and the like, and trifluoromethanesulfonic acid is preferred. Examples of a suitable iodizing agent include N-iodosuccinimide, iodine and the like, and N-iodosuccinimide is preferred. The reaction can generally be carried out at about 0° C. to about 100° C., and preferably at about 0° C. to about 25° C. (room temperature), for about 30 minutes to 12 hours, and preferably for about 1 hour to about 4 hours.

The reaction converting Compound (II-XV) to Compound (II-XVI) can be achieved by a reaction with a suitable acid in a suitable alcohol solvent. Examples of a suitable alcohol solvent include methanol, ethanol, 2-propanol, cyclohexanol and the like, and methanol is preferred. Examples of a suitable acid include sulfuric acid, hydrochloric acid, methanesulfonic acid and the like, and sulfuric acid is preferred. The reaction can generally be carried out at about 25° C. (room temperature) to about 100° C., and preferably at about 50° C. to about 80° C., for about 30 minutes to 12 hours, and preferably for about 2 hours to about 5 hours.

The reaction converting Compound (II-XVI) to Compound (II-XVII) can be achieved by a reaction with ethynyltrimethylsilane in the presence of a suitable catalyst and a suitable amine base in a suitable solvent. Examples of a suitable solvent include THF, 1,2-dimethoxyethane, dioxane and the like, and THF is preferred. Examples of a suitable catalyst include the combination of dichlorobis[triphenylphosphine]palladium and copper(I) chloride. Examples of a suitable amine base include triethylamine, diisopropylethylamine and the like. The reaction can generally be carried out at about 25° C. (room temperature) to about 100° C. for about 1 hour to about 6 hours.

The reaction converting Compound (II-XVII) to Compound (II-XVIII) can be achieved by a reaction with benzylamine in the presence of a suitable amine base in a suitable solvent. Examples of a suitable solvent include acetonitrile, THF, 1,2-dimethoxyethane, N,N-dimethylformamide and the like, and acetonitrile is preferred. Examples of a suitable amine base include triethylamine, diisopropylethylamine and the like. The reaction can generally be carried out at about 60° C. to about 150° C. for about 30 minutes to about 24 hours.

The reaction converting Compound (II-XVIII) to Compound (II-XIX) can be achieved by reacting in the presence of a suitable catalyst in a suitable solvent. Examples of a suitable solvent include 1,2-dichloroethane. Examples of a suitable solvent include copper(II) acetate. The reaction can generally be carried out at about 25° C. (room temperature) to about 130° C. for about 30 minutes to 24 hours.

The reaction converting Compound (II-XIX) to Compound (II-XX) can be achieved by reducing with a suitable reducing agent in a suitable solvent. Examples of a suitable solvent include dichloromethane, 1,2-dichloroethane, toluene, xylene, THF, diethyl ether, and the like, and dichloromethane is preferred. Examples of a suitable reducing agent include diisobutylaluminum hydride, lithium aluminum hydride and the like. The reaction can generally be carried out at about −78° C. to about 25° C. (room temperature) for about 30 minutes to 12 hours, and preferably for about 1 hour to about 3 hours.

The reaction converting Compound (II-XX) to Compound (II-XXII) can be achieved according to the same methods as the reaction of from Compound (II-V) to Compound (II-VII) of Scheme 2.

The reaction converting Compound (II-XXII) to Compound (II-IX) can be achieved by mixing dimethylsulfoxide and a solution of potassium tert-butoxide in THF, followed by continuously charging oxygen gas to the resultant solution with stirring at room temperature. The reaction can generally be carried out at about 25° C. (room temperature) for about 5 minutes to about 1 hour. Further, this reaction can also be carried out with reference to the method described in Tetrahedron Lett., 43, p. 399, 2002.

The compound wherein ring Ar is represented by Formula (f) can also be produced according to the following Scheme 3,

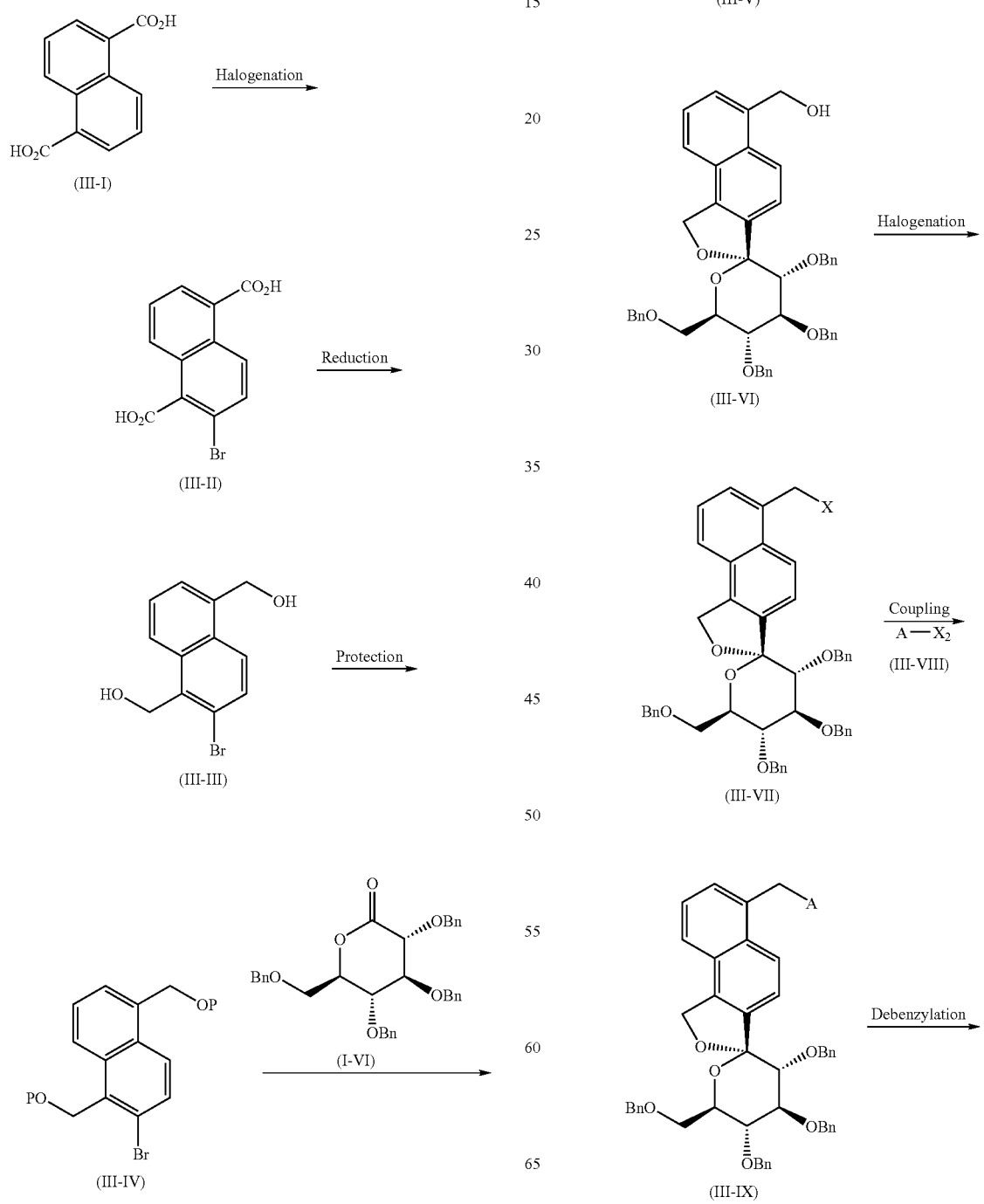

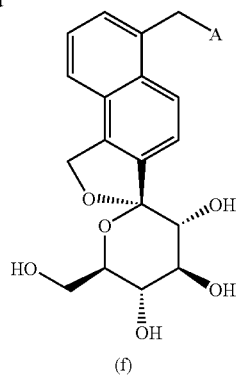

(f)

wherein A is defined in the same manner as described above; P represents a protecting group of a hydroxyl group; X represents a halogen atom; and $X_2$ represents a boron atom, a silicon atom, a magnesium atom, a zinc atom, a tin atom or the like, each of which have a substituent(s).

The reaction converting Compound (III-I) to Compound (III-II) can be achieved by a reaction with a suitable base and a suitable halogenating agent in a suitable solvent. Examples of a suitable solvent include THF, dimethoxyethane, diethoxyethane, dioxane, 1,2-dichloroethane, toluene, xylene and the like. Examples of a suitable base include the combination of n-butyllithium and tert-butoxypotassium. Examples of a suitable halogenating agent include 1,2-dibromotetrachloroethane, bromine, iodine and the like. The reaction can generally be carried out at about −78° C. to about −0° C., and preferably at about −78° C. to about −50° C. for about 1 hour to about 5 hours, and preferably for about 3 hours. Further, Compound (III-I) can be synthesized according to the method described in, for example, Bull. Chem., Soc. Jpn., 71, p. 1285, 1998. In addition, this reaction can be carried out with reference to the method described in Chem. Lett., 34, p. 446, 2005.

The reaction converting Compound (III-II) to Compound (III-III) can be achieved by reducing two carboxylic acid groups with a suitable reducing agent in a suitable solvent. Examples of a suitable solvent include THF, diethyl ether, dimethoxyethane, diethoxyethane, dichloromethane, 1,2-dichloroethane, toluene, xylene and the like. Examples of a suitable reducing agent include the combination of sodium borohydride and a boranetrifluoride-diethyl ether complex, lithium aluminum hydride, diisopropylaluminum hydride, diborane, a borane-THF complex, a borane-dimethyl sulfide complex and the like, and a borane-THF complex is preferred. The reaction can generally be carried out at about −78° C. to about 60° C., and preferably at about 0° C. to about 25° C. (room temperature), for about 10 minutes to about 24 hours, and preferably for about 2 hours.

The reaction converting Compound (III-III) to Compound (III-IV) can be achieved according to the same conditions as those in the above-described reaction in which Compound (I-V) was synthesized from Compound (I-IV).

The reaction converting Compound (III-IV) to Compound (III-V) can be achieved according to the same conditions as those in the above-described reaction in which Compound (I-VII) was synthesized from Compound (I-V).

The reaction converting Compound (III-V) to Compound (III-VI) can be achieved according to the same conditions as those in the above-described reaction in which Compound (I-VIII) was synthesized from Compound (I-VII).

The reaction converting Compound (III-VI) to Compound (III-VII) can be achieved by a reaction with a suitable halogenating agent in a suitable solvent. Examples of a suitable solvent include dichloromethane, 1,2-dichloroethane, benzene, carbon tetrachloride and the like. Examples of suitable halogenating agents include carbon tetrachloride and triphenylphosphine, carbon tetrabromide and triphenylphosphine, sulfonyl chloride, oxalyl chloride, phosphorus trichloride, phosphorus tribromide and the like. The reaction can generally be carried out at about −20° C. to about 50° C., and preferably at about 0° C. to about 25° C. (room temperature), for about 1 hour to about 24 hours, and preferably for about 2 hours.

The reaction converting Compound (III-VII) to Compound (III-IX) can be achieved by a reaction with an arylating agent (III-VIII) in the presence of a suitable transition metal catalyst, a suitable ligand and a suitable base in a suitable solvent. Examples of a suitable solvent include THF, dimethoxyethane, diethoxyethane, dioxane, N,N-dimethylformamide, N,N-dimethylacetamide, DMSO, 1,2-dichloroethane, toluene, xylene, ethanol, acetonitrile and the like. Examples of a suitable transition metal catalyst include palladium, nickel, cobalt, iron and the like. Examples of a suitable base include potassium acetate, sodium acetate, potassium phosphate, sodium phosphate, dipotassium hydrogen phosphate, sodium hydroxide, potassium hydroxide, sodium carbonate, potassium carbonate, cesium carbonate, triethylamine, diisopropylethylamine, DBU, DBN, sodium tert-butoxide, potassium tert-butoxide, tetramethylguanidine and the like. Examples of a suitable arylating agent include arylboronic acid, an arylmagnesium halide, aryizinc, aryllithium, aryltin, arylsilane and the like. The reaction can generally be carried out at about 0° C. to about 200° C., and preferably at about 25° C. (room temperature) to about 100° C., for about 10 minutes to about 24 hours, and preferably for about 2 hours.

The reaction converting Compound (III-IX) to the compound wherein ring Ar is represented by Formula (f) can be achieved according to the same conditions as those in the above-described reaction in which the compound wherein ring Ar is represented by Formula (a) was synthesized from Compound (I-XV).

The compound wherein ring Ar is represented by Formula (f) can also be produced according to the following Scheme 4, Scheme 4

[Formula 15]

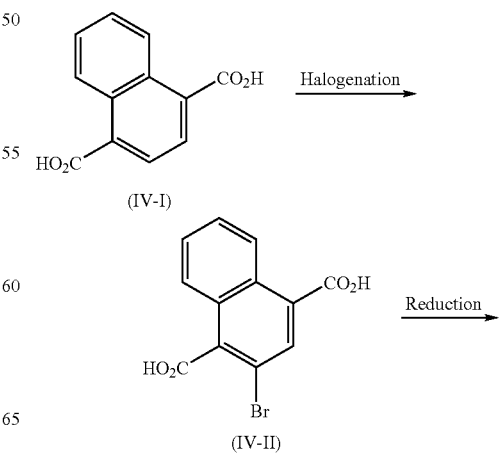

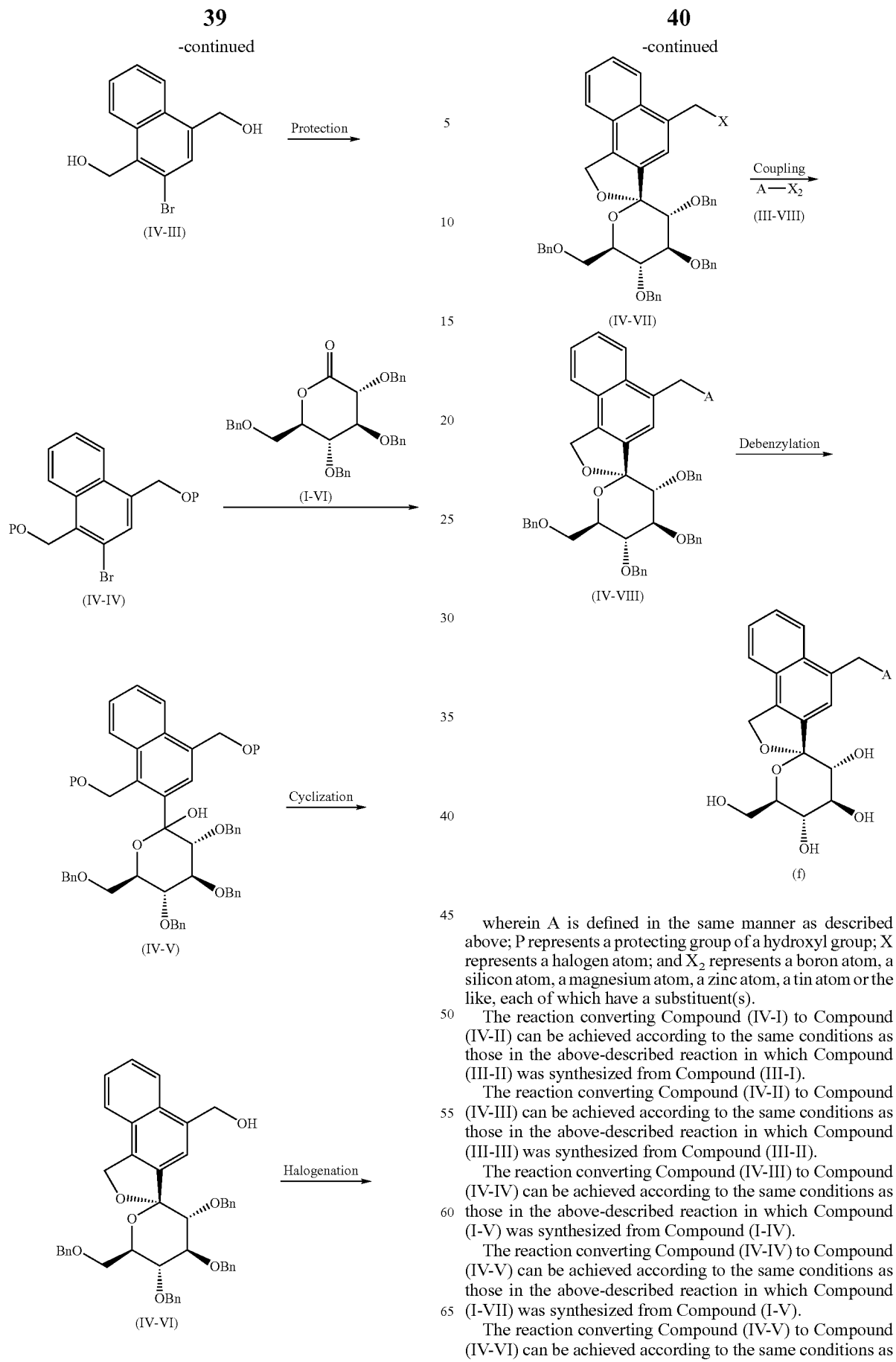

wherein A is defined in the same manner as described above; P represents a protecting group of a hydroxyl group; X represents a halogen atom; and $X_2$ represents a boron atom, a silicon atom, a magnesium atom, a zinc atom, a tin atom or the like, each of which have a substituent(s).

The reaction converting Compound (IV-I) to Compound (IV-II) can be achieved according to the same conditions as those in the above-described reaction in which Compound (III-II) was synthesized from Compound (III-I).

The reaction converting Compound (IV-II) to Compound (IV-III) can be achieved according to the same conditions as those in the above-described reaction in which Compound (III-III) was synthesized from Compound (III-II).

The reaction converting Compound (IV-III) to Compound (IV-IV) can be achieved according to the same conditions as those in the above-described reaction in which Compound (I-V) was synthesized from Compound (I-IV).

The reaction converting Compound (IV-IV) to Compound (IV-V) can be achieved according to the same conditions as those in the above-described reaction in which Compound (I-VII) was synthesized from Compound (I-V).

The reaction converting Compound (IV-V) to Compound (IV-VI) can be achieved according to the same conditions as those in the above-described reaction in which Compound (I-VIII) was synthesized from Compound (I-VII).

The reaction converting Compound (IV-VI) to Compound (IV-VII) can be achieved according to the same conditions as those in the above-described reaction in which Compound (III-VII) was synthesized from Compound (III-VI).

The reaction converting Compound (IV-VII) to Compound (IV-VIII) can be achieved according to the same conditions as those in the above-described reaction in which Compound (III-IX) was synthesized from Compound (III-VII).

The reaction converting Compound (IV-VIII) to the compound wherein ring Ar is represented by Formula (f) can be achieved according to the same conditions as those in the above-described reaction in which the compound wherein ring Ar is represented by Formula (a) was synthesized from Compound (I-XV).

The synthetic intermediate (IV-III) of Scheme 4 can also be produced according to the method of the following Scheme 4'.

Scheme 4'

[Formula 16]

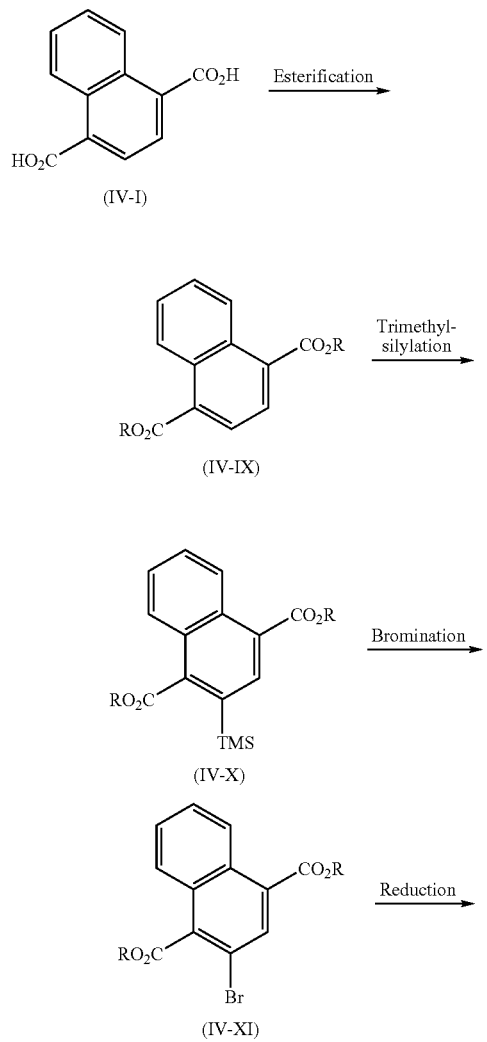

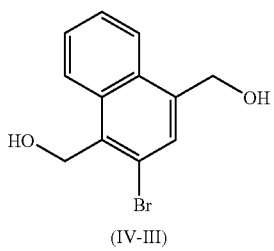

(IV-III)

The reaction converting Compound (IV-I) to Compound (IV-IX) can be achieved by a reaction with a suitable acid in a suitable alcohol solvent. Examples of a suitable alcohol solvent include 2-propanol, ethanol, methanol, tart-butanol and the like, and 2-propanol is preferred. Examples of a suitable acid include sulfuric acid, hydrochloric acid, methanesulfonic acid and the like, and sulfuric acid is preferred. The reaction can generally be carried out at about 0° C. to about 130° C., and preferably at about 25° C. (room temperature) to about 100° C., for about 30 minutes to about 12 hours, and preferably for about 2 to 5 hours.

The reaction converting Compound (IV-IX) to Compound (IV-X) can be achieved by a reaction with a suitable base and a suitable trimethylsilylating agent in a suitable solvent. Examples of a suitable solvent include THF, dimethoxyethane, diethoxyethane, dioxane, 1,2-dichloroethane, toluene, xylene, n-hexane and the like, and THF is preferred. Examples of a suitable base include lithium 2,2,6,6-tetramethylpiperazide, lithium diisopropylamide and the like. Examples of a suitable trimethylsilylating agent include chlorotrimethylsilane, trimethylsilyl p-toluenesulfonate and the like. The reaction can generally be carried out at about −78° C. to about 25° C. (room temperature) for about 30 minutes to about 5 hours. The reaction may preferably be carried out by starting the reaction at about −78° C. and then warming to room temperature over about 1 to 2 hours.

The reaction converting Compound (IV-X) to Compound (IV-XI) can be achieved by a reaction with a suitable brominating agent in a suitable solvent. Examples of a suitable solvent include acetonitrile, 1,2-dichloroethane, toluene and the like, and acetonitrile is preferred. Examples of a suitable brominating agent include N-bromosuccinimide. The reaction can generally be carried out at about 50° C. to about 150° C. for about 10 minutes to about 12 hours.

The reaction converting Compound (IV-XI) to Compound (IV-III) can be achieved by reducing two ester groups with a suitable reducing agent in a suitable solvent. Examples of a suitable solvent include dichloromethane, 1,2-dichloroethane, toluene, xylene, THF, diethyl ether and the like. Examples of a suitable reducing agent include diisopropylaluminum hydride, lithium aluminum hydride and the like. The reaction can generally be carried out at about −78° C. to about 60° C., and preferably at about −78° C. to about 25° C. (room temperature), for about 10 minutes to 12 hours, and preferably for about 1 to 3 hours.

The compound wherein ring Ar is represented by Formula (d) can also be produced according to the method of the following Scheme 5,
Scheme 5
[Formula 17]
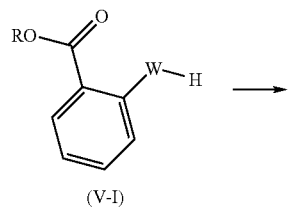
(V-I)
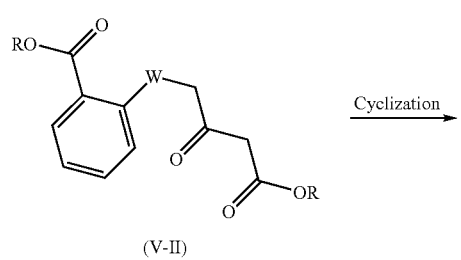
(V-II)
→ Cyclization →
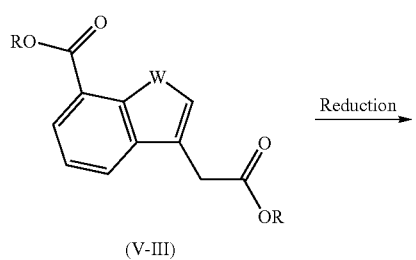
(V-III)
→ Reduction →
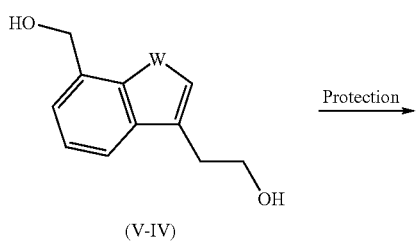
(V-IV)
→ Protection →
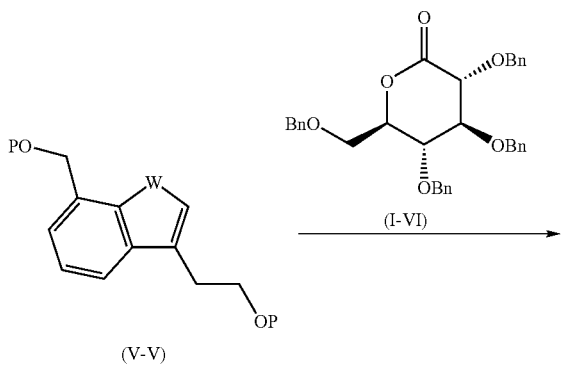
(V-V) + (I-VI) →
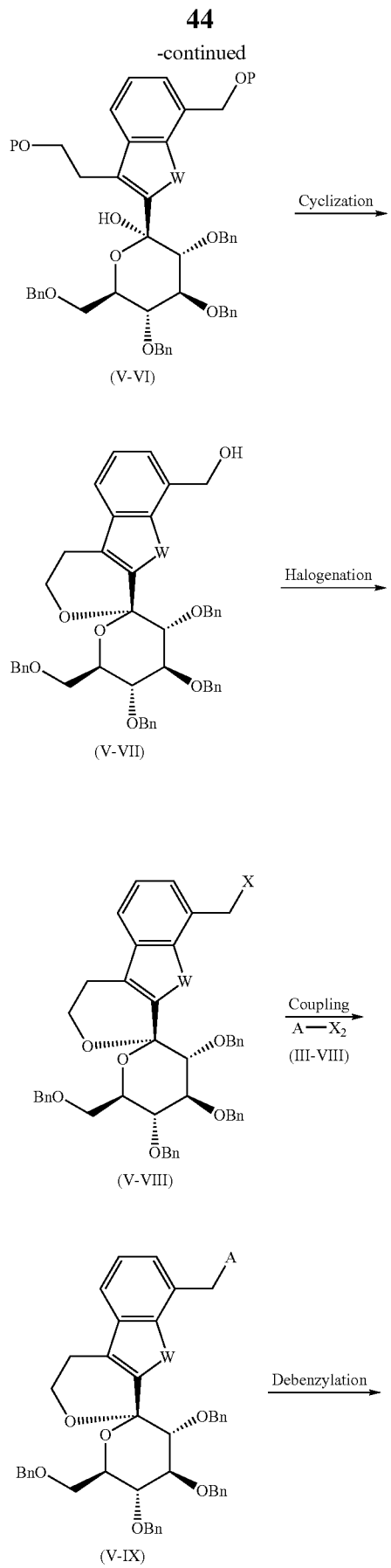
(V-VI) → Cyclization →
(V-VII) → Halogenation →
(III-VIII) → Coupling A—X$_2$ →
(V-VIII)
(V-IX) → Debenzylation →

-continued

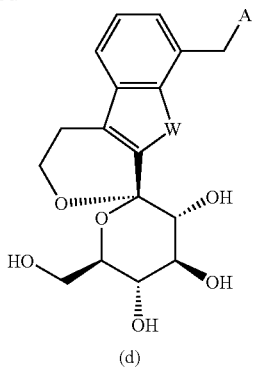

(d)

wherein A is defined in the same manner as described above; W represents a sulfur atom, an oxygen atom or a nitrogen atom; P represents a protecting group of a hydroxyl group; R represents a methyl group or an ethyl group; and $X_2$ represents a boron atom, a silicon atom, a magnesium atom, a zinc atom, a tin atom or the like, each of which have a substituent(s).

The reaction converting Compound (V-I) to Compound (V-II) can be achieved by a reaction with a suitable alkyl halide in the presence of a suitable base in a suitable solvent. Examples of a suitable solvent include THF, dimethoxyethane, diethoxyethane, dioxane, N,N-dimethylformamide, N,N-dimethylacetamide, DMSO, 1,2-dichloroethane, toluene, xylene, acetonitrile and the like, and THF is preferred. Examples of a suitable base include triethylamine, diisopropylethylamine, pyridine, 4-(N,N-dimethylamino)pyridine, N-methylpiperidine, N-methylmorpholine and the like, and triethylamine is preferred. Examples of a suitable alkyl halide include methyl 4-chloroacetoacetate, ethyl 4-chloroacetoacetate and the like. The reaction can generally be carried out at about –20° C. to about 100° C., and preferably at about 0° C. to about 25° C. (room temperature), for about 10 minutes to 12 hours, and preferably for about 2 hours.

The reaction converting Compound (V-II) to Compound (V-III) can be achieved by a reaction with a suitable acid in the presence or absence of a suitable solvent. Examples of a suitable solvent include dichloromethane, 1,2-dichloroethane, nitrobenzene, chlorobenzene and the like. Examples of a suitable acid include polyphosphoric acid, trifluoroacetic acid, methanesulfonic acid, trifluoromethanesulfonic acid, sulfuric acid, phosphoric acid, aluminum trichloride, titanium tetrachloride and the like, and polyphosphoric acid is preferred. The reaction can generally be carried out at about –78° C. to about 100° C., and preferably at about 0° C. to about 80° C., for about 1 hour to about 12 hours, and preferably for about 1 hour.

The reaction converting Compound (V-III) to Compound (V-IV) can be achieved by a reaction with a suitable reducing agent in a suitable solvent. Examples of a suitable solvent include THF, diethyl ether, dimethoxyethane, diethoxyethane, dioxane, dichloromethane, 1,2-dichloroethane, toluene, xylene, methanol, ethanol and the like, and THF is preferred. Examples of a suitable reducing agent include sodium borohydride, lithium borohydride, lithium aluminum hydride, diisopropylaluminum hydride and the like, and lithium aluminum hydride is preferred. The reaction can generally be carried out at about –78° C. to about 50° C., and preferably at about 0° C. to about 25° C. (room temperature), for about 1 minute to 1 hour, and preferably for about 10 minutes.

The reaction converting Compound (V-IV) to Compound (V-V) can be achieved according to the same conditions as those in the above-described reaction in which Compound (I-V) was synthesized from Compound (I-IV).

The reaction converting Compound (V-V) to Compound (V-VI) can be achieved according to the same conditions as those in the above-described reaction in which Compound (I-VII) was synthesized from Compound (I-V).

The reaction converting Compound (V-VI) to Compound (V-VII) can be achieved according to the same conditions as those in the above-described reaction in which Compound (I-VIII) was synthesized from Compound (I-VII).

The reaction converting Compound (V-VII) to Compound (V-VIII) can be achieved according to the same conditions as those in the above-described reaction in which Compound (III-VII) was synthesized from Compound (III-VI).

The reaction converting Compound (V-VIII) to Compound (V-IX) can be achieved according to the same conditions as those in the above-described reaction in which Compound (III-IX) was synthesized from Compound (III-VII).

The reaction converting Compound (V-IX) to the compound wherein ring Ar is represented by Formula (d) can be achieved according to the same conditions as those in the above-described reaction in which the compound wherein ring Ar is represented by Formula (a) was synthesized from Compound (I-XV).

The compound wherein ring Ar is represented by Formula (e) can also be produced according to the methods of the following Schemes 6 to 8.

Scheme 6 (when Y is S):

[Formula 18]

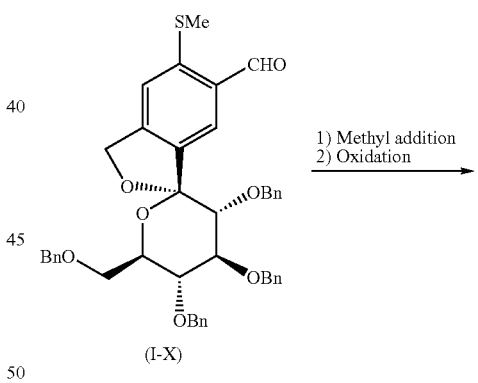

(I-X)

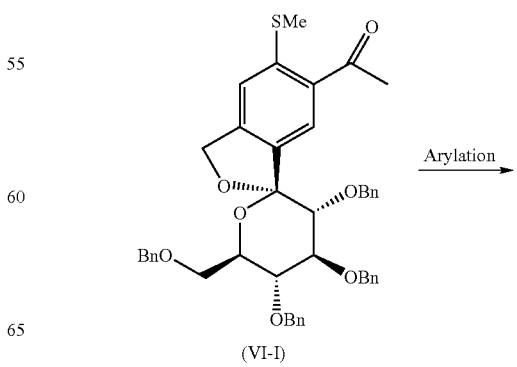

(VI-I)

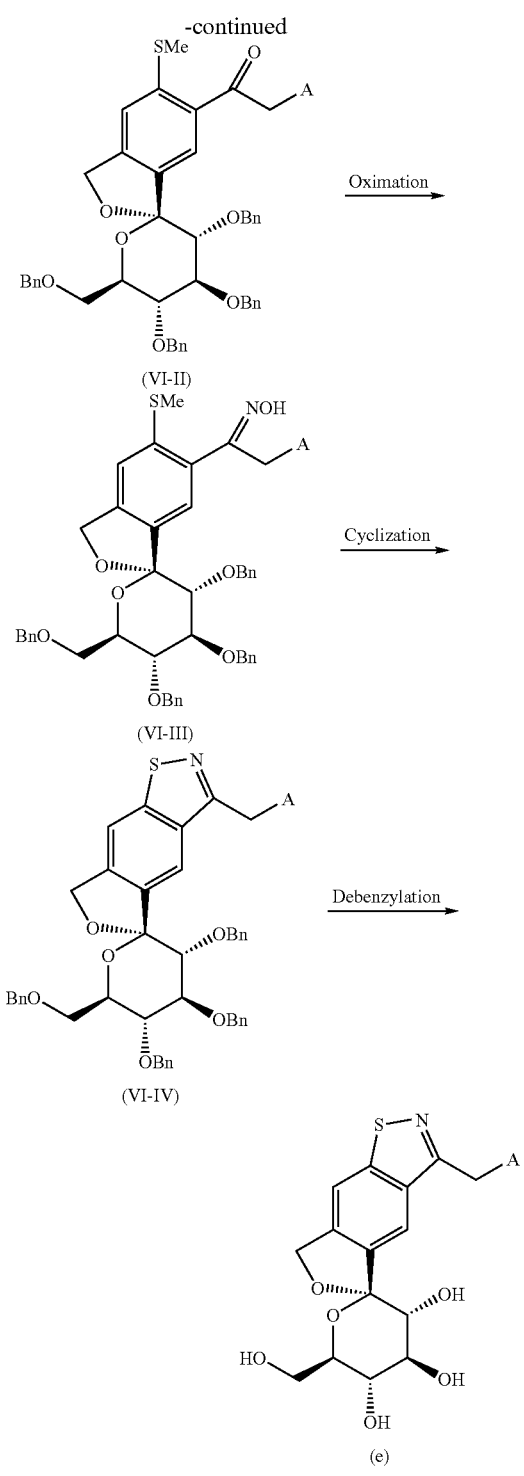

(VI-II)
(VI-III)
(VI-IV)
(e)

wherein A represents an aromatic ring which may have a substituent(s).

The reaction converting Compound (I-X), where X is S and R is a methyl group, to Compound (VI-I) can be achieved by addition of methyl group, and then subjecting the resulting alcohol to an oxidation reaction. The methylation reaction is carried out by a reaction with methylmagnesium bromide or methyllithium in a solvent such as diethyl ether or THF at about −78° C. to about 25° C. (room temperature), and preferably at about 0° C. to about 25° C. (room temperature), for about 10 minutes to about 2 hours. The oxidation reaction is carried out by a reaction with a manganese dioxide-molecular sieve (4 Å) or with an oxidizing agent such as DMSO/oxalyl chloride/triethylamine in a dichloromethane solvent at about −78° C. to about 25° C. (room temperature) for about 30 minutes to about 12 hours.

The reaction converting Compound (VI-I) to Compound (VI-II) can be achieved by a reaction with a suitable halogenated aryl in the presence of a suitable palladium catalyst, a suitable ligand and a suitable base in a suitable solvent. Examples of a suitable solvent include toluene, THF, 1,2-dimethoxyethane, DMSO, DMF and the like, and toluene is preferred. Examples of a suitable palladium catalyst include palladium acetate. Examples of a suitable ligand include 4,5-bis(diphenylphosphino)-9,9-dimethoxyxanthene, tri(tert-butyl)phosphine, tert-butyl(di-1-adamantyl)phosphine and the like. Examples of a suitable base include potassium tert-butoxide, sodium tert-butoxide, potassium phosphate, potassium hexamethyldisilazide and the like. The reaction can generally be carried out at about 60° C. to about 130° C., and preferably at about 80° C. to about 110° C., for about 30 minutes to about 6 hours, and preferably for about 1 to 3 hours.

The reaction converting Compound (VI-II) to Compound (VI-III) can be achieved by a reaction with hydroxylamine hydrochloride in a pyridine solvent. The reaction can be carried out at about 60° C. to about 130° C., and preferably at about 80° C. to about 120° C., for about 30 minutes to about 6 hours, and preferably for about 1 hour to about 3 hours.

The reaction converting Compound (VI-III) to Compound (VI-IV) can be achieved by a reaction with acetic anhydride. The reaction can be carried out at about 60° C. to about 130° C., and preferably at about 80° C. to about 120° C., for about 3 hours to about 24 hours.

The reaction converting Compound (VI-IV) to the compound wherein ring Ar is represented by Formula (e) can be achieved according to the same conditions as those in the above-described reaction in which the compound wherein ring Ar is represented by Formula (a) was synthesized from Compound (I-XV).

Scheme 7 (when Y is O):

[Formula 19]

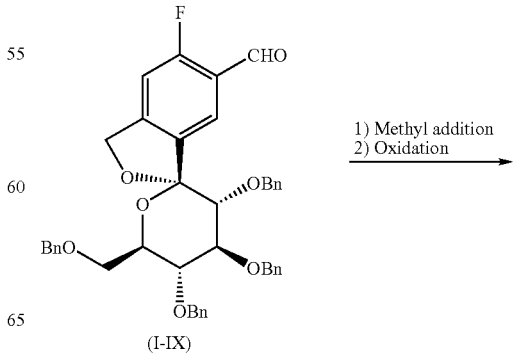

(I-IX)

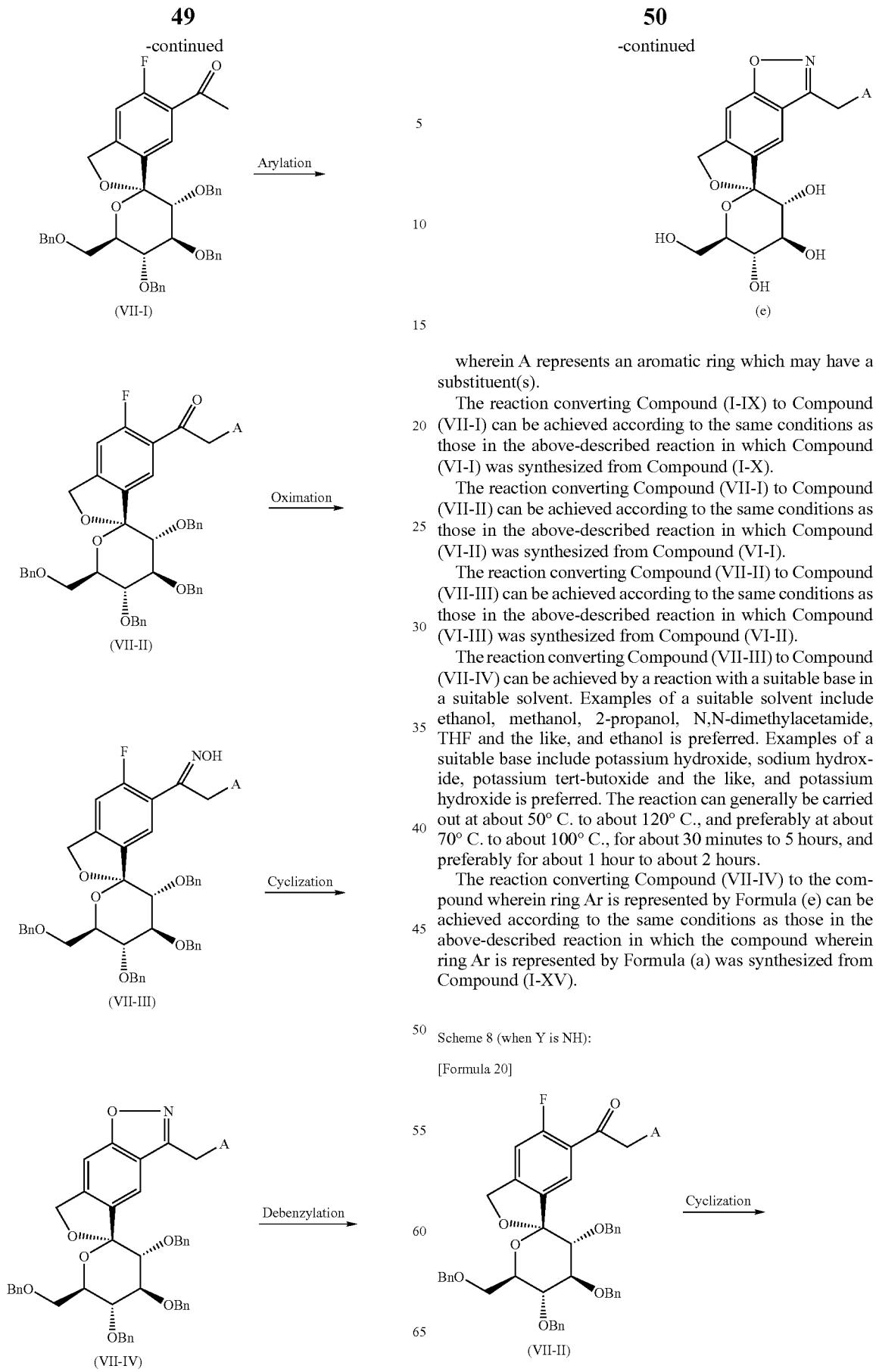

wherein A represents an aromatic ring which may have a substituent(s).

The reaction converting Compound (I-IX) to Compound (VII-I) can be achieved according to the same conditions as those in the above-described reaction in which Compound (VI-I) was synthesized from Compound (I-X).

The reaction converting Compound (VII-I) to Compound (VII-II) can be achieved according to the same conditions as those in the above-described reaction in which Compound (VI-II) was synthesized from Compound (VI-I).

The reaction converting Compound (VII-II) to Compound (VII-III) can be achieved according to the same conditions as those in the above-described reaction in which Compound (VI-III) was synthesized from Compound (VI-II).

The reaction converting Compound (VII-III) to Compound (VII-IV) can be achieved by a reaction with a suitable base in a suitable solvent. Examples of a suitable solvent include ethanol, methanol, 2-propanol, N,N-dimethylacetamide, THF and the like, and ethanol is preferred. Examples of a suitable base include potassium hydroxide, sodium hydroxide, potassium tert-butoxide and the like, and potassium hydroxide is preferred. The reaction can generally be carried out at about 50° C. to about 120° C., and preferably at about 70° C. to about 100° C., for about 30 minutes to 5 hours, and preferably for about 1 hour to about 2 hours.

The reaction converting Compound (VII-IV) to the compound wherein ring Ar is represented by Formula (e) can be achieved according to the same conditions as those in the above-described reaction in which the compound wherein ring Ar is represented by Formula (a) was synthesized from Compound (I-XV).

Scheme 8 (when Y is NH):

[Formula 20]

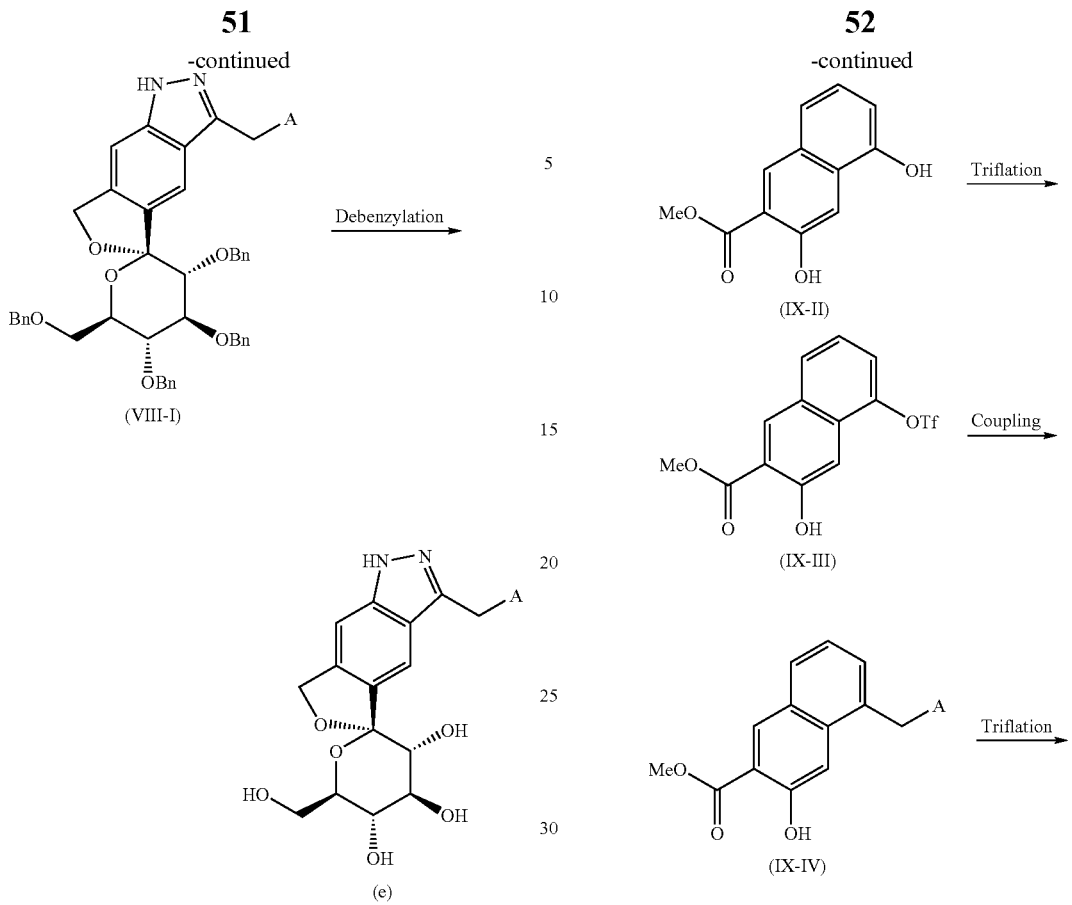

(VIII-I)

(e)

wherein A represents an aromatic ring which may have a substituent(s).

The reaction converting Compound (VII-II) to Compound (VIII-I) can be achieved by a reaction with a hydrazine or hydrazine hydrate in ethylene glycol solvent. The reaction can be carried out at 100° C. to about 180° C., and preferably at about 140° C. to about 170° C., for about 1 hour to about 5 hours.

The reaction converting Compound (VIII-I) to the compound wherein ring Ar is represented by Formula (e) can be achieved according to the same conditions as those in the above-described reaction in which the compound wherein ring Ar is represented by Formula (a) was synthesized from Compound (I-XV).

The compound wherein ring Ar is represented by Formula (c) can be produced according to the following Scheme 9, Scheme 9

[Formula 21]

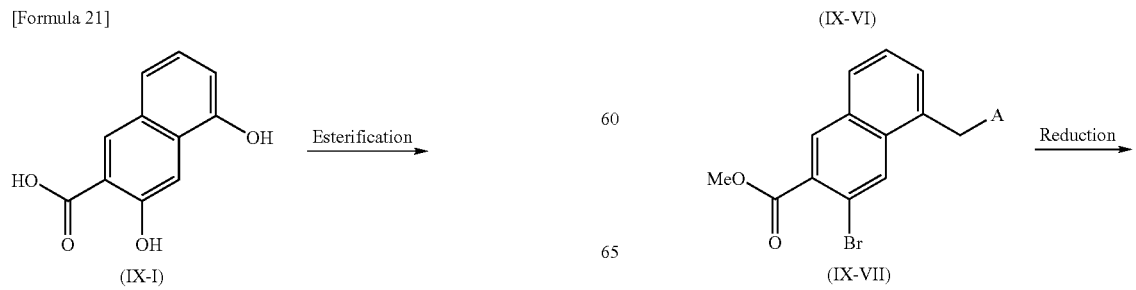

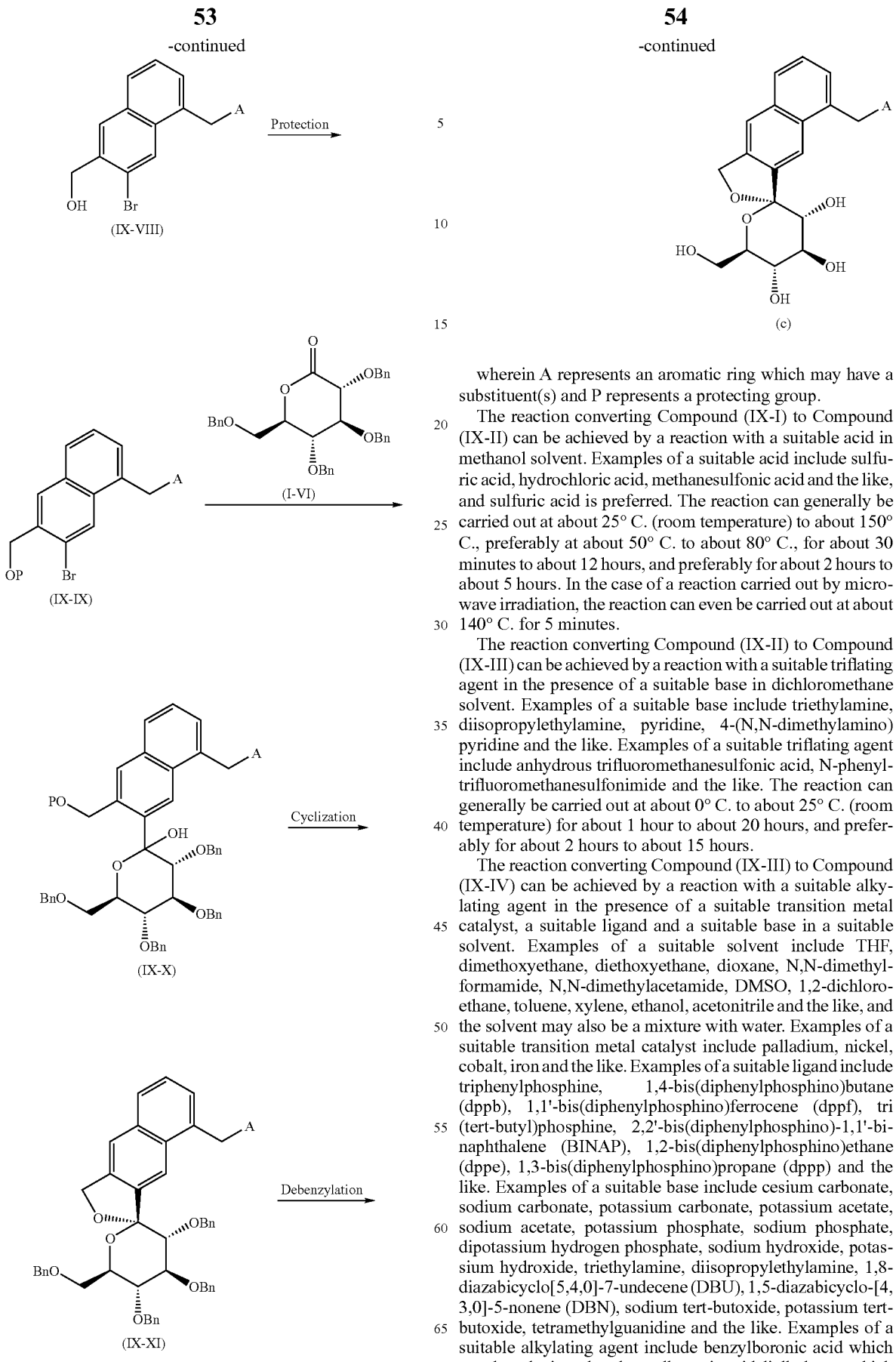

wherein A represents an aromatic ring which may have a substituent(s) and P represents a protecting group.

The reaction converting Compound (IX-I) to Compound (IX-II) can be achieved by a reaction with a suitable acid in methanol solvent. Examples of a suitable acid include sulfuric acid, hydrochloric acid, methanesulfonic acid and the like, and sulfuric acid is preferred. The reaction can generally be carried out at about 25° C. (room temperature) to about 150° C., preferably at about 50° C. to about 80° C., for about 30 minutes to about 12 hours, and preferably for about 2 hours to about 5 hours. In the case of a reaction carried out by microwave irradiation, the reaction can even be carried out at about 140° C. for 5 minutes.

The reaction converting Compound (IX-II) to Compound (IX-III) can be achieved by a reaction with a suitable triflating agent in the presence of a suitable base in dichloromethane solvent. Examples of a suitable base include triethylamine, diisopropylethylamine, pyridine, 4-(N,N-dimethylamino)pyridine and the like. Examples of a suitable triflating agent include anhydrous trifluoromethanesulfonic acid, N-phenyl-trifluoromethanesulfonimide and the like. The reaction can generally be carried out at about 0° C. to about 25° C. (room temperature) for about 1 hour to about 20 hours, and preferably for about 2 hours to about 15 hours.

The reaction converting Compound (IX-III) to Compound (IX-IV) can be achieved by a reaction with a suitable alkylating agent in the presence of a suitable transition metal catalyst, a suitable ligand and a suitable base in a suitable solvent. Examples of a suitable solvent include THF, dimethoxyethane, diethoxyethane, dioxane, N,N-dimethylformamide, N,N-dimethylacetamide, DMSO, 1,2-dichloroethane, toluene, xylene, ethanol, acetonitrile and the like, and the solvent may also be a mixture with water. Examples of a suitable transition metal catalyst include palladium, nickel, cobalt, iron and the like. Examples of a suitable ligand include triphenylphosphine, 1,4-bis(diphenylphosphino)butane (dppb), 1,1'-bis(diphenylphosphino)ferrocene (dppf), tri(tert-butyl)phosphine, 2,2'-bis(diphenylphosphino)-1,1'-binaphthalene (BINAP), 1,2-bis(diphenylphosphino)ethane (dppe), 1,3-bis(diphenylphosphino)propane (dppp) and the like. Examples of a suitable base include cesium carbonate, sodium carbonate, potassium carbonate, potassium acetate, sodium acetate, potassium phosphate, sodium phosphate, dipotassium hydrogen phosphate, sodium hydroxide, potassium hydroxide, triethylamine, diisopropylethylamine, 1,8-diazabicyclo[5,4,0]-7-undecene (DBU), 1,5-diazabicyclo-[4,3,0]-5-nonene (DBN), sodium tert-butoxide, potassium tert-butoxide, tetramethylguanidine and the like. Examples of a suitable alkylating agent include benzylboronic acid which may be substituted, an benzylboronic acid dialkyl ester which may be substituted, an benzylmagnesium halide which may be substituted and the like. The reaction can generally be carried out at about 70° C. to about 150° C., and preferably at about 80° C. to about 100° C., for about 10 minutes to about 24 hours, and preferably for about 1 hour to about 3 hours.

The reaction converting Compound (IX-IV) to Compound (IX-V) can be achieved according to the same conditions as those for the above-described reaction of Compound (IX-III) from Compound (IX-II).

The reaction converting Compound (IX-V) to Compound (IX-VI) can be achieved by a reaction with a suitable pinacolboranating agent in the presence of a palladium catalyst, a suitable ligand and a suitable base in a suitable solvent. Examples of a suitable solvent include dioxane, THF, dimethoxyethane, diethoxyethane, N,N-dimethylformamide, N,N-dimethylacetamide, DMSO, 1,2-dichloroethane, toluene, acetonitrile and the like. Examples of a suitable ligand include triphenylphosphine, 1,1'-bis(diphenylphosphino)ferrocene (dppf), 1,4-bis(diphenylphosphino)butane (dppb), tri(tert-butyl)phosphine, 2,2'-bis(diphenylphosphino)-1,1'-binaphthalene (BINAP), 1,2-bis(diphenylphosphino)ethane (dppe), 1,3-bis(diphenylphosphino)propane (dppp) and the like. Examples of a suitable base include triethylamine, diisopropylethylamine, cesium carbonate, sodium carbonate, potassium carbonate, potassium acetate, sodium acetate, potassium phosphate, sodium phosphate, dipotassium hydrogen phosphate, sodium hydroxide, potassium hydroxide, 1,8-diazabicyclo[5,4,0]-7-undecene (DBU), 1,5-diazabicyclo-[4,3,0]-5-nonene (DBN), sodium tert-butoxide, potassium tert-butoxide, tetramethylguanidine and the like. Examples of a suitable pinacolboranating agent include pinacolborane and bis(pinacolate)diborane. The reaction can generally be carried out at about 70° C. to about 150° C., and preferably at about 80° C. to about 110° C., for about 1 hour to about 12 hours, and preferably for about 2 hours to about 4 hours.

The reaction converting Compound (IX-VI) to Compound (IX-VII) can be achieved by a reaction with a suitable brominating agent in a suitable solvent. Examples of a suitable solvent include methanol-water, ethanol-water, DMF and the like. Examples of a suitable brominating agent include copper (II) bromide. The reaction can generally be carried out at about 50° C. to about 150° C. for about 2 hours to about 20 hours.

The reaction converting Compound (IX-VII) to Compound (IX-VIII) can be achieved by a reaction with a suitable reducing agent in a suitable solvent. Examples of a suitable solvent include THF, toluene, dichloromethane and the like. Examples of a suitable reducing agent include lithium borohydride, lithium aluminum hydride, sodium borohydride, diisopropylaluminum hydride and the like. The reaction can generally be carried out at about −78° C. to about 25° C. (room temperature) for about 10 minutes to about 20 hours.

The reactions from Compound (IX-VIII) to Compound (IX-XI) can be achieved according to the same methods as for the reactions of Compound (II-VIII) from Compound (II-V) of Scheme 2.

The reaction converting Compound (IX-XI) to the compound wherein ring Ar is represented by Formula (c) can be achieved according to the same conditions as those in the above-described reaction in which the compound wherein ring Ar is represented by Formula (a) was synthesized from Compound (I-XV).

The process for producing the compound according to the present invention is not limited to the above-described methods. The compound according to the present invention may also be synthesized by, for example, appropriately combining the steps included in Schemes 1 to 9.

EXAMPLES

The subject matter of the present invention will now be described in more detail with the following examples and test examples. However, the present invention is not limited to such subject matter.

In the following examples, the respective symbols have the following meaning:
NMR: Nuclear magnetic resonance (TMS internal standard);
MS: Mass spectrometry value;
HPLC: High performance liquid chromatography.

The NMR, MS and HPLC were measured using the following instruments.
NMR: JEOL JNM-EX-270 (270 MHz), Brucker ARX300 (300 MHz), Varian Mercury 300 (300 MHz), or JEOL JNM-ECP400 (400 MHz).
MS: LCQ manufactured by Thermo Finnigan, Micromass ZQ manufactured by Waters Corporation or a Q-micro Triple Quadrupole Mass Spectrometer
HPLC: 2690/2996 (detector) manufactured by Waters Corporation Reverse phase preparative HPLC: UniPoint (instrument name) manufactured by Gilson, Inc.
Microwave synthesizer: Initiator™ (instrument name) manufactured by Biotage AB Example 1

(3'R,4'S,5S,5'S,6'R)-3-[(4-ethylphenyl)methyl]-6'-(hydroxymethyl)-3',4',5',6'-tetrahydro-spiro[thieno[2,3,f]isobenzofuran-5(7H),2'-[2H]pyran]-3',4',5'-triol 1) Synthesis of 5-bromo-2-fluoro-4-hydroxymethyl-benzaldehyde

[Formula 22]

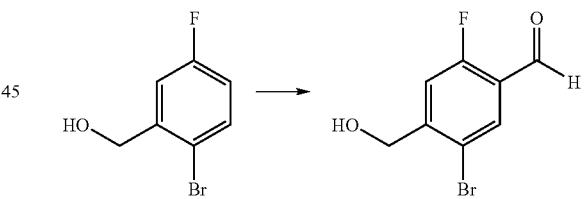

Tetramethylpiperidine (0.68 g, 4.87 mmol) was dissolved in tetrahydrofuran (4.5 mL). To the resultant solution was added n-butyllithium (1.0 M n-hexane solution, 4.88 mL) at 0° C., and the solution was then stirred for 15 minutes. The solution was cooled to −78° C., and a solution of (2-bromo-5-fluorophenyl)-methanol (0.50 g, 2.43 mmol) in tetrahydrofuran (2.5 mL) was added dropwise. The temperature of the solution was raised over 2 hours to −40° C. The solution was again cooled to −78° C., and N,N-dimethylformamide (0.47 mL, 6.07 mmol) was added thereto. The temperature of the solution was raised to room temperature, and the solution was then stirred for 30 minutes. Saturated aqueous ammonium chloride was added, and the resultant mixture was extracted with ethyl acetate. The organic layer was dried over anhydrous sodium sulfate, and then concentrated under reduced pressure, to thereby obtain the titled compound (604.3 mg, quantitative).

$^1$H-NMR (CDCl$_3$) δ: 4.78 (2H, s), 7.46 (1H, d, J=10.6 Hz), 8.01 (1H, d, J=6.2 Hz), 10.29 (1H, s).

2) Synthesis of (2-bromo-5-fluoro-4-hydroxymethyl-phenyl)-methanol

[Formula 23]

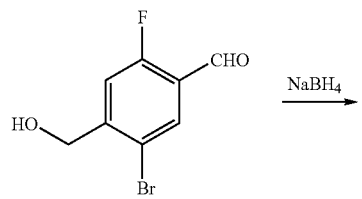

5-Bromo-2-fluoro-4-hydroxymethyl-benzaldehyde (604.3 mg, 2.59 mmol) was dissolved in methanol (5 mL). To the resultant solution was added sodium borohydride (98.1 mg, 2.59 mmol) at 0° C. After stirring for 10 minutes, about 3 mL of methanol was removed by distillation. Water was added to the solution, and the resultant mixture was extracted with ethyl acetate. The organic layer was concentrated under reduced pressure. The resulting residue was purified by silica gel flash column chromatography (developing solution methanol:dichloromethane (3:100)), to thereby obtain the titled compound (247.3 mg, 43%).

$^1$H-NMR (CD$_3$OD) δ: 4.61 (2H, s), 4.64 (2H, s), 7.28 (1H, d, J=11.0 Hz), 7.64 (1H, d, J=7.0 Hz).

3) Synthesis of 1-bromo-4-fluoro-2,5-bis-(1-methoxy-1-methyl-ethoxymethyl)-benzene

[Formula 24]

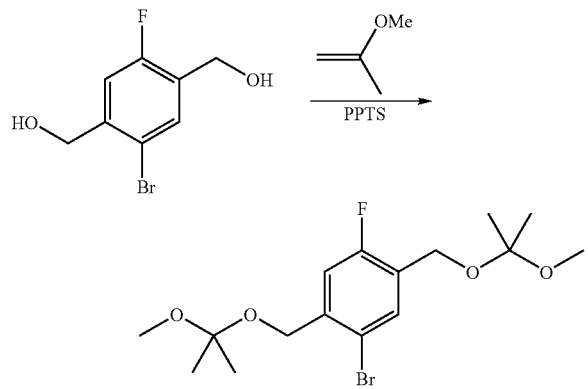

(2-Bromo-5-fluoro-4-hydroxymethylphenyl)-methanol (71.3 mg, 0.303 mmol) was dissolved in tetrahydrofuran (1 mL), and 2-methoxypropene (214.7 mg, 2.97 mmol) was added thereto. The resultant mixture was cooled to 0° C., and then p-toluenesulfonic acid (1.0 mg. 0.0029 mmol) was added thereto. This mixture was stirred for 40 minutes, and then saturated aqueous sodium hydrogen carbonate was added. The resultant mixture was extracted with ethyl acetate. The organic layer was dried over anhydrous sodium sulfate, and then concentrated under reduced pressure, to thereby obtain the titled compound (111.7 mg, 97%).

$^1$H-NMR (CDCl$_3$) δ: 1.43 (6H, s), 1.45 (6H, s), 3.22 (3H, s), 3.24 (3H, s), 4.48 (2H, s), 4.50 (2H, s), 7.26-7.28 (1H, m), 7.59 (1H, d, J=6.6 Hz).

4) Synthesis of (1S,3'R,4'S,5'S,6'R)-3',4',5'-tris-benzyloxy-6'-benzyloxymethyl-5-fluoro-6-hydroxymethyl-3',4',5',6'-tetrahydro-spiro[isobenzofuro-1(3H), 2'-[2H]pyran]

[Formula 25]

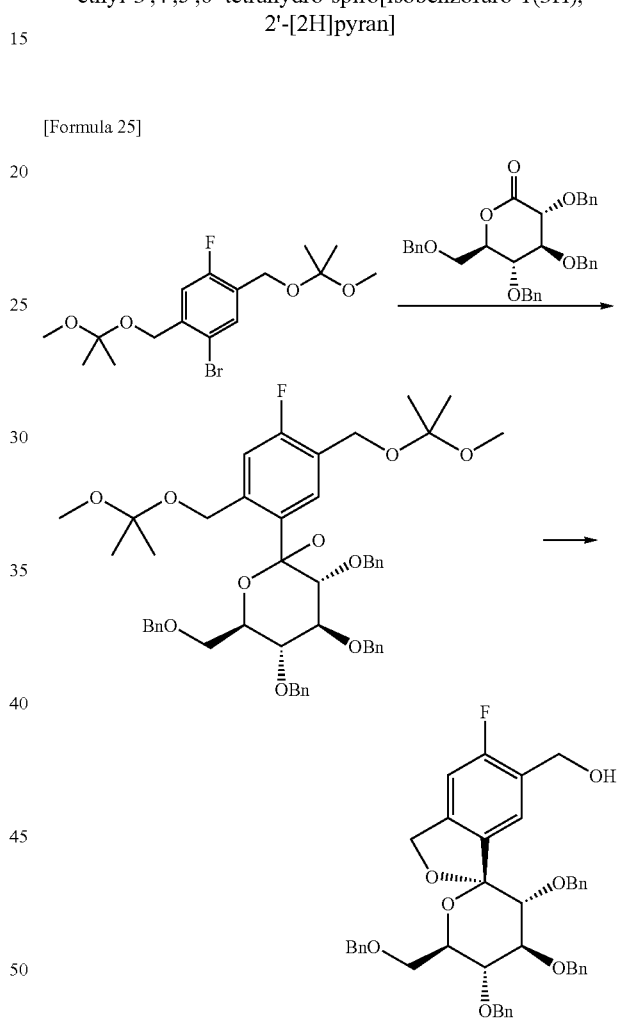

1-Bromo-4-fluoro-2,5-bis-(1-methoxy-1-methyl-ethoxymethyl)-benzene (340.5 mg, 0.850 mmol) was dissolved in tetrahydrofuran (2.5 mL), and the resultant solution was cooled to −78° C. n-Butyllithium (1.0 M n-hexane solution, 1.02 mL) was added dropwise, and the solution was then stirred for 30 minutes. (3R,4S,5R,6R)-3,4,5-tris-benzyloxy-6-benzyloxymethyl-tetrahydro-pyran-2-one (0.642 g, 1.191 mmol) dissolved in tetrahydrofuran (1.0 mL) was added dropwise to the mixture, which was then stirred for 50 minutes. To the resultant mixture was added saturated aqueous ammonium chloride at −78° C., and the resultant mixture was extracted with ethyl acetate. The organic layer was dried over anhydrous sodium sulfate, and then concentrated under reduced pressure, to thereby obtain a crude product (0.968 g).

Next, the obtained crude product (0.968 g) was dissolved in a mixed solvent of methanol (1.0 mL) and tetrahydrofuran (1.5 mL). To the resultant solution was added p-toluenesulfonic acid hydrate (29.3 mg, 0.170 mmol). This solution was stirred for 3 hours at room temperature, and then saturated aqueous sodium hydrogen carbonate was added. The resultant mixture was extracted with ethyl acetate. The organic layer was dried over anhydrous sodium sulfate, and then concentrated under reduced pressure. The resulting residue was purified by silica gel flash column chromatography (developing solution=ethyl acetate:n-hexane (15:100 to 1:4)), to thereby obtain a stereoisomeric mixture of the titled compound (0.29 g).

The obtained stereoisomeric mixture (0.29 g) was again dissolved in a mixed solvent of methanol (0.59 mL) and tetrahydrofuran (0.86 mL), and p-toluenesulfonic acid hydrate (14.7 mg, 0.013 mmol) was added thereto. The resultant mixture was stirred under reflux for 2.5 hours, and then saturated aqueous sodium hydrogen carbonate was added. The resultant mixture was extracted with ethyl acetate. The organic layer was dried over anhydrous sodium sulfate, and then concentrated under reduced pressure, to thereby obtain the titled compound (0.29 g, 50%).

$^1$H-NMR (CDCl$_3$) δ: 3.64 (1H, d, J=9.5 Hz), 3.78 (1H, d, J=11.0, 3.0 Hz), 3.81-3.88 (2H, m), 4.06 (1H, d, J=8.1 Hz), 4.11-4.17 (1H, m), 4.25 (1H, d, J=11.7 Hz), 4.45 (1H, d, J=12.1 Hz), 4.57 (1H, d, J=12.1 Hz), 4.61-4.68 (4H, m), 4.88 (1H, d, J=11.0 Hz), 4.90-4.96 (2H, m), 5.16 (2H, s), 6.81 (2H, d, J=7.0 Hz), 6.93 (1H, d, J=9.5 Hz), 7.11-7.20 (6H, d, J=6.6 Hz), 7.26-7.34 (13H, m).

5) Synthesis of (1S,3'R,4'S,5'S,6'R)-3',4',5'-tris-benzyloxy-6'-benzyloxymethyl-5-fluoro-6-formyl-3',4',5',6'-tetrahydro-spiro[isobenzofuro-1(3H),2'-[2H]pyran]

[Formula 26]

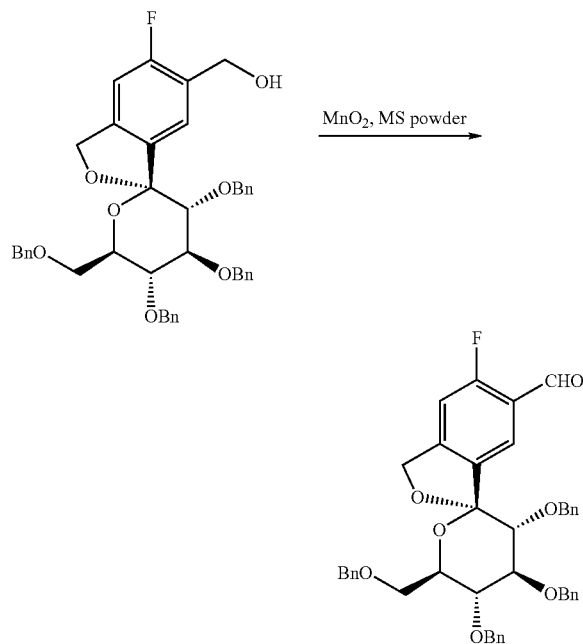

(1S,3'R,4'S,5'S,6'R)-3',4',5'-trisbenzyloxy-6'-benzyloxymethyl-5-fluoro-6-hydroxymethyl-3',4',5',6'-tetrahydrospiro[isobenzofuro-1(3H),2'-[2H]pyran] (1.0 g, 1.47 mmol) was dissolved in dichloromethane (29 mL), and 4 Å molecular sieve powder (3.2 g) was added thereto. The resultant mixture was stirred for 10 minutes, and then manganese dioxide (6.4 g, 73.8 mmol) was added. This resultant mixture was stirred for 1.5 hours, and then filtered. The resultant product was then concentrated under reduced pressure, to thereby obtain the titled compound (781.9 mg, 78%).

$^1$H-NMR (CDCl$_3$) δ: 3.62 (1H, dd, J=10.8, 1.3 Hz), 3.76 (1H, dd, J=11.0, 4.0 Hz), 3.80-3.88 (2H, m), 4.05 (1H, dd, J=10.4, 2.4 Hz), 4.14 (1H, t, J=9.3 Hz), 4.24 (1H, d, J=11.7 Hz), 4.45 (1H, d, J=12.1 Hz), 4.55 (1H, d, J=12.1 Hz), 4.62 (1H, d, J=11.0 Hz), 4.66 (1H, d, J=11.7 Hz), 4.88 (1H, d, J=11.0 Hz), 4.93 (2H, s), 5.19 (2H, s), 6.80 (2H, d, J=6.6 Hz), 7.03 (1H, d, J=9.9 Hz), 7.08-7.14 (3H, m), 7.18-7.20 (2H, m), 7.26-7.34 (13H, m), 7.58 (1H, d, J=5.9 Hz), 10.21 (1H, s).

6) Synthesis of (1S,3'R,4'S,5'S,6'R)-3',4',5'-tris-benzyloxy-6'-benzyloxymethyl-6-formyl-methylthio-3',4',5',6'-tetrahydro-spiro[isobenzofuro-1(3H),2'-[2H]pyran]

[Formula 27]

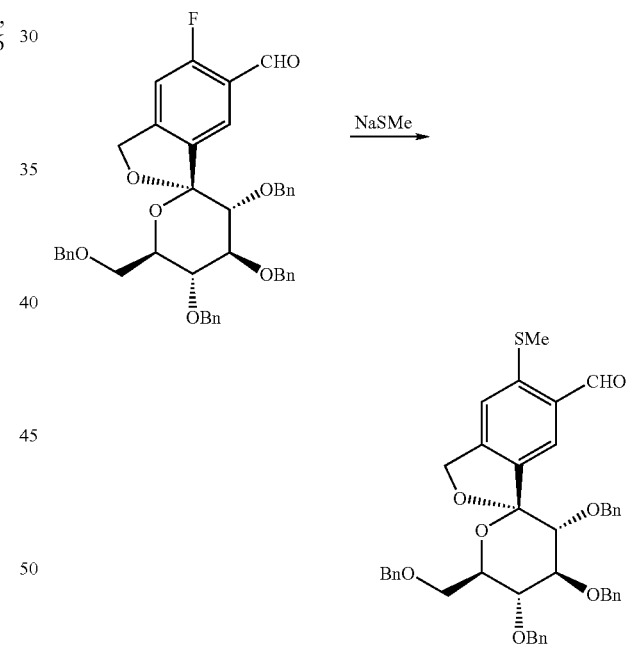

(1S,3'R,4'S,5'S,6'R)-3',4',5'-tris-benzyloxy-6'-benzyloxymethyl-5-fluoro-6-formyl-3',4',5',6'-tetrahydro-spiro[isobenzofuro-1(3H),2'-[2H]pyran] (0.78 g, 1.15 mmol) was dissolved in N,N-dimethylformamide (5.5 mL), and the resultant solution was cooled to 0° C. To the solution was added sodium thiomethoxide (121.8 mg, 1.738 mmol). The resultant solution was stirred for 20 minutes, and then saturated aqueous sodium carbonate was added. The resultant mixture was extracted with diethyl ether. The organic layer was concentrated under reduced pressure, and the resulting residue was purified by silica gel flash column chromatography (developing solution=ethyl acetate:n-hexane (3:10)), to thereby obtain the titled compound (674.9 mg, 82%).

¹H-NMR (CDCl₃) δ: 2.52 (3H, s), 3.63 (1H, d, J=9.5 Hz), 3.78 (1H, dd, J=11.2, 3.8 Hz), 3.82-3.90 (2H, m), 4.07 (1H, d, J=8.4 Hz), 4.10-4.19 (1H, m), 4.31 (1H, d, J=11.7 Hz), 4.46 (1H, d, J=12.1 Hz), 4.56 (1H, d, J=12.1 Hz), 4.62-4.67 (2H, m), 4.90 (1H, d, J=10.6 Hz), 4.96 (2H, s), 5.21 (2H, s), 6.81 (2H, d, J=7.0 Hz), 7.05-7.22 (7H, m), 7.27-7.38 (13H, m), 10.00 (1H, s).

7) Synthesis of (1S,3'R,4'S,5'S,6'R)-3',4',5'-tris-benzyloxy-6'-benzyloxymethyl-6-ethynyl-5-methylthio-3',4',5',6'-tetrahydro-spiro[isobenzofuro-1(3H),2'-[2H]pyran]

[Formula 28]

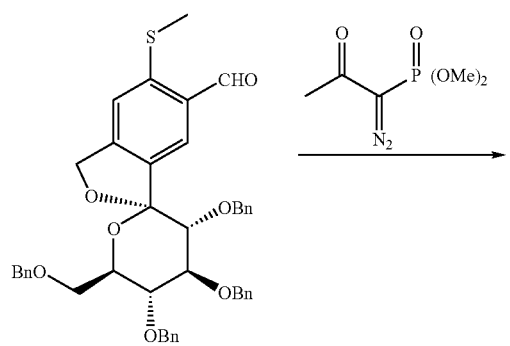

(1S,3'R,4'S,5'S,6'R)-3',4',5'-tris-benzyloxy-6'-benzyloxymethyl-6-formyl-methylthio-3',4',5',6'-tetrahydro-spiro[isobenzofuro-1(3H),2'-[2H]pyran] (506.1 mg, 0.72 mmol) was dissolved in a mixed solvent of methanol (7.5 mL) and tetrahydrofuran (1.3 mL). To the resultant solution were added potassium carbonate (199.0 mg, 1.44 mmol) and dimethyl(1-diazo-2-oxopropyl)phosphonate (179.8 mg, 0.936 mmol), and then the solution was stirred for 12 hours at room temperature under a nitrogen stream. To the resultant mixture was added saturated aqueous sodium carbonate, and extracted with diethyl ether. The organic layer was dried over anhydrous sodium sulfate, and then concentrated under reduced pressure. The resulting residue was purified by silica gel flash column chromatography (developing solution=ethyl acetate:n-hexane (1:5 to 1:4)), to thereby obtain the titled compound (412.9 mg, 77%).

¹H-NMR (CDCl₃) δ: 2.52 (3H, s), 3.47 (1H, s), 3.63 (1H, d, J=10.3 Hz), 3.76-3.85 (3H, m), 4.05 (1H, d, J=8.4 Hz), 4.12 (1H, t, J=9.3 Hz), 4.23 (1H, d, J=11.0 Hz), 4.46 (1H, d, J=12.1 Hz), 4.55-4.64 (3H, m), 4.88 (1H, d, J=11.0 Hz), 4.90 (1H, d, J=11.0 Hz), 4.94 (1H, d, J=11.0 Hz), 5.16 (2H, s), 6.84 (2H, d, J=7.0 Hz), 7.03 (1H, s), 7.12-7.21 (6H, m), 7.27-7.33 (13H, m).

8) Synthesis of (3'R,4'S,5S,5'S,6'R)-3',4',5'-tris-benzyloxy-6'-benzyloxymethyl-3-iodo-3',4',5',6'-tetrahydro-spiro[thieno[2,3,f]isobenzofuran-5(7H),2'-[2H]pyran]

[Formula 29]

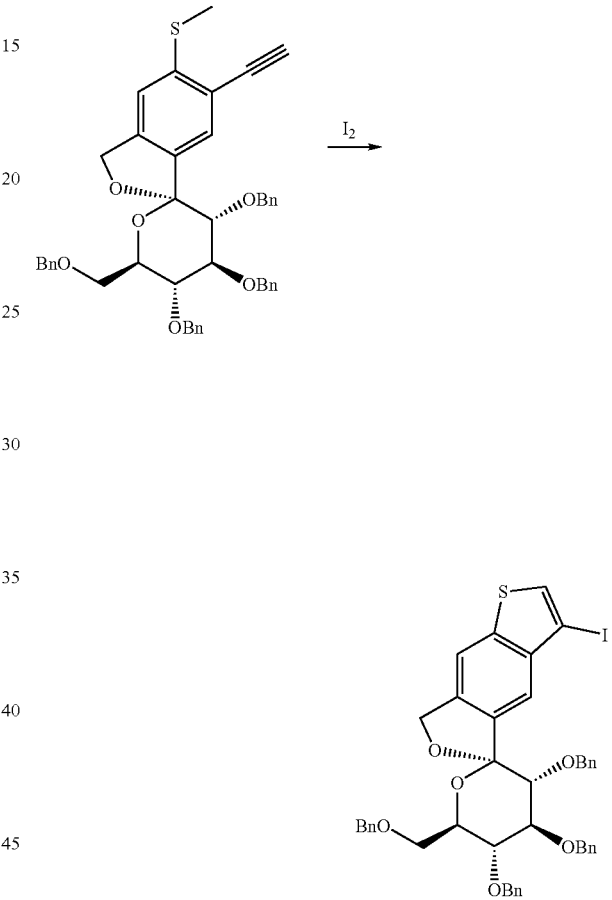

(1S,3'R,4'S,5'S,6'R)-3',4',5'-tris-benzyloxy-6'-benzyloxymethyl-6-ethynyl-5-methylthio-3',4',5',6'-tetrahydrospiro[isobenzofuro-1(3H),2'-[2H]pyran] (0.15 g, 0.214 mmol) was dissolved in dichloromethane (2.6 mL). To the resultant solution was added iodine (0.10 g, 0.429 mmol) dissolved in dichloromethane (2.0 mL), and then the mixture was stirred for 15 minutes at room temperature. Aqueous sodium thiosulfate pentahydrate was added thereto, and the resultant mixture was extracted with diethyl ether. The organic layer was dried over anhydrous sodium sulfate, and then concentrated under reduced pressure. The resulting residue was purified by silica gel flash column chromatography (developing solution=ethyl acetate:n-hexane (1:5)), to thereby obtain the titled compound (38.7 mg, 22%).

¹H-NMR (CDCl₃) δ: 3.67 (1H, d, J=11.0 Hz), 3.83 (1H, dd, J=11.0, 3.7 Hz), 3.92 (1H, t, J=9.5 Hz), 4.03 (1H, d, J=9.5 Hz), 4.10-4.21 (3H, m), 4.48 (1H, d, J=12.1 Hz), 4.56-4.67 (3H, m), 4.91 (1H, d, J=11.0 Hz), 4.95 (1H, d, J=11.2 Hz), 4.97 (1H, d. J=11.2 Hz), 5.32 (2H, s), 6.69 (2H, d, J=7.0 Hz), 6.93-7.02 (3H, m), 7.20-7.37 (15H, m), 7.55 (1H, s), 7.60 (1H, s), 7.68 (1H, s).

9) Synthesis of (3'R,4'S,5S,5'S,6'R)-3',4',5'-tris-benzyloxy-6'-benzyloxymethyl-3-[(4-ethylphenyl)methyl]-3',4',5',6'-tetrahydro-spiro[thieno[2,3,f]isobenzofuran-5(7H),2'-[2H]pyran]

[Formula 30]

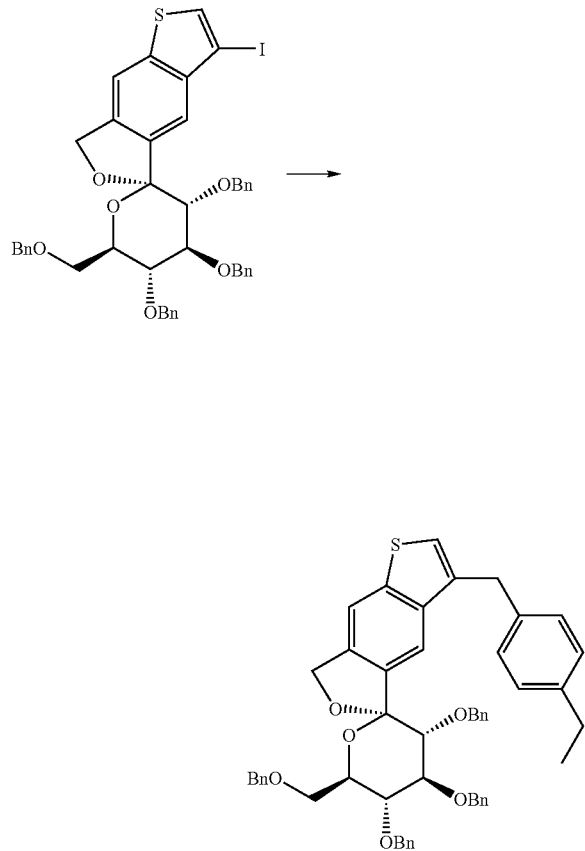

(3'R,4'S,5S,5'S,6'R)-3',4',5'-tris-benzyloxy-6'-benzyloxymethyl-3-iodo-3',4',5',6'-tetrahydro-spiro[thieno[2,3,f]isobenzofuran-5(7H),2'-[2H]pyran] (0.05 g, 0.061 mmol), potassium carbonate (25.5 mg, 0.184 mmol), silver oxide (35.6 mg, 0.154 mmol) and diphenylphosphino ferrocene palladium dichloride (5.1 mg, 0.006 mmol) were dissolved in 1,4-dioxane (0.308 mL). To the resultant solution was added 2-(4-ethyl-benzyl)-4,4,5,5-tetramethyl-[1,3,2]dioxaborane (18.2 mg, 0.073 mmol), and then the solution was stirred for 3 hours at 100° C. under a nitrogen stream. The reaction solution was filtered, and the resultant product was then concentrated under reduced pressure. The resulting residue was purified by silica gel flash column chromatography (developing solution=ethyl acetate:n-hexane (14:100)), to thereby obtain the titled compound (39.4 mg, 79%).

$^1$H-NMR (CDCl$_3$) δ: 1.13 (3H, t, J=7.7 Hz), 2.49 (2H, q, J=7.7 Hz), 3.67 (1H, dd, J=11.0, 1.5 Hz), 3.82 (1H, dd, J=11.0, 3.7 Hz), 3.87-3.91 (3H, m), 4.10-4.19 (4H, m), 4.39 (1H, d, J=11.0 Hz), 4.46 (1H, d, J=12.1 Hz), 4.59 (1H, d, J=12.1 Hz), 4.65 (1H, d, J=11.0 Hz), 4.88-4.95 (3H, m), 5.26 (1H, d, J=12.6 Hz), 5.31 (1H, d, J=12.6 Hz), 6.60 (2H, d, J=7.3 Hz), 6.98-7.01 (4H, m), 7.06 (1H, d, J=7.3 Hz), 7.11 (2H, d, J=8.1 Hz), 7.23-7.33 (16H, m), 7.57 (1H, s), 7.72 (1H, s).

10) Synthesis of (3'R,4'S,5S,5'S,6'R)-3-[(4-ethylphenyl)methyl]-6'-hydroxymethyl-3',4',5',6'-tetrahydro-spiro[thieno[2,3,f]isobenzofuran-5(7H),2'-[2H]pyran]-3',4',5'-triol

[Formula 31]

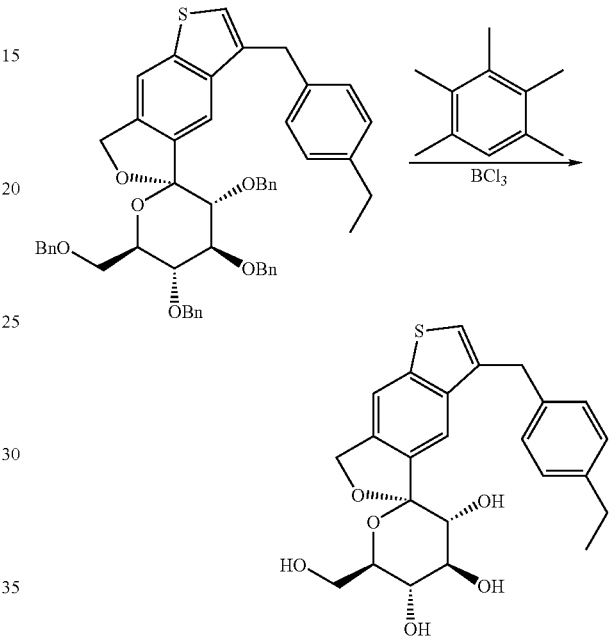

(3'R,4'S,5S,5'S,6'R)-3',4',5'-tris-benzyloxy-6'-benzyloxymethyl-3-[(4-ethylphenyl)methyl]-3',4',5',6'-tetrahydro-spiro[thieno[2,3,f]isobenzofuran-5(7H),2'-[2H]pyran] (34.1 mg, 0.042 mmol) was dissolved in dichloromethane (1.4 mL). To the resultant solution was added pentamethylbenzene (94.3 mg, 0.636 mmol), and then the solution was cooled to −78° C. Boron trichloride (1.0 M dichloromethane solution, 0.212 mL) was added dropwise, and the solution was stirred for 3 hours. To the solution was then added methanol (1.5 mL) to stop the reaction. The temperature of the solution was raised to room temperature. The reaction solution was concentrated under reduced pressure. The resulting residue was purified by silica gel flash column chromatography (developing solution=ethyl acetate:n-hexane (2:25)), and the resultant product was then further isolated and purified by reverse phase HPLC (developing solution=acetonitrile:water (35:65 to 100:0)), to thereby obtain the titled compound (13.3 mg, 70%).

$^1$H-NMR (CD$_3$OD) δ: 1.21 (3H, t, J=7.7 Hz), 2.61 (2H, q, J=7.7 Hz), 3.51 (1H, dd, J=9.2, 4.6 Hz), 3.68 (1H, dd, J=11.9, 5.7 Hz), 3.78-3.88 (4H, m), 4.17 (2H, s), 5.20 (1H, d, J=12.6 Hz), 5.27 (1H, d, J=12.6 Hz), 7.09 (1H, s), 7.13 (2H, d, J=8.1 Hz), 7.19 (2H, d, J=8.1 Hz), 7.78 (1H, s), 7.78 (1H, s).

MS (ESI$^+$): 443 [M+1]$^+$.

HPLC retention time: 18.5 minutes

<HPLC Measurement Conditions>

Column: YMC-Pack ODS-A 6.0×150 mm, 5 μm

Mobile phase: Eluted under gradient from 10 mM AcONH$_4$/MeOH (5%)+10 mM AcONH$_4$/H$_2$O (95%) to 10 mM AcONH₄/MeOH (100%) over 20 minutes, and then under the same conditions (10 mM AcONH₄/MeOH (100%)) for 5 minutes.

Flow rate: 1.5 mL/min

Column temperature: Room temperature

Detection conditions: Total plot over all wavelengths from 230 to 400 nm

Example 2

(3'R,4'S,5'S,6'R,7S)-1-[(4-ethylphenyl)methyl]-6'-hydroxymethyl-3',4,5',6'-tetrahydro-spiro[furo[3,4,f]indole-7(5H),2'-[2H]pyran]-3',4',5'-triol 1) Synthesis of (3-bromo-4-methylphenyl)-(2,2-diethoxyethyl)-amine

[Formula 32]

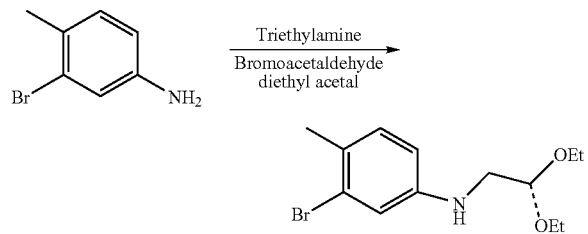

Under a nitrogen stream, a mixture of 3-bromo-4-methylphenylamine (4.94 g, 26.55 mmol), bromoacetaldehyde diethyl acetal (6.80 g, 34.50 mmol), triethylamine (5.37 mL, 38.53 mmol) and ethanol (10.3 mL) was stirred for 2 hours at 150° C. using a microwave apparatus. The resultant solution was cooled to room temperature, and then water was added thereto. The resultant mixture was extracted with dichloromethane. The organic layer was dried over anhydrous magnesium sulfate, and then concentrated under reduced pressure. The resulting residue was purified by silica gel flash column chromatography (developing solution=ethyl acetate:n-hexane (1:10)), to thereby obtain the titled compound (6.43 g, 80%).

¹H-NMR (CDCl₃) δ: 1.17-1.28 (6H, m), 2.27 (3H, s), 3.18-3.77 (6H, m), 3.80 (1H, bs), 4.61-4.68 (1H, m), 6.49 (1H, dd, J=2.47, 8.23 Hz), 6.83 (1H, d, J=2.47 Hz), 6.99 (1H, d, J=8.23 Hz).

2) Synthesis of N-(3-bromo-4-methylphenyl)-N-(2,2-diethoxyethyl)benzenesulfonamide

[Formula 33]

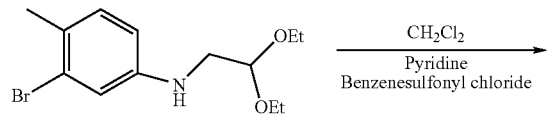

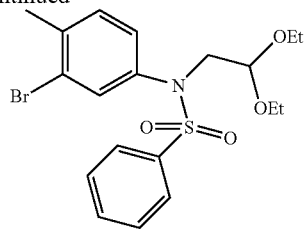

Under a nitrogen stream, benzenesulfonyl chloride (3.12 mL g, 24.48 mmol) was added dropwise under ice cooling to a mixture of (3-bromo-4-methylphenyl)-(2,2-diethoxyethyl)-amine (4.91 g, 16.25 mmol), pyridine (10.1 mL, 124.88 mmol) and dichloromethane (41 mL), and the resultant mixture was then stirred at the same temperature for 1 hour. After stirring at room temperature for 2 hours, the reaction mixture was added to saturated aqueous sodium hydrogen carbonate. The resultant mixture was extracted with dichloromethane. The organic layer was washed with 5% aqueous hydrochloric acid and dried (anhydrous potassium carbonate). Solvent was then removed by distillation under reduced pressure. The resulting residue was purified by silica gel column chromatography (developing solution=ethyl acetate:n-hexane (1:4)), to thereby obtain the titled compound (5.94 g, 83%).

¹H-NMR (CDCl₃) δ: 1.11-1.15 (6H, m), 2.37 (3H, s), 3.46-3.66 (6H, m), 4.59-4.63 (1H, m), 6.90 (1H, dd, J=2.20, 8.23 Hz), 7.13 (1H, d, J=8.23 Hz), 7.19 (1H, d, J=2.20 Hz), 7.46-7.61 (5H, m).

3) Synthesis of 1-benzenesulfonyl-6-bromo-5-methyl-1H-indole

[Formula 34]

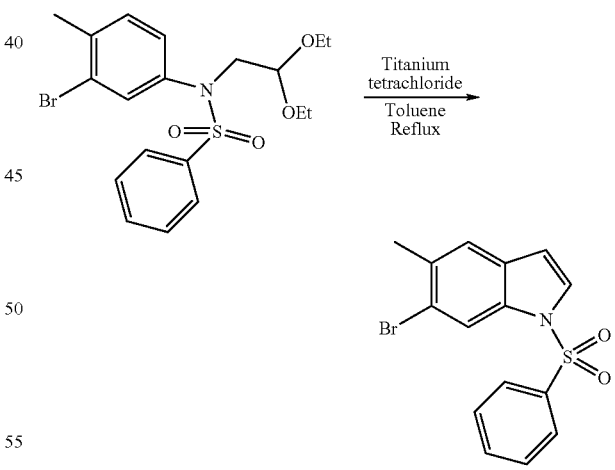

Under a nitrogen stream, a solution of N-(3-bromo-4-methylphenyl)-N-(2,2-diethoxyethyl)benzenesulfonamide (5.16 g, 11.66 mmol) in toluene (118 mL) and a solution of titanium tetrachloride (1.92 mL, 17.51 mmol) in toluene (118 mL) were simultaneously added dropwise over 25 minutes to toluene (315 mL) which was heated to reflux. After heating to reflux for 1 hour, the reaction mixture was cooled to room temperature and then saturated aqueous sodium hydrogen carbonate was added thereto. The resultant mixture was extracted with ethyl acetate. After drying (anhydrous potassium carbonate), solvent was removed by distillation under reduced pressure. The resulting residue was purified by silica gel column chromatography (developing solution=ethyl acetate:n-hexane (1:4)), to thereby obtain the titled compound (2.04 g, 50%).

¹H-NMR (CDCl₃) δ: 2.43 (3H, d, J=0.55 Hz), 6.55 (1H, dd, J=0.82, 3.84 Hz), 7.36 (1H, s), 7.41-7.57 (4H, m), 7.84-7.87 (2H, m), 8.20 (1H, s).

4) Synthesis of 1-benzenesulfonyl-6-bromo-5-bromomethyl-1H-indole

[Formula 35]

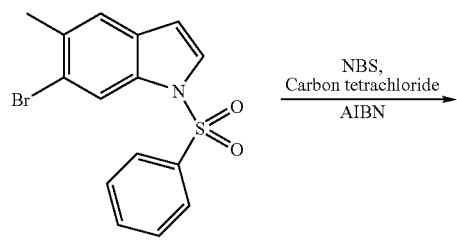

Under a nitrogen stream, a solution of 1-benzenesulfonyl-6-bromo-5-methyl-1H-indole (40 mg, 0.11 mmol), N-bromosuccinimide (NBS) (22 mg, 0.12 mmol) and 2,2'-azobis(isobutyronitrile) (AIBN) (1 mg, 0.01 mmol) in carbon tetrachloride (0.5 mL) was heated to reflux for 1 hour. The reaction mixture was cooled to room temperature, and then purified by silica gel column chromatography (developing solution=ethyl acetate:n-hexane (1:9)), to thereby obtain the titled compound (22 mg, 45%).

¹H-NMR (CDCl₃) δ: 4.69 (2H, s), 6.61 (1H, dd, J=0.82, 3.57 Hz), 7.46-7.62 (5H, m), 7.86-7.89 (2H, m), 8.25 (1H, s).

5) Synthesis of 1-benzenesulfonyl-6-bromo-1H-indol-5-ylmethyl acetate

[Formula 36]

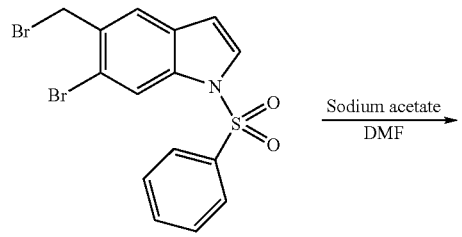

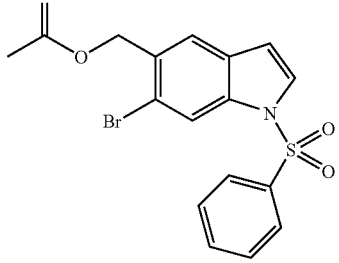

Under a nitrogen stream, to a solution of 1-benzenesulfonyl-6-bromo-5-bromomethyl-1H-indole (14 mg, 0.03 mmol) in DMF (0.2 mL) was added sodium acetate (4 mg, 0.05 mmol), and the resultant mixture was then stirred for 2 hours at 80° C. The reaction mixture was cooled to room temperature, and then purified by silica gel column chromatography (developing solution=ethyl acetate:n-hexane (2:5)), to thereby obtain the titled compound (11 mg, 85%).

¹H-NMR (CDCl₃) δ: 2.12 (3H, s), 5.23 (2H, s), 6.62-6.63 (1H, m), 7.44-7.59 (5H, m), 7.85-7.88 (2H, m), 8.25 (1H, s).

6) Synthesis of (1-benzenesulfonyl-6-bromo-1H-indol-5-yl)methanol

[Formula 37]

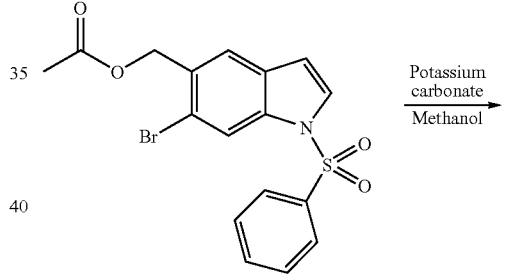

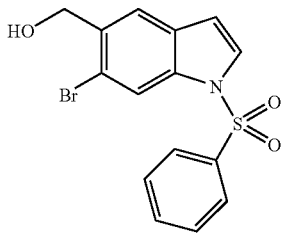

Under a nitrogen stream, a mixture of 1-benzenesulfonyl-6-bromo-1H-indol-5-ylmethyl acetate (257 mg, 0.63 mmol), potassium carbonate (15 mg, 0.11 mmol) and methanol (4 mL) was stirred for 1 hour at room temperature. To the resultant mixture was added 2 N hydrochloric acid (0.11 mL), and solvent was then removed by distillation under reduced pressure. The resulting residue was purified by silica gel flash column chromatography (developing solution=ethyl acetate: n-hexane (2:1)), to thereby obtain the titled compound (225 mg, 97%).

$^1$H-NMR (CDCl$_3$) δ: 4.78 (2H, s), 6.63 (1H, dd. J=0.82, 3.84 Hz), 7.43-7.58 (4H, m), 7.62 (1H, s), 7.84-7.87 (2H, m), 8.22 (1H, s).

7) Synthesis of 1-benzenesulfonyl-6-bromo-5-(1-methoxy-1-methyl-ethoxymethyl)-1H-indole

[Formula 38]

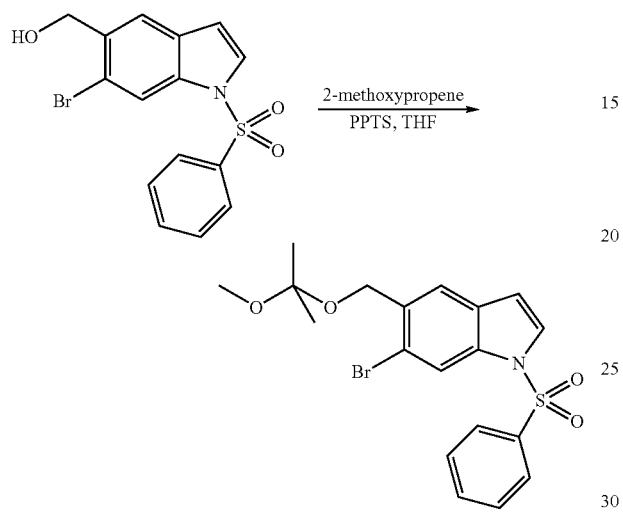

Under a nitrogen stream, to a solution of (1-benzenesulfonyl-6-bromo-1H-indol-5-yl)methanol (234 mg, 0.64 mmol) and pyridinium p-toluenesulfonate (4 mg, 0.02 mmol) in THF (0.7 mL) was added 2-methoxypropene (92 μL, 0.96 mmol) under ice cooling, and the resultant mixture was stirred at the same temperature for 1 hour. To the reaction mixture was added saturated aqueous potassium carbonate. The resultant mixture was then twice extracted with ethyl acetate. The organic layer was dried (anhydrous magnesium sulfate). Solvent was then removed by distillation under reduced pressure, to thereby obtain the titled compound (277 mg, 99%).

$^1$H-NMR (CDCl$_3$) δ: 1.46 (6H, s), 3.23 (3H, s), 4.57 (2H, s), 6.62 (1H, d, J=3.84 Hz), 7.42-7.55 (4H, m), 7.68 (1H, s), 7.84-7.87 (2H, m), 8.21 (1H, s).

8) Synthesis of (3'R,4'S,5'S,6'R,7S)-1-benzenesulfonyl-3',4',5'-tris-benzyloxy-6'-benzyloxymethyl-3',4',5',6'-tetrahydro-spiro[furo[3,4,f]indole-7(5H),2'-[2H]pyran]

[Formula 39]

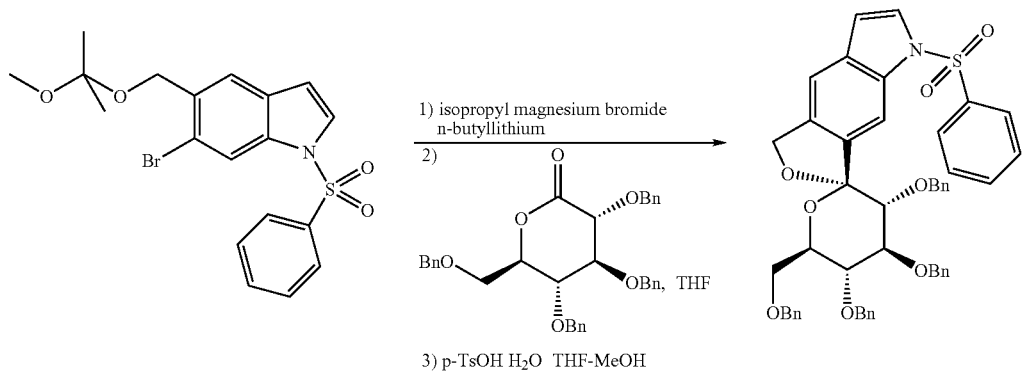

Under a nitrogen stream, to THF (1.4 mL) were added a solution of isopropyl magnesium bromide in THF (0.65 M, 0.78 mL, 0.51 mmol) and a solution of n-butyllithium in n-hexane (1.58 M, 645 μL, 1.02 mmol) under ice cooling, and the resultant solution was stirred for 30 minutes. The solution was then cooled to −78° C., and a solution of 1-benzenesulfonyl-6-bromo-5-(1-methoxy-1-methyl-ethoxymethyl)-1H-indole (186 mg, 0.42 mmol) in THF (0.75 mL) was added dropwise thereto. The resultant mixture was then stirred for 1 hour. A solution of 3,4,5-tris-benzyloxy-6-(benzyloxymethyl)-tetrahydro-pyran-2-one (686 mg, 1.27 mmol) in THF (0.75 mL) was added dropwise to the reaction mixture at the same temperature. The resultant mixture was stirred for 1 hour at −20° C., and then saturated aqueous ammonium chloride was added. The resultant mixture was extracted with dichloromethane, and the organic layer was dried (anhydrous magnesium sulfate). Solvent was then removed by distillation under reduced pressure. To the resulting residue was added THF (1.6 mL), methanol (1 mL) and p-toluenesulfonic acid (47 mg, 0.25 mmol), and the resultant mixture was stirred for 2 hours at room temperature. Solvent was then removed by distillation under reduced pressure, and the resulting residue was purified by silica gel flash column chromatography (developing solution=ethyl acetate:n-hexane (1:1)), to thereby obtain the titled compound (92 mg, 27%).

$^1$H-NMR (CDCl$_3$) δ: 3.67 (1H, dd, J=1.92, 11.25 Hz), 3.82-4.15 (6H, m), 4.46-4.71 (4H, m), 4.91-4.94 (3H, m), 5.18-5.27 (2H, m), 6.50-6.53 (2H, m), 6.69-6.70 (1H, m), 6.95-7.38 (22H, m), 7.63 (1H, d, J=3.57 Hz), 7.71-7.75 (2H, m), 7.96 (1H, s).

9) Synthesis of (3'R,4'S,5'S,6'R,7S)-3',4',5'-tris-benzyloxy-6'-benzyloxymethyl-3',4',5',6'-tetrahydro-spiro[furo[3,4,f]indole-7(1H,5H),2'-[2H]pyran]

[Formula 40]

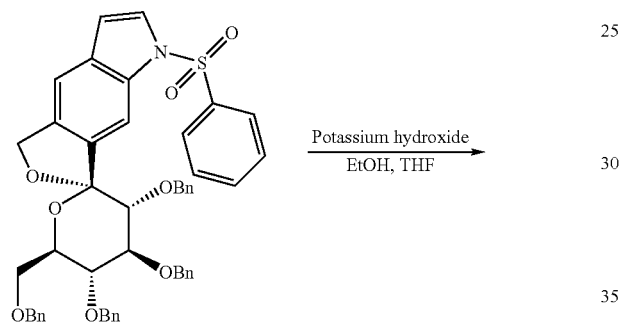

Under a nitrogen stream, to a solution of (3'R,4'S,5'S,6'R,7S)-1-benzenesulfonyl-3',4',5'-tris-benzyloxy-6'-benzyloxymethyl-3',4',5',6'-tetrahydro-spiro[furo[3,4,f]indole-7(5H),2'-[2H]pyran] (0.10 g, 0.13 mmol) in ethanol (2.1 mL) and THF (0.6 mL) was added potassium hydroxide (0.14 g, 2.48 mmol), and the resultant mixture was stirred for 3 hours at 50° C. Solvent was then removed by distillation under reduced pressure, and the resulting residue was purified by silica gel flash column chromatography (developing solution=ethyl acetate:n-hexane (2:5)), to thereby obtain the titled compound (42 mg, 51%).

$^1$H-NMR (CDCl$_3$) δ: 3.68 (1H, dd, J=1.92, 10.98 Hz), 3.82-3.99 (3H, m), 4.09-4.22 (4H, m), 4.43-4.69 (4H, m), 4.89-4.98 (3H, m), 5.30 (1H, d, J=1.10 Hz), 6.52-6.54 (1H, m), 6.71-6.73 (2H, m), 6.97-7.08 (3H, m), 7.18-7.38 (16H, m), 7.46 (1H, s), 8.13 (1H, s).

10) Synthesis of (3'R,4'S,5'S,6'R,7S)-3',4',5'-tris-benzyloxy-6'-benzyloxymethyl-1-[(4-ethylphenyl)methyl]-3',4',5',6'-tetrahydro-spiro[furo[3,4,f]indole-7(5H),2'-[2H]pyran]

[Formula 41]

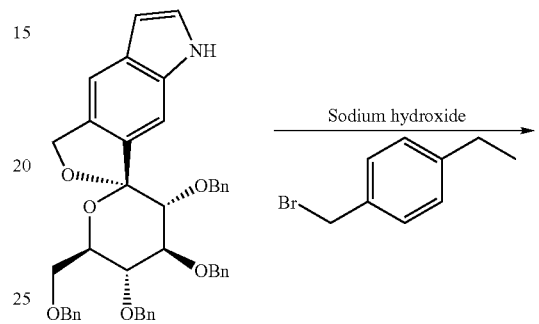

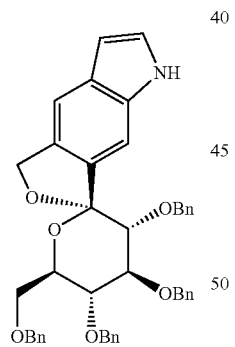

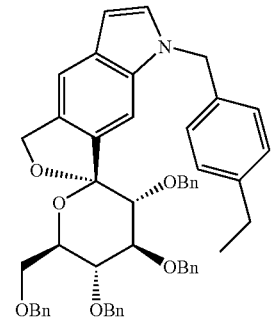

Under a nitrogen stream, to a solution of (3'R,4'S,5'S,6'R,7S)-3',4',5'-tris-benzyloxy-6'-benzyloxymethyl-3',4',5',6'-tetrahydro-spiro[furo[3,4,f]indole-7(1H,5H),2'-[2H]pyran] (47 mg, 0.07 mmol) in N,N-dimethylformamide (0.69 mL) was added sodium hydroxide (50%, 4 mg, 0.08 mmol) under ice cooling, and the resultant mixture was stirred for 0.5 hours at the same temperature. To the mixture was then added 4-ethylbenzyl bromide (17 mg, 0.09 mmol) in N,N-dimethylformamide (0.19 mL), and the solution was stirred for 2 hours at the same temperature. The reaction mixture was purified by silica gel column chromatography (developing solution=ethyl acetate:n-hexane (1:3)), to thereby obtain the titled compound (45 mg, 82%).

$^1$H-NMR (CDCl$_3$) δ: 1.07 (3H, t, J=7.55 Hz), 2.44 (2H, q, J=7.55, 7.69 Hz), 3.67 (1H, dd, J=1.65, 11.25 Hz), 3.79-3.90 (4H, m), 4.09-4.17 (2H, m), 4.30 (1H, d, J=10.70 Hz), 4.42-

4.66 (3H, m), 4.84-4.93 (3H, m), 5.20-5.33 (4H, m), 6.54-6.59 (3H, m), 6.89 (4H, s), 6.97-7.32 (20H, m), 7.49 (1H, s).

11) Synthesis of (3'R,4'S,5'S,6'R,7S)-1-[(4-ethylphenyl)methyl]-6'-hydroxymethyl-3',4',5',6'-tetrahydro-spiro[furo[3,4,f]indole-7(5H),2'-[2H]pyran]-3',4',5' triol

[Formula 42]

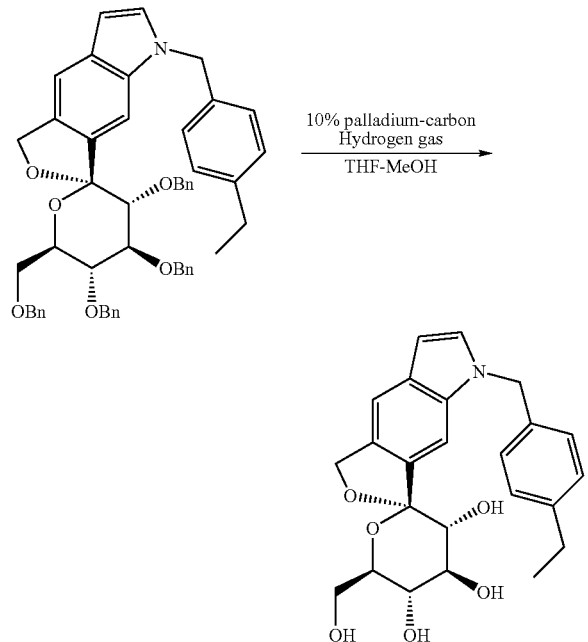

To a solution of (3'R,4'S,5'S,6'R,7S)-3',4',5'-tris-benzyloxy-6'-benzyloxymethyl-1-[(4-ethylphenyl)methyl]-3',4',5',6'-tetrahydro-spiro[furo[3,4,f]indole-7(5H),2'-[2H]pyran] (43 mg, 0.055 mmol) in methanol (1 mL) and THF (1 mL) was added with 10% palladium on carbon (41 mg). The resultant solution was stirred under a hydrogen atmosphere for 1 hour at room temperature, and the catalyst was then filtered off. Solvent was then removed by distillation under reduced pressure, and the resulting residue was purified by silica gel column chromatography (developing solution=dichloromethane:methanol (10:1)), to thereby obtain the titled compound (10 mg, 43%).

$^1$H-NMR (CD$_3$OD) δ: 1.18 (3H, t, J=7.68 Hz), 2.59 (2H, q, J=7.55, 7.68 Hz), 3.44-3.50 (1H, m), 3.62-3.68 (1H, m), 3.74-3.86 (4H, m), 5.13-5.26 (2H, m), 5.35 (2H, s), 6.47-6.48 (1H, m), 7.03-7.12 (4H, m), 7.26 (1H, d, J=3.29 Hz), 7.38 (1H, s), 7.41 (1H, d, J=0.82 Hz).

MS (ESI$^+$): 426 [M+1]$^+$.

HPLC retention time: 11.6 minutes

<HPLC Measurement Conditions>

Column: YMC-Pack ODS-A 6.0×150 mm, 5 μm

Mobile phase: Eluted under gradient from 0.1% TFA/MeCN (5%)+0.1% TFA/H$_2$O (95%) to 0.1% TFA/MeCN (100%) over 20 minutes, and then under the same conditions (0.1% TFA/MeCN (100%)) for 5 minutes.

Flow rate: 1.5 mL/min

Column temperature: Room temperature

Detection conditions: Total plot over all wavelengths from 230 to 400 nm

Example 3

(1S,3'R,4'S,5'S,6'R)-8-[(4-ethylphenyl)methyl]-3,3',4,4',5',6'-hexahydro-6'-hydroxymethyl-spiro[2-oxa-9-thia-fluorene-1,2'-[2H]pyran]-3',4',5'-triol 1) Synthesis of methyl 2-(3-ethoxycarbonyl-2-oxo-propylsulfanyl)-benzoate

[Formula 43]

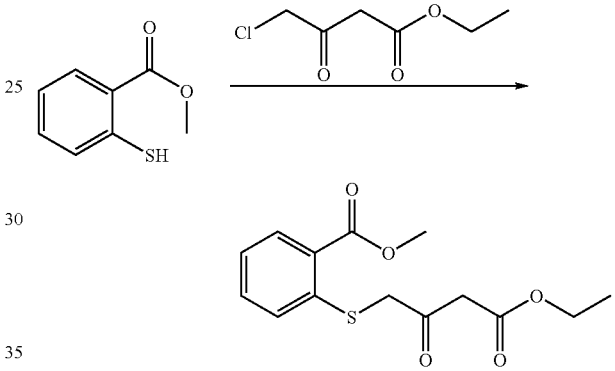

Under a nitrogen stream, trimethylamine (10.0 mL, 72.0 mmol) and ethyl 4-chloro-3-oxo-acetate (4.9 mL, 36.0 mmol) were added dropwise at 0° C. to a solution (100 mL) of methyl 2-mercapto-benzoate (5.0 g, 30.0 mmol) in THF, and the resultant solution was stirred for 10 minutes. After further stirring for 2 hours at room temperature, the reaction solution was filtered through Celite. Solvent was then removed by distillation under reduced pressure, and the resulting residue was purified by silica gel column chromatography (developing solution=ethyl acetate:n-hexane (1:2)), to thereby obtain the titled compound (8.02 g, 90%).

$^1$H-NMR (CDCl$_3$) δ: 1.25 (3H, t, J=7.1 Hz), 3.67 (2H, s), 3.89 (2H, s), 3.93 (3H, s), 4.17 (2H, q, J=7.1 Hz), 7.18-7.31 (2H, m), 7.42-7.49 (1H, m), 7.98-8.01 (1H, m).

2) Synthesis of methyl 3-ethoxycarbonylmethyl-benzo[b]thiophene-7-carboxylate

[Formula 44]

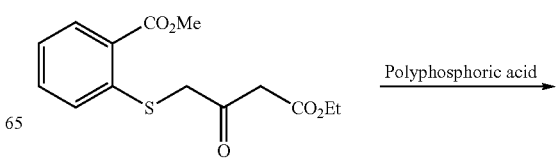

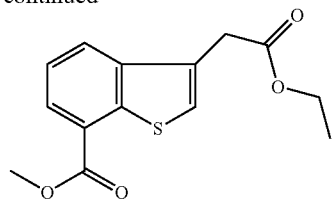

Under a nitrogen stream, to methyl 2-(3-ethoxycarbonyl-2-oxo-propylsulfanyl)-benzoate (8.02 g, 27.1 mmol) was added polyphosphoric acid (25 g) at room temperature, and the resultant solution was stirred for 1 hour at 80° C. Under ice-cooling, to the solution was added water, and the resultant mixture was extracted with ethyl acetate. The organic layer was washed with saturated aqueous sodium bicarbonate and dried over anhydrous magnesium sulfate. Solvent was then removed by distillation under reduced pressure. The resulting residue was purified by silica gel column chromatography (developing solution=ethyl acetate:n-hexane (1:3)), to thereby obtain the titled compound (2.77 g, 37%).

$^1$H-NMR (CDCl$_3$) δ: 1.25 (3H, t, J=7.3 Hz), 3.88 (2H, s), 4.03 (3H, s), 4.17 (2H, q, J=7.3 Hz), 7.49 (1H, s), 7.49 (1H, t, J=8.1 Hz), 7.99 (1H, dd, J=8.1, 1.2 Hz), 8.13 (1H, dd, J=8.1, 1.2 Hz).

3) Synthesis of 2-(7-hydroxymethyl-benzo[b]thiophen-3-yl)-ethanol

[Formula 45]

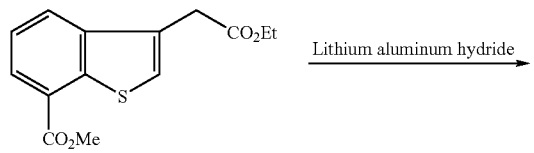

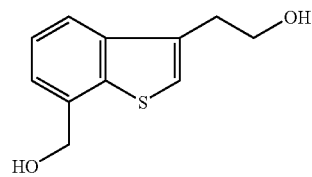

Under a nitrogen stream, to a solution (38 mL) of lithium aluminum hydride (0.74 g, 19.5 mmol) in THF was added a solution (30 mL) of methyl 3-ethoxycarbonylmethyl-benzo[b]thiophene-7-carboxylate (2.7 g, 9.7 mmol) in THF at 0° C., and the resultant solution was stirred for 10 minutes at the same temperature. To the solution was further added lithium aluminum hydride (0.74 g, 19.5 mmol) at 0° C., and the resultant solution was stirred for 10 minutes at the same temperature. Ethyl acetate was added to the solution, and then water (5.2 mL) was added thereto at 0° C. The temperature of the resultant solution was raised to room temperature, and then the solution was stirred for 10 minutes. The reaction mixture was filtered through Celite. Solvent was then removed by distillation under reduced pressure. The resulting residue was treated by addition of ethyl acetate and n-hexane (1:2), to thereby obtain the titled compound (1.97 g, 98%).

$^1$H-NMR (DMSO-d$_6$) δ: 2.97 (2H, t, J=7.0 Hz), 3.71 (2H, q, J=7.0 Hz), 4.71-4.75 (3H, m), 5.44 (1H, t, J=5.9 Hz), 7.35-7.42 (3H, m), 7.71 (1H, d, J=7.3 Hz).

4) Synthesis of 3-[2-(1-methoxy-1-methyl-ethoxy)-ethyl]-7-(1-methoxy-1-methyl-ethoxymethyl)-benzo[b]thiophene

[Formula 46]

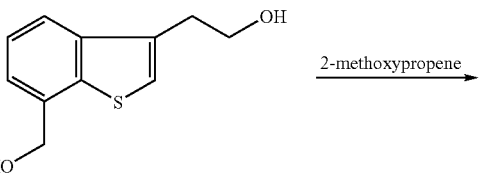

Under a nitrogen stream, to a solution (3 mL) of 2-(7-hydroxymethyl-benzo[b]thiophen-3-yl)-ethanol (78 mg, 0.37 mmol) in THF were added 2-methoxypropene (358 μL, 3.7 mmol) and pyridinium p-toluenesulfonic acid (1 mg, 0.037 mmol) at 0° C. The resultant solution was stirred at the same temperature for 30 minutes, and then saturated aqueous sodium hydrogen carbonate was added thereto. The resultant mixture was extracted with ethyl acetate. The organic layer was washed with saturated brine and then dried over anhydrous magnesium sulfate. Solvent was then removed by distillation under reduced pressure, to thereby obtain a crude product of the titled compound (123 mg, 94%).

$^1$H-NMR (CDCl$_3$) δ: 1.44 (6H, s), 1.48 (6H, s), 3.28 (3H, s), 3.31 (3H, s), 4.74 (2H, s), 4.76 (2H, s), 7.26 (1H, s), 7.38-7.40 (1H, m), 7.73 (1H, t, J=4.5 Hz).

5) Synthesis of (1S,3'R,4'S,5'S,6'R)-3',4',5'-tris-benzyloxy-6'-benzyloxymethyl-3,3',4,4',5',6'-hexahydro-8-hydroxymethyl-spiro[2-oxa-9-thia-fluorene-1,2'-[2H]pyran]

[Formula 47]

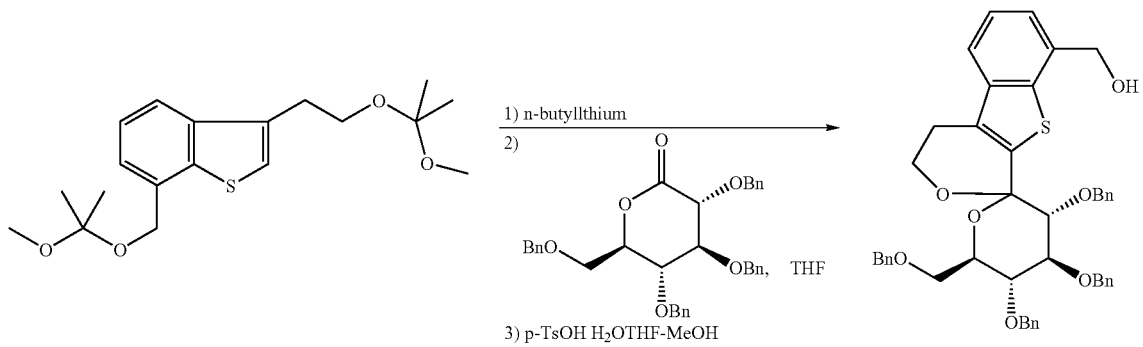

Under a nitrogen stream, a solution of n-butyllithium in n-hexane (1.0 M, 248 µL, 0.25 mmol) was added dropwise at −78° C. to a solution (1 mL) of 3-[2-(1-methoxy-1-methyl-ethoxy)-ethyl]-7-(1-methoxy-1-methyl-ethoxymethyl)-benzo[b]thiophene (73 mg, 0.21 mmol) in THF, and the resultant solution was stirred for 30 minutes. A solution (1 mL) of (3R,4S,5R,6R)-3,4,5-tris-benzyloxy-6-benzyloxymethyl-tetrahydro-pyran-2-one (172 mg, 0.32 mmol) in THF was added dropwise to the solution at the same temperature. The resultant solution was stirred for 30 minutes at room temperature, and then water was added thereto. The resultant mixture was extracted with ethyl acetate. The organic layer was washed with saturated brine and then dried over anhydrous magnesium sulfate. Solvent was then removed by distillation under reduced pressure, to thereby obtain a residue (241 mg).

Then, the obtained residue (241 mg) was dissolved in THF (2 mL) and methanol (2 mL). p-Toluenesulfonic acid (2 mg) was added, and the resultant solution was stirred for 13 hours at room temperature. Solvent was then removed by distillation under reduced pressure, and the resulting residue was purified by silica gel column chromatography (developing solution=ethyl acetate:n-hexane (1:1)), to thereby obtain the titled compound (72 mg, 48%) as a mixture of diastereomers.

$^1$H-NMR (CDCl$_3$) δ: 1.87 (1H, brs), 2.76-2.83 (1H, m), 3.05-3.10 (1H, m), 3.70-3.95 (4H, m), 4.03-4.28 (4H, m), 4.42-4.58 (2H, m), 4.62-4.72 (3H, m), 4.84-4.98 (5H, m), 6.78-6.81 (2H, m), 6.89-7.04 (3H, m), 7.20-7.46 (17H, m), 7.62-7.65 (1H, m).

6) Synthesis of (1S,3'R,4'S,5'S,6'R)-3',4',5'-tris-benzyloxy-6'-benzyloxymethyl-8-chloromethyl-3,3',4,4',5',6'-hexahydro-spiro[2-oxa-9-thia-fluorene-1,2'-[2H]pyran]

[Formula 48]

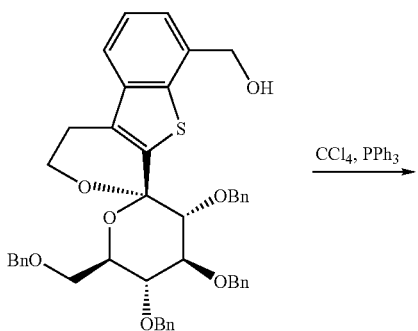

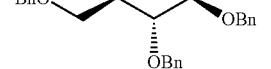

To a solution of (1S,3'R,4'S,5'S,6'R)-3',4',5'-tris-benzyloxy-6'-benzyloxymethyl-3,3',4,4',5',6'-hexahydro-8-hydroxymethyl-spiro[2-oxa-9-thia-fluorene-1,2'-[2H]pyran] (72 mg, 0.10 mmol) in dichloromethane (1 mL) were added carbon tetrachloride (48 µL, 0.5 mmol) and triphenylphosphine (131 mg, 0.5 mmol). The resultant solution was then stirred for 3 hours at room temperature. The reaction solution was concentrated under reduced pressure, and the resulting residue was purified by silica gel column chromatography (developing solution=ethyl acetate:n-hexane (1:2)), to thereby obtain the titled compound (42 mg, 48%).

$^1$H-NMR (CDCl$_3$) δ: 2.78 (1H, dd, J=16.2, 2.4 Hz), 3.03-3.10 (1H, m), 3.71 (1H, dd, J=11.2, 1.8 Hz), 3.81-3.95 (3H, m), 4.03-4.27 (4H, m), 4.42 (1H, d, J=11.0 Hz), 4.52 (1H, d, J=12.2 Hz), 4.63-4.74 (3H, m), 4.79 (2H, s), 4.83-4.99 (3H, m), 6.79-6.82 (2H, m), 6.89-7.04 (3H, m), 7.20-7.41 (17H, m), 7.64-7.70 (1H, m).

7) Synthesis of (1S,3'R,4'S,5'S,6'R)-3',4',5'-tris-benzyloxy-6'-benzyloxymethyl-8-[(4-ethylphenyl)methyl]-3,3',4,4',5',6'-hexahydro-spiro[2-oxa-9-thia-fluorene-1,2'-[2H]pyran]

[Formula 49]

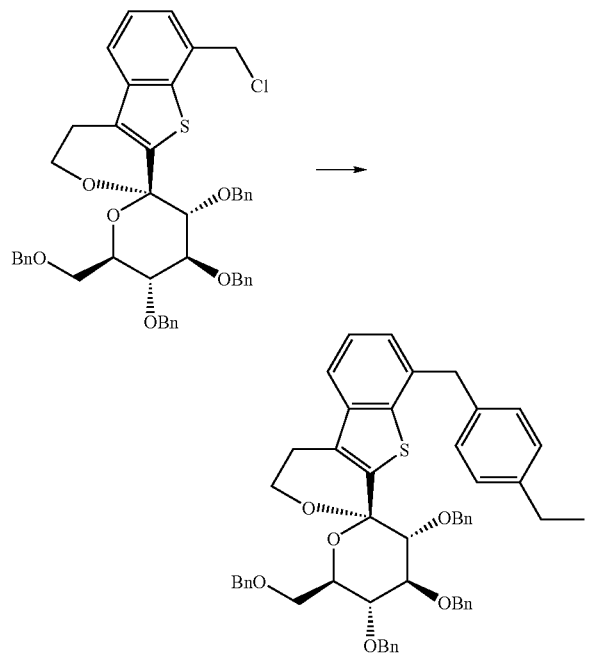

Under a nitrogen stream, to a mixture of (1S,3'R,4'S,5'S,6'R)-3',4',5'-tris-benzyloxy-6'-benzyloxymethyl-8-chloromethyl-3,3',4,4',5',6'-hexahydro-spiro[2-oxa-9-thia-fluorene-1,2'-[2H]pyran] (41 mg, 0.05 mmol), 4-ethylphenylboronic acid (13.0 mg, 0.08 mmol), potassium phosphate (21.0 mg, 1.00 mmol), palladium acetate (1.2 mg, 0.005 mmol) and triphenylphosphine (2.6 mg, 0.01 mmol) was added toluene (2.6 mg, 0.5 mmol), and the resultant solution was stirred for 4 hours at 80° C. Solvent was concentrated under reduced pressure, and the resulting residue was purified by silica gel column chromatography (developing solution=ethyl acetate: n-hexane (1:3)), to thereby obtain the titled compound (23 mg, 56%).

$^1$H-NMR (CDCl$_3$) δ: 1.14 (3H, t, J=7.4 Hz), 2.53 (2H, g, J=7.4 Hz), 2.76 (1H, dd, J=16.2, 2.5 Hz), 3.03-3.09 (1H, m), 3.69-3.74 (1H, m), 3.81-3.92 (3H, m), 4.00-4.26 (6H, m), 4.32 (1H, d, J=11.0 Hz), 4.50 (1H, d, J=11.2 Hz), 4.59-4.67 (3H, m), 4.86-4.96 (3H, m), 6.72 (2H, d, J=7.3 Hz), 6.91-7.40 (25H, m), 7.58 (1H, d, J=7.6 Hz).

8) Synthesis of (1S,3'R,4'S,5'S,6'R)-8-[(4-ethylphenyl)methyl]-3,3',4,4',5',6'-hexahydro-6'-hydroxymethyl-spiro[2-oxa-9-thia-fluorene-1,2'-[2H]pyran]-3',4',5'-triol

[Formula 50]

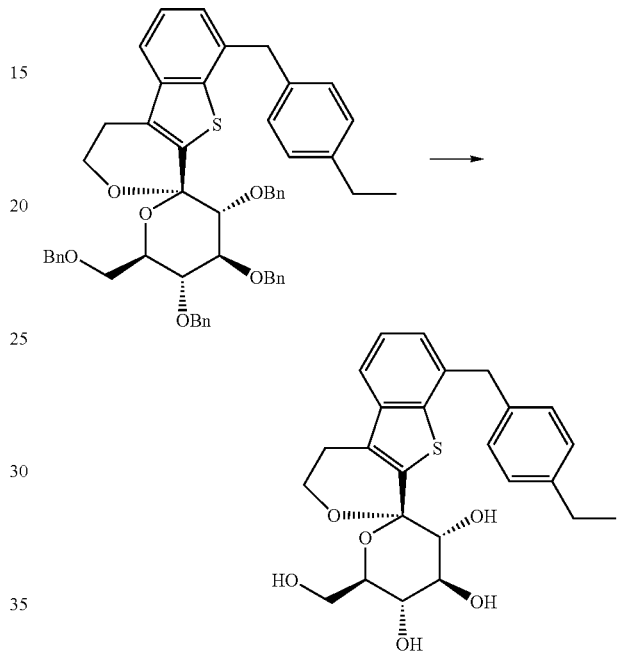

To a solution of (1S,3'R,4'S,5'S,6'R)-3',4',5'-tris-benzyloxy-6'-benzyloxymethyl-8-[(4-ethylphenyl)methyl]-3,3',4,4',5',6'-hexahydro-spiro[2-oxa-9-thia-fluorene-1,2'-[2H]pyran] (23 mg, 0.028 mmol) in methanol (1 mL) and ethyl acetate (1 mL) was added 10% palladium on carbon (10 mg). The resultant mixture was stirred under a hydrogen atmosphere for 1 hour at room temperature, and the catalyst was then filtered off. Solvent was then removed by distillation under reduced pressure, and the resulting residue was purified by silica gel column chromatography (developing solution=dichloromethane:methanol (10:1)), to thereby obtain the titled compound (10.4 mg, 81%).

$^1$H-NMR (CD$_3$OD) δ: 1.19 (3H, t, J=7.6 Hz), 2.58 (2H, q, J=7.6 Hz), 2.76 (1H, dd, J=16.2, 2.0 Hz), 2.96-3.06 (1H, m), 3.37-3.44 (1H, m), 3.63-3.71 (2H, m), 3.74-3.88 (3H, m), 4.15-4.25 (4H, m), 7.07 (2H, d, J=8.2 Hz), 7.13 (2H, d, J=8.2 Hz), 7.18 (1H, d, J=7.3 Hz), 7.35 (1H, dd, J=7.9, 7.3 Hz), 7.58 (1H, d, J=7.9 Hz).

MS (ESI$^+$): 456 [M]$^+$.

HPLC retention time: 19.0 minutes

<HPLC Measurement Conditions>

Column: YMC-Pack ODS-A 6.0×150 mm, 5 μm

Mobile phase: Eluted under gradient from 10 mM AcONH$_4$/MeOH (5%)+10 mM AcONH$_4$/H$_2$O (95%) to 10 mM AcONH$_4$/MeOH (100%) over 20 minutes, and then under the same conditions (10 mM AcONH$_4$/MeOH (100%)) for 5 minutes.

Flow rate: 1.5 mL/min

Column temperature: Room temperature

Detection conditions: Total plot over all wavelengths from 230 to 400 nm

The structural formula of the compounds of the above examples are illustrated in Table 1-1.

TABLE 1-1

| Example 1 | 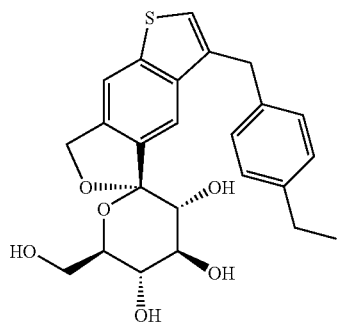 |

TABLE 1-1-continued

| Example 2 | 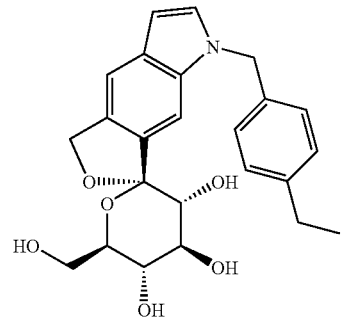 |
| Example 3 | 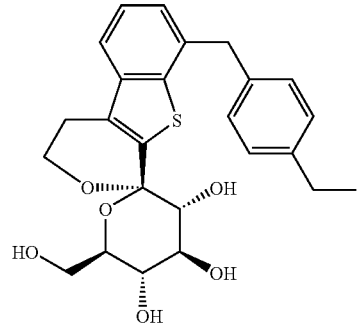 |

The compounds listed in Tables 1-2 and 1-3 can be easily produced in the same manner as described in Example 1 or in the production processes, or by making slight modifications to such methods that would be obvious to a person skilled in the art.

TABLE 1-2

| Example 4 | 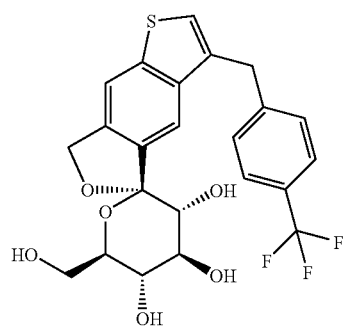 | $^1$H-NMR (CD$_3$OD) δ: 3.49 (1H, t, J = 9.3 Hz), 3.67 (1H, dd, J = 11.9, 5.7 Hz), 3.78-3.84 (4H, m) 4.31 (2H, s), 5.23 (2H, q, J = 12.9 Hz), 7.19 (1H, s), 7.47 (2H, d, J = 8.1 Hz), 7.59 (2H, d, J = 8.4 Hz), 7.78 (2H, d, J = 7.3 Hz)<br>MS (ESI$^+$): 483 [M + 1]$^+$ |
| Example 5 | 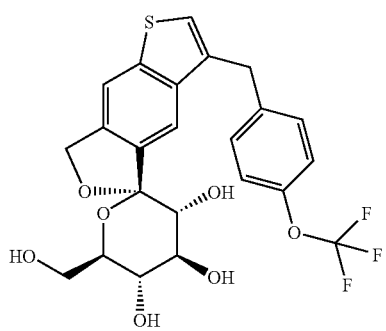 | $^1$H-NMR (CD$_3$OD) δ: 3.49 (1H, t, J = 9.2 Hz), 3.67 (1H, dd, J = 11.7, 5.5 Hz), 3.78-3.85 (4H, m), 4.25 (2H, s), 5.23 (2H, q, J = 13.1 Hz), 7.16 (1H, s), 7.19 (2H, d, J = 8.1 Hz), 7.37 (2H, d, J = 8.4 Hz), 7.78 (2H, d, J = 4.8 Hz)<br>MS (ESI$^+$): 499 [M + 1]$^+$ |

TABLE 1-2-continued
| Example 6 | ![structure] | $^1$H-NMR (CD$_3$OD) δ: 3.46-3.53 (1H, m), 3.64-3.70 (1H, m), 3.76-3.87 (4H, m), 4.20 (2H, s), 5.17-5.29 (2H, m), 6.96-7.05 (2H, m), 7.12 (1H, s), 7.25-7.32 (2H, m), 7.76 (1H, s), 7.77-7.78 (1H, m)<br>MS (ESI$^+$): 433 [M + 1]$^+$ |
|---|---|---|
| Example 7 | ![structure] | $^1$H-NMR (CD$_3$OD) δ: 0.60-0.66 (2H, m), 0.88-0.95 (2H, m), 1.81-1.91 (1H, m), 3.46-3.53 (1H, m), 3.64-3.70 (1H, m), 3.76-3.87 (4H, m), 4.15 (2H, s), 5.17-5.29 (2H, m), 6.97-7.02 (2H, m), 7.07 (1H, s), 7.13-7.16 (2H, m), 7.76-7.77 (2H, m)<br>MS (ESI$^+$): 455 [M + 1]$^+$ |
| Example 8 | ![structure] | $^1$H-NMR (CD$_3$OD) δ: 2.30 (3H, s), 3.45-3.56 (1H, m), 3.62-3.73 (1H, m), 3.75-3.82 (4H, m), 4.16 (2H, s), 5.17-5.32 (2H, m), 7.06-7.20 (5H, m), 7.74-7.80 (2H, m)<br>MS (ESI$^+$): 429 [M + 1]$^+$ |
TABLE 1-3
| Example 9 | 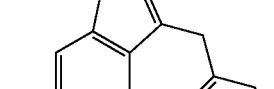 | $^1$H-NMR (CD$_3$OD) δ: 1.23 (6H, d, J = 6.9 Hz), 2.78-2.97 (1H, m), 3.45-3.58 (1H, m), 3.63-3.74 (1H, m), 3.76-3.93 (4H, m), 4.17 (2H, s), 5.17-5.34 (2H, m), 7.06-7.12 (1H, s) 7.13-7.25 (4H, m), 7.77 (2H, m)<br>MS (ESI$^+$): 457 [M + 1]$^+$ |
|---|---|---|

TABLE 1-3-continued

Example 10

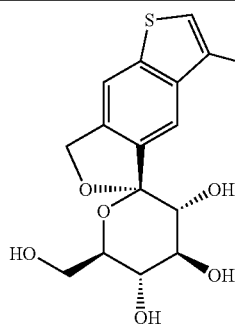

¹H-NMR (CD₃OD) δ: 1.26 (3H, t, J = 7.5 Hz), 2.78 (2H, q, J = 7.4 Hz), 3.51 (1H, t, J = 9.3 Hz), 3.69 (1H, dd, J = 11.7, 5.1 Hz), 3.78-3.89 (4H, m), 4.36 (2H, s), 5.18 (1H, d, J = 12.4 Hz), 5.25 (1H, d, J = 12.1 Hz), 6.63 (1H, d, J = 2.9 Hz), 6.73 (1H, d, J = 2.9 Hz), 7.17 (1H, s), 7.68 (1H, s), 7.70 (1H, s)
MS (ESI⁺): 449 [M + 1]⁺

Example 11

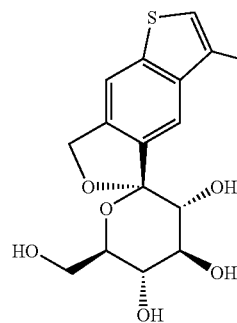

¹H-NMR (CD₃OD) δ: 3.49 (1H, t, J = 9.5 Hz), 3.66 (1H, dd, J = 11.5, 5.7 Hz), 3.76-3.85 (4H, m), 4.52 (2H, s), 5.21 (1H, d, J = 12.8 Hz), 5.28 (1H, d, J = 12.4 Hz), 7.14 (1H, s), 7.23-7.28 (2H, m), 7.41 (1H, s), 7.67 (1H, d, J = 7.3 Hz), 7.74 (1H, d, J = 7.7 Hz), 7.82 (1H, s), 7.85 (1H, s)
MS (ESI⁺): 471 [M + 1]⁺

Example 12

(3'R,4'S,5S,5'S,6'R)-3-[(4-ethylphenyl)methyl]-6'-hydroxymethyl-2-methyl-3',4',5',6'-tetrahydro-spiro[thieno[2,3,f]isobenzofuran-5(7H),2'-[2H]pyran]-3',4',5'-triol 1) Synthesis of (1S,3'R,4'S,5'S,6'R)-3',4',5'-tris-benzyloxy-6'-benzyloxymethyl-5-methylthio-6-(1-propynyl)-3',4',5',6'-tetrahydro-spiro[isobenzofuro-1(3H),2'-[2H]pyran]

[Formula 51]

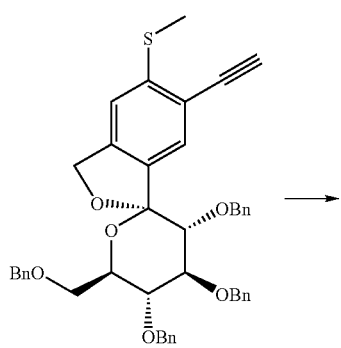

→

-continued

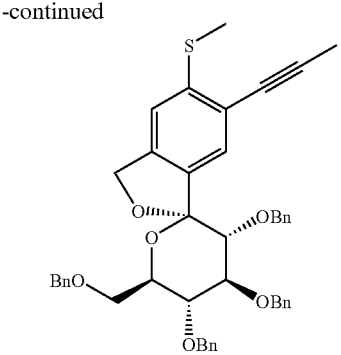

(1S,3'R,4'S,5'S,6'R)-3',4',5'-tris-benzyloxy-6'-benzyloxymethyl-6-ethynyl-5-methylthio-3',4',5',6'-tetrahydro-spiro[isobenzofuro-1(3H), 2'-[2H]pyran] (the compound described in Example 1, step 7) (0.124 g, 0.177 mmol) was dissolved in tetrahydrofuran (1.8 mL), and the resultant solution was cooled to −78° C. A solution of n-butyllithium in n-hexane (1.0 M, 0.195 mmol) was added dropwise thereto. The temperature of the solution was raised over 2 hours to −60° C. Methyl iodide (0.126 g, 0.889 mmol) was added dropwise to the solution. The temperature of the solution was then raised over 1.5 hours to room temperature. Water was added, and the resultant mixture was extracted with diethyl ether. The organic layer was concentrated under reduced pressure, and the resulting residue was purified by silica gel flash column chromatography (developing solution=ethyl acetate: n-hexane (1:4)), to thereby obtain the titled compound (96.0 mg, 75%).
¹H-NMR (CDCl₃) δ: 2.15 (3H, s), 2.49 (3H, s), 3.64 (1H, d, J=9.5 Hz), 3.78-3.83 (3H, m), 4.04-4.06 (1H, m), 4.12 (1H, t, J=9.3 Hz), 4.19 (1H, d, J=11.0 Hz), 4.46, 1H, d, J=12.1 Hz), 4.57-4.63 (3H, m), 4.88-4.93 (3H, m), 5.15 (2H, s), 6.84 (2H, d, J=6.2 Hz), 6.99 (1H, s), 7.12-7.32 (28H, m).
MS (ESI⁺): 713 [M+1]⁺.

2) Synthesis of (3'R,4'S,5S,5'S,6'R)-3',4',5'-tris-benzyloxy-6'-benzyloxymethyl-3-iodo-2-methyl-3',4',5',6'-tetrahydro-spiro[thieno[2,3,f]isobenzofuran-5(7H),2'-[2H]pyran]

[Formula 52]

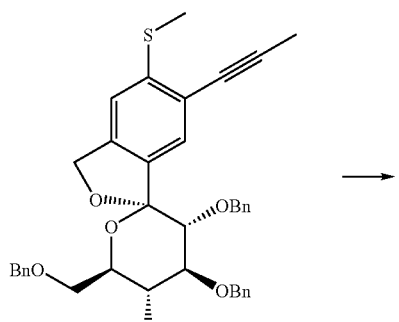

↓

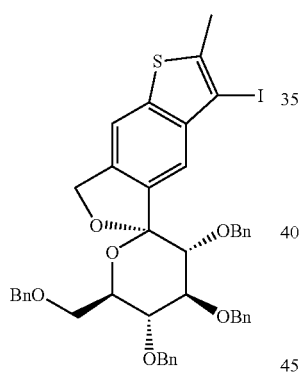

(1S,3'R,4'S,5'S,6'R)-3',4',5'-tris-benzyloxy-6'-benzyloxymethyl-5-methylthio-6-(1-propynyl)-3',4',5',6'-tetrahydro-spiro[isobenzofuro-1(3H),2'-[2H]pyran] (0.119 g, 0.167 mmol) was dissolved in dichloromethane (2.0 mL). To the resultant solution was added a solution of iodine (84.9 mg, 0.334 mmol) in dichloromethane (1.6 mL), and then the solution was stirred for 15 minutes at room temperature. Saturated aqueous sodium thiosulfate was added. The resultant mixture was extracted with diethyl ether. The organic layer was concentrated under reduced pressure, to thereby obtain the titled compound (0.139 g, 100%).

$^{1}$H-NMR (CDCl$_3$) δ: 2.60 (3H, s), 3.67 (1H, d, J=11.0 Hz), 3.83 (1H, dd, J=11.0, 3.7 Hz), 3.91 (1H, t, J=9.7 Hz), 4.02 (1H, d, J=9.5 Hz), 4.13-4.18 (3H, m), 4.51-4.63 (4H, m), 4.89-4.98 (3H, m), 5.30 (2H, s), 6.70 (2H, d, J=7.0 Hz), 6.97-7.02 (3H, m), 7.24-7.30 (15H, m), 7.51 (1H, s), 7.55 (1H, s).

MS (ESI$^+$): 825 [M+1]$^+$.

3) Synthesis of (3'R,4'S,5S,5'S,6'R)-3',4',5'-tris-benzyloxy-6'-benzyloxymethyl-3-[(4-ethylphenyl)methyl]-2-methyl-3',4',5',6'-tetrahydro-spiro[thieno[2,3,f]isobenzofuran-5(7H),2'-[2H]pyran]

[Formula 53]

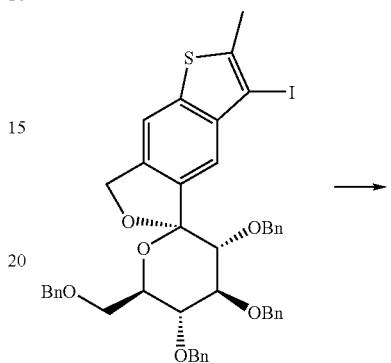

↓

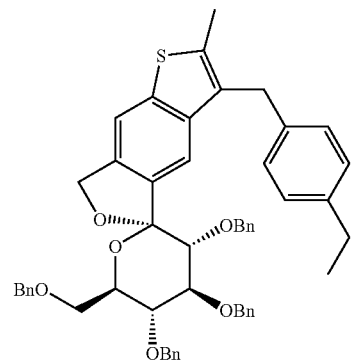

The titled compound (0.106 g, 77%) was obtained in the same manner as that in step 9 of Example 1 using (3'R,4'S,5S,5'S,6'R)-3',4',5'-tris-benzyloxy-6'-benzyloxymethyl-3-iodo-2-methyl-3',4',5',6'-tetrahydro-spiro[thieno[2,3,f]isobenzofuran-5(7H),2'-[2H]pyran] (0.139 g).

$^{1}$H-NMR (CDCl$_3$) δ: 1.04 (3H, t, J=7.5 Hz), 2.38 (2H, q, J=7.5 Hz), 2.53 (3H, s), 3.65-3.69 (3H, m), 3.80-3.85 (2H, m), 4.05-4.17 (4H, m), 4.27 (1H, d, J=11.0 Hz), 4.43 (1H, d, J=12.4 Hz), 4.55-4.67 (2H, m), 4.86-4.91 (3H, m), 5.19-5.30 (2H, m), 6.54 (2H, d, J=7.3 Hz), 6.83 (2H, d, J=7.7 Hz), 6.97-7.04 (5H, m), 7.18-7.33 (15H, m), 7.45 (1H, s), 7.63 (1H, s).

MS (ESI$^+$): 817 [M+1]$^+$.

4) Synthesis of (3'R,4'S,5S,5'S,6'R)-3-[(4-ethylphenyl)methyl]-6'-hydroxymethyl-2-methyl-3',4',5',6'-tetrahydro-spiro[thieno[2,3,f]isobenzofuran-5(7H), 2'-[2H]pyran]-3',4',5'-triol

[Formula 54]

The titled compound (26.6 mg, 37%) was obtained in the same manner as that in step 10 of Example 1 using (3'R,4'S, 5S,5'S,6'R)-3',4',5'-tris-benzyloxy-6'-benzyloxymethyl-3-[(4-ethylphenyl)methyl]-2-methyl-3',4',5',6'-tetrahydro-spiro[thieno[2,3,f]isobenzofuran-5(7H),2'-[2H]pyran] (0.126 g).

$^1$H-NMR (CD$_3$OD) δ: 1.18 (3H, t, J=7.5 Hz), 2.49 (3H, s), 2.57 (2H, q, J=7.7 Hz), 3.45-3.49 (1H, m), 3.66 (1H, dd, J=12.3, 5.7 Hz), 3.76-3.85 (4H, m), 4.17 (2H, s), 5.18 (1H, d, J=12.1 Hz), 5.24 (1H, d, J=12.8 Hz), 7.06 (4H, s), 7.60 (1H, s), 7.68 (1H, s).

MS (ESI$^+$): 457 [M+1]$^+$.

Example 13

(3'R,4'S,5S,5'S,6'R)-2-chloro-3-[(4-ethylphenyl)methyl]-6'-hydroxymethyl-3',4',5',6'-tetrahydro-spiro[thieno[2,3,f]isobenzofuran-5(7H),2'-[2H]pyran]-3',4',5'-triol 1) Synthesis of (1S,3'R,4'S,5'S,6'R)-3',4',5'-tris-benzyloxy-6'-benzyloxymethyl-5-methylthio-3',4',5',6'-tetrahydro-6-(2-trimethylsilylethynyl)-spiro[isobenzofuro-1(3H), 2'-[2H]pyran]

[Formula 55]

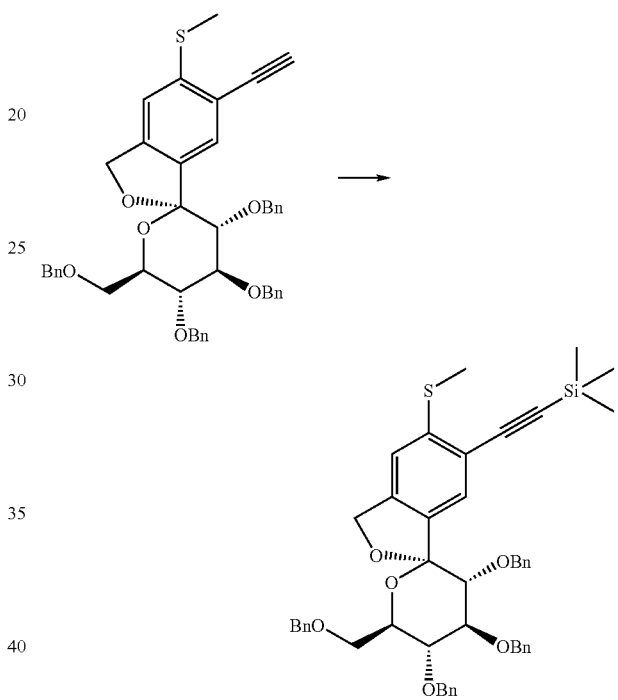

(1S,3'R,4'S,5'S,6'R)-3',4',5'-tris-benzyloxy-6'-benzyloxymethyl-6-ethynyl-5-methylthio-3',4',5',6'-tetrahydro-spiro[isobenzofuro-1(3H), 2'-[2H]pyran] (0.50 g, 0.715 mmol) was dissolved in tetrahydrofuran (2.3 mL), and the resultant solution was cooled to −78° C. A solution of n-butyllithium in n-hexane (1.6 M, 0.491 mmol) was then added dropwise thereto. The resultant mixture was stirred for 1.5 hours, and then trimethylsilyl chloride (0.310 g, 2.861 mmol) was added thereto. The temperature of the solution was raised over 1.5 hours to room temperature. Saturated aqueous sodium hydrogen carbonate was added thereto, and the resultant mixture was extracted with ethyl acetate. The organic layer was concentrated under reduced pressure, and the resulting residue was purified by silica gel flash column chromatography (developing solution=ethyl acetate:n-hexane (1:5)), to thereby obtain the titled compound (267.3 mg, 48%).

$^1$H-NMR (CDCl$_3$) δ: 0.30 (9H, s), 2.50 (3H, s), 3.62 (1H, d, J=9.5 Hz), 3.75-3.84 (3H, m), 4.04 (1H, d, J=7.7 Hz), 4.11 (1H, t, J=9.2 Hz), 4.22 (1H, d, J=11.0 Hz), 4.46 (1H, d, J=12.4 Hz), 4.57-4.62 (3H, m), 4.88-4.93 (3H, m), 5.16 (2H, s), 6.84 (2H, d, J=7.0 Hz), 7.00 (1H, s), 7.14-7.19 (6H, m), 7.25-7.33 (13H, m)

MS (ESI$^+$): 771 [M+1]$^+$..

2) Synthesis of (3'R,4'S,5S,5'S,6'R)-3',4',5'-tris-benzyloxy-6'-benzyloxymethyl-3-iodo-3',4',5',6'-tetrahydro-2-trimethylsilyl-spiro[thieno[2,3,f]isobenzofuran-5(7H),2'-[2H]pyran]

[Formula 56]

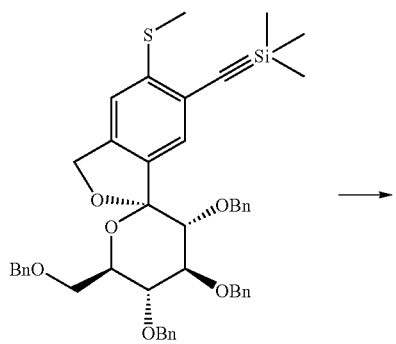

3) Synthesis of (3'R,4'S,5S,5'S,6'R)-3',4',5'-tris-benzyloxy-6'-benzyloxymethyl-3-[(4-ethylphenyl)methyl]-3',4',5',6'-tetrahydro-2-trimethylsilyl-spiro[thieno[2,3,f]isobenzofuran-5(7H),2'-[2H]pyran]

[Formula 57]

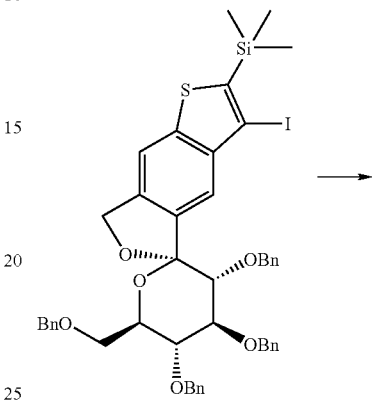

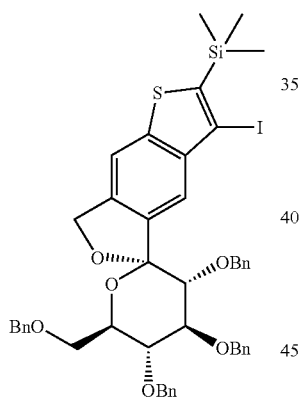

(1S,3'S,4'S,5'S,6'R)-3',4',5'-tris-benzyloxy-6'-benzyloxymethyl-5-methylthio-3',4',5',6'-tetrahydro-6-(2-trimethylsilylethynyl)-spiro[isobenzofuro-1(3H), 2'-[2H]pyran] (0.26 g, 0.337 mmol) was dissolved in dichloromethane (4.0 mL). To the resultant solution was added a solution of iodine (171.1 mg, 0.674 mmol) in dichloromethane (2.7 mL), and then the solution was stirred for 15 minutes at room temperature. Saturated aqueous sodium thiosulfate was added thereto, and the resultant mixture was extracted with diethyl ether. The organic layer was concentrated under reduced pressure, to thereby obtain the titled compound (0.293 g, 98%).

$^1$H-NMR (CDCl$_3$) δ: 0.52 (9H, s), 3.66 (1H, d, J=9.5 Hz), 3.83 (1H, dd, J=11.4, 4.0 Hz), 3.91 (1H, t, J=9.5 Hz), 4.03 (1H, d, J=9.2 Hz), 4.10-4.19 (3H, m), 4.47 (1H, d, J=12.1 Hz), 4.58-4.65 (3H, m), 4.89-4.98 (3H, m), 5.31 (2H, s), 6.69 (2H, d, J=6.2 Hz), 6.92-6.96 (3H, m), 7.21-7.36 (15H, m), 7.59 (1H, s), 7.65 (1H, s).

MS (ESI$^+$): 771 [M+1]$^+$.

The titled compound (0.114 g, 68%) was obtained in the same manner as that in step 9 of Example 1 using (3'R,4'S,5S,5'S,6'R)-3',4',5'-tris-benzyloxy-6'-benzyloxymethyl-3-iodo-3',4',5',6'-tetrahydro-2-trimethylsilyl-spiro[thieno[2,3,f]isobenzofuran-5(7H),2'-[2H]pyran] (0.18 g).

$^1$H-NMR (CDCl$_3$) δ: 0.38 (9H, s), 1.00 (3H, t, J=7.7 Hz), 2.33 (2H, dq, J=15.3, 3.6 Hz), 3.50 (1H, d, J=10.3 Hz), 3.62-3.84 (3H, m), 4.09-4.13 (4H, m), 4.29 (2H, s), 4.42 (1H, d, J=12.1 Hz), 4.55-4.62 (2H, m), 4.81-4.93 (3H, m), 5.20 (1H, d, J=12.8 Hz), 5.27 (2H, d, J=13.5 Hz), 6.50 (2H, d, J=7.0 Hz), 6.78 (2H, d, J=8.1 Hz), 6.89 (2H, d, J=8.1 Hz), 7.02-7.07 (4H, m), 7.21-7.30 (15H, m), 7.44 (1H, s), 7.72 (1H, s).

MS (ESI$^+$): 897 [M+23]$^+$.

4) Synthesis of (3'R,4'S,5S,5'S,6'R)-3',4',5'-tris-benzyloxy-6'-benzyloxymethyl-2-chloro-3-[(4-ethylphenyl)methyl]-3',4',5',6'-tetrahydro-spiro[thieno[2,3,f]isobenzofuran-5(7H),2'-[2H]pyran]

[Formula 58]

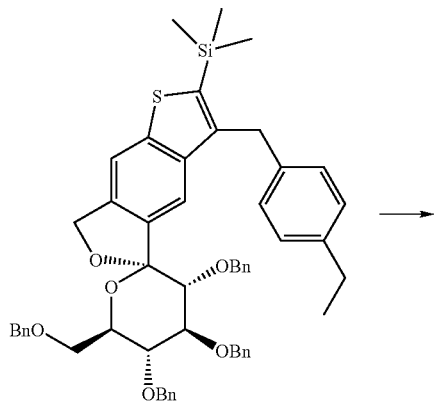

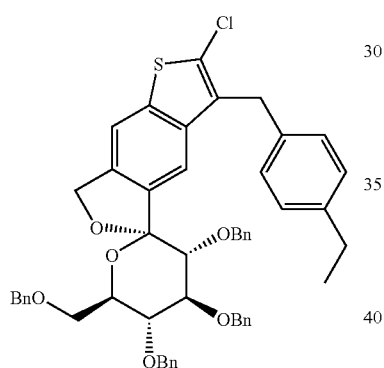

(3'R,4'S,5S,5'S,6'R)-3',4',5'-tris-benzyloxy-6'-benzyloxymethyl-3-[(4-ethylphenyl)methyl]-3',4',5',6'-tetrahydro-2-trimethylsilyl-spiro[thieno[2,3,f]isobenzofuran-5(7H),2'-[2H]pyran] (0.122 g, 0.139 mmol) was dissolved in acetonitrile (0.93 mL). Sulfuryl chloride (20.6 mg, 0.153 mmol) was added to the resultant solution, and then the solution was stirred for 3.5 hours at room temperature. Saturated aqueous sodium hydrogen carbonate was added thereto, and the resultant mixture was extracted with ethyl acetate. The organic layer was concentrated under reduced pressure, and the resulting residue was purified by silica gel flash column chromatography (developing solution=ethyl acetate:n-hexane (1:11.5)), to thereby obtain the titled compound (50.2 mg, 43%).

$^1$H-NMR (CDCl$_3$) δ: 1.04 (3H, t, J=7.7 Hz), 2.39 (2H, q, J=7.6 Hz), 3.66 (1H, dd, J=11.0, 1.8 Hz), 3.71 (1H, d, J=10.6 Hz), 3.81-3.91 (3H, m), 4.08-4.16 (3H, m), 4.26 (1H, d, J=15.7 Hz), 4.34 (1H, d, J=11.0 Hz), 4.45 (1H, d, J=12.1 Hz), 4.58 (1H, d, J=12.1 Hz), 4.65 (1H, d, J=10.6 Hz), 4.87-4.96 (3H, m), 5.21 (1H, d, J=12.8 Hz), 5.27 (1H, d, J=13.2 Hz), 6.54 (2H, d, J=7.0 Hz), 6.87 (2H, d, J=8.1 Hz), 6.99-7.10 (6H, m), 7.21-7.32 (14H, m), 7.48 (1H, s), 7.59 (1H, s).

MS (ESI$^+$): 859 [M+23]$^+$.

5) Synthesis of (3'R,4'S,5S,5',6'R)-2-chloro-3-[(4-ethylphenyl)methyl]-6'-hydroxymethyl-3',4',5',6'-tetrahydro-spiro[thieno[2,3,f]isobenzofuran-5(7H),2'-[2H]pyran]-3',4',5'-triol

[Formula 59]

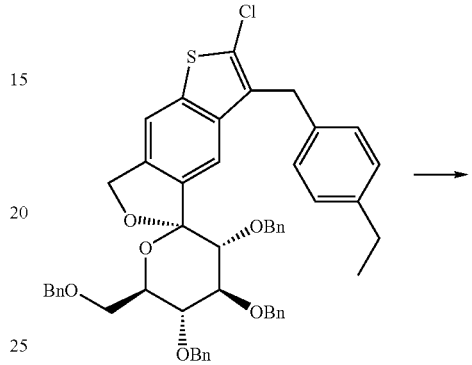

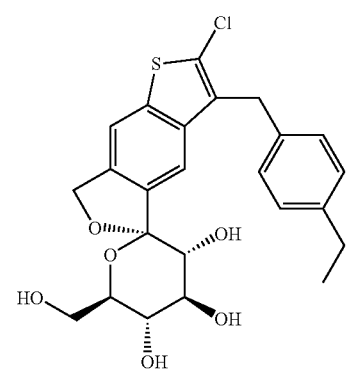

The titled compound (12.8 mg, 44%) was obtained in the same manner as that in step 10 of Example 1 using (3'R,4'S,5S,5'S,6'R)-3',4',5'-tris-benzyloxy-6'-benzyloxymethyl-2-chloro-3-[(4-ethylphenyl)methyl]-3',4',5',6'-tetrahydro-spiro[thieno[2,3,f]isobenzofuran-5(7H),2'-[2H]pyran] (0.051 g).

$^1$H-NMR (CD$_3$OD) δ: 1.18 (3H, t, J=7.7 Hz), 2.58 (2H, q, J=7.7 Hz), 3.48 (1H, dt, J=12.0, 4.2 Hz), 3.66 (1H, dd, J=11.9, 5.7 Hz), 3.78-3.83 (4H, m), 4.22 (2H, s), 5.18 (1H, d, J=12.8 Hz), 5.24 (1H, d, J=13.2 Hz), 7.08 (2H, d, J=8.1 Hz), 7.14 (2H, d, J=7.7 Hz), 7.68 (1H, s), 7.72 (1H, s).

MS (ESI$^+$): 477 [M+1]$^+$.

Example 14

(3'R,4'S,5S,5'S,6'R)-3-(4-ethylphenyl)-6'-hydroxymethyl-3',4',5',6'-tetrahydro-spiro[thieno[2,3,f]isobenzofuran-5(7H),2'-[2H]pyran]-3',4',5'-triol 1) Synthesis of (3'R,4'S,5S,5'S,6'R)-3',4',5'-tris-benzyloxy-6'-benzyloxymethyl-3-(4-ethylphenyl)-3',4',5',6'-tetrahydro-2-trimethylsilyl-spiro[thieno[2,3,f]isobenzofuran-5(7H),2'-[2H]pyran]

[Formula 60]

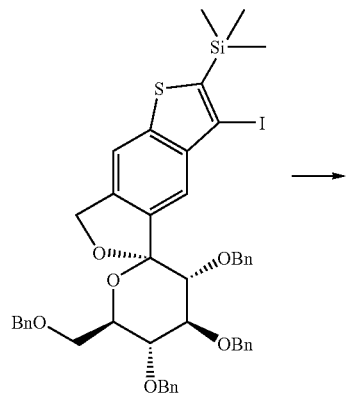

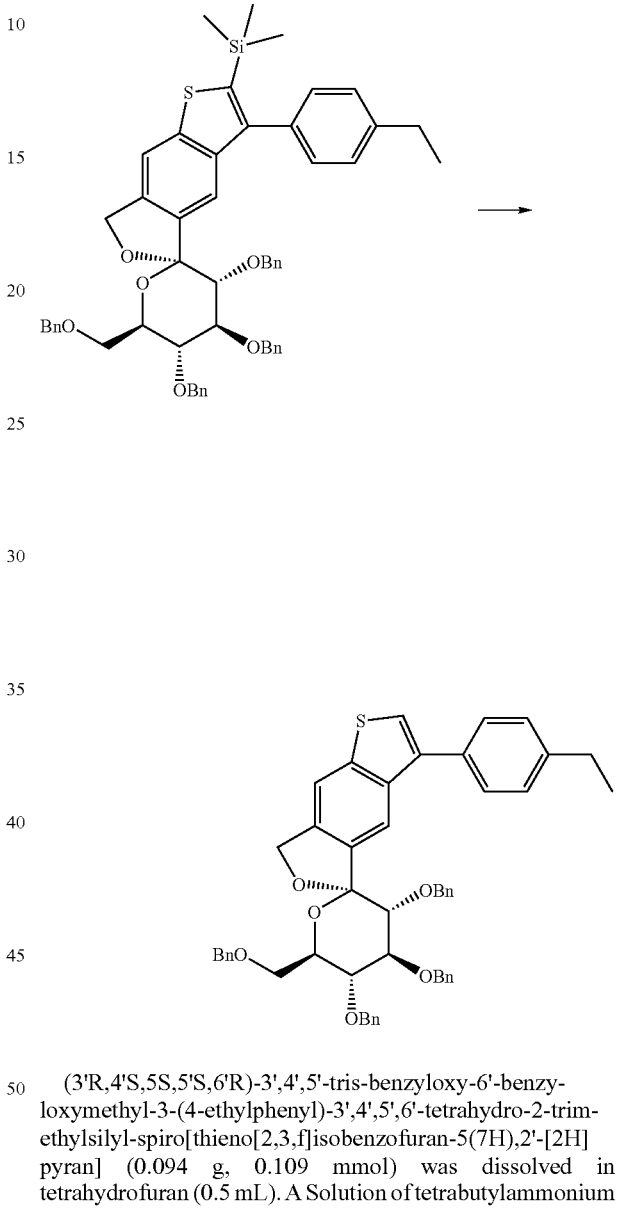

The titled compound (94.4 mg, 80%) was obtained in the same manner as that in step 9 of Example 1 using (3'R,4'S,5S,5'S,6'R)-3',4',5'-tris-benzyloxy-6'-benzyloxymethyl-3-iodo-3',4',5',6'-tetrahydro-2-trimethylsilyl-spiro[thieno[2,3,f]isobenzofuran-5(7H),2'-[2H]pyran] (0.12 g).

$^1$H-NMR (CDCl$_3$) δ: 1.34 (3H, t, J=7.7 Hz), 2.76 (2H, q, J=7.6 Hz), 3.62 (1H, dd, J=11.0, 1.5 Hz), 3.77-3.79 (2H, m), 3.88 (1H, d, J=9.5 Hz), 4.05-4.15 (3H, m), 4.42-4.46 (2H, m), 4.54 (1H, d, J=12.4 Hz), 4.60 (1H, d, J=11.0 Hz), 4.82-4.92 (3H, m), 5.31 (2H, s), 6.71 (2H, d J=7.0 Hz), 6.99-7.09 (3H, m), 7.18-7.28 (19H, m), 7.41 (1H, s), 7.75 (1H, s).

MS (ESI$^+$): 861 [M+1]$^+$.

2) Synthesis of (3'R,4'S,5S,5'S,6'R)-3',4',5'-tris-benzyloxy-6'-benzyloxymethyl-3-(4-ethylphenyl)-3',4',5',6'-tetrahydro-spiro[thieno[2,3,f]isobenzofuran-5(7H),2'-[2H]pyran]

[Formula 61]

(3'R,4'S,5S,5'S,6'R)-3',4',5'-tris-benzyloxy-6'-benzyloxymethyl-3-(4-ethylphenyl)-3',4',5',6'-tetrahydro-2-trimethylsilyl-spiro[thieno[2,3,f]isobenzofuran-5(7H),2'-[2H]pyran] (0.094 g, 0.109 mmol) was dissolved in tetrahydrofuran (0.5 mL). A Solution of tetrabutylammonium fluoride/tetrahydrofuran (1.0 M, 0.43 mL) was added thereto, and then the mixture was stirred for 1.5 hours at room temperature. Saturated aqueous ammonium chloride was added thereto, and the resultant mixture was extracted with diethyl ether. The organic layer was concentrated under reduced pressure, to thereby obtain the titled compound (84.5 mg, 98%).

$^1$H-NMR (CDCl$_3$) δ: 1.33 (3H, t, J=7.7 Hz), 2.74 (2H, q, J=7.4 Hz), 3.65 (2H, d, J=9.9 Hz), 3.81-3.86 (2H, m), 3.96 (1H, d, J=9.5 Hz), 4.10-4.18 (2H, m), 4.44 (1H, d, J=12.1 Hz), 4.55-4.62 (3H, m), 4.87-4.92 (3H, m), 5.33 (2H, s), 6.70 (2H, d, J=7.3 Hz), 6.92-7.01 (3H, m), 7.19-7.41 (20H, m), 7.76 (2H, s).

MS (ESI$^+$): 789 [M+1]$^+$.

3) Synthesis of (3'R,4'S,5S,5'S,6'R)-3-(4-ethylphenyl)-6'-hydroxymethyl-3',4',5',6'-tetrahydro-spiro[thieno[2,3,f]isobenzofuran-5(7H),2'-[2H]pyran]-3',4',5,-triol

[Formula 62]

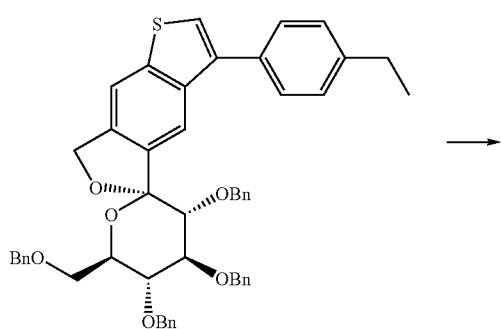

→

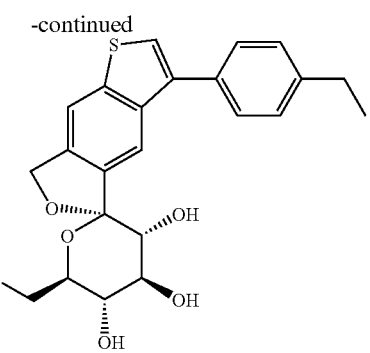

The titled compound (19.6 mg, 42%) was obtained in the same manner as that in step 10 of Example 1 using (3'R,4'S,5S,5'S,6'R)-3',4',5'-tris-benzyloxy-6'-benzyloxymethyl-3-(4-ethylphenyl)-3',4',5',6'-tetrahydro-spiro[thieno[2,3,f]isobenzofuran-5(7H),2'-[2H]pyran] (0.084 g).
$^1$H-NMR (CD$_3$OD) δ: 1.30 (3H, t, J=7.5 Hz), 2.73 (2H, q, J=7.6 Hz), 3.51 (1H, t, J=9.3 Hz), 3.70 (1H, dd, J=11.9, 5.3 Hz), 3.78-3.85 (4H, m), 5.24 (1H, d, J=12.4 Hz), 5.30 (1H, d, J=12.4 Hz), 7.35 (2H, d, J=7.7 Hz), 7.52-7.53 (3H, m), 7.85 (2H, d, J=3.7 Hz).
MS (ESI$^+$): 429 [M+1]$^+$.

The compounds listed in Tables 2-1 to 2-3 can be easily produced in the same manner as described in Example 2 or in the production processes, or by making slight modifications to such methods that would be obvious to a person skilled in the art.

TABLE 2-1

| Example 15 | 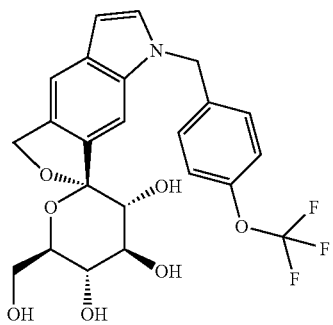 | $^1$H-NMR (CD$_3$OD) δ: 3.42-3.52 (1H, m), 3.62-3.72 (1H, m), 3.72-3.88 (4H, m) 5.14-5.30 (2H, m), 5.45 (2H, s), 6.53 (1H, dd, J = 0.9, 3.3 Hz), 7.15-7.27 (4H, m), 7.32 (1H, d, J = 3.0 Hz), 7.40 (3H, s), 7.44 (1H, d, J = 0.9 Hz)<br>MS (ESI$^+$): 482 [M + 1]$^+$ |
|---|---|---|
| Example 16 | 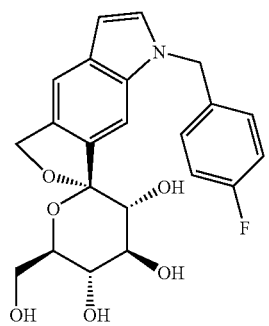 | $^1$H-NMR (CD$_3$OD) δ: 3.44-3.53 (1H, m), 3.62-3.72 (1H, m), 3.73-3.90 (4H, m) 5.12-5.30 (2H, m), 5.39 (2H, s), 6.50 (1H, dd, J = 0.8, 3.2 Hz), 6.95-7.06 (2H, m), 7.13-7.22 (2H, m), 7.30 (1H, d, J = 3.3 Hz), 7.39 (1H, s), 7.43 (1H, d, J = 0.9 Hz)<br>MS (ESI$^+$): 416 [M + 1]$^+$ |

TABLE 2-1-continued

| Example 17 | 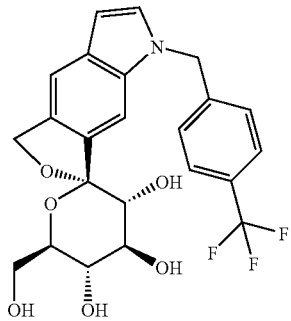 | $^1$H-NMR (CD$_3$OD) δ: 3.42-3.52 (1H, m), 3.60-3.72 (1H, m), 3.72-3.90 (4H, m) 5.15-5.32 (2H, m), 5.52 (2H, s), 6.55 (1H, dd, J = 0.8, 3.2 Hz) 7.28 (2H, d, J = 8.1 Hz), 7.34 (1H, d, J = 3.0 Hz), 7.38 (1H, s), 7.45 (1H, d, J = 0.9 Hz), 7.58 (2H, d, J = 8.4 Hz) MS (ESI$^+$): 466 [M + 1]$^+$ |
|---|---|---|
| Example 18 | 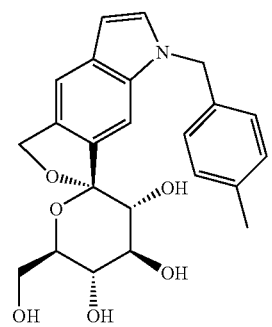 | $^1$H-NMR (CD$_3$OD) δ: 2.28 (3H, s), 3.44-3.57 (1H, m), 3.58-3.72 (1H, m), 3.72-3.93 (4H, m) 5.12-5.32 (2H, m), 5.35 (2H, s), 6.48 (1H, d, J = 3.3 Hz) 7.00-7.14 (4H, m), 7.27 (1H, d, J = 3.3 Hz), 7.38 (1H, s), 7.42 (1H, s) MS (ESI$^+$): 412 [M + 1]$^+$ |

TABLE 2-2

| Example 19 | 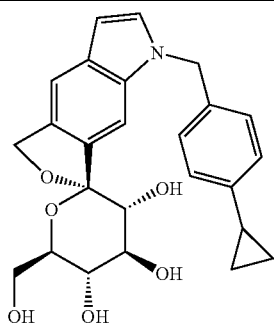 | $^1$H-NMR (CD$_3$OD) δ: 0.59-0.64 (2H, m), 0.88-0.94 (2H, m), 1.80-1.89 (1H, m), 3.43-3.50 (1H, m), 3.62-3.68 (1H, m), 3.74-3.86 (4H, m), 5.13-5.25 (2H, m), 5.33 (2H, s), 6.47-6.48 (1H, m), 6.96-7.04 (4H, m), 7.26 (1H, d, J = 3.29 Hz), 7.37 (1H, s), 7.41 (1H, d, J = 0.82 Hz) MS (ESI$^+$): 438 [M + 1]$^+$ |
|---|---|---|
| Example 20 | 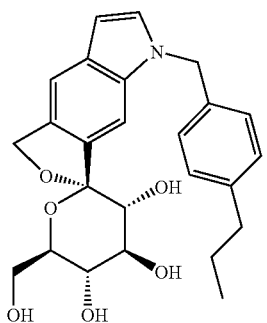 | $^1$H-NMR (CD$_3$OD) δ: 0.88-0.93 (3H, m), 1.56-1.63 (2H, m), 2.51-2.56 (2H, m), 3.46-3.50 (1H, m), 3.64-3.68 (1H, m), 3.74-3.86 (4H, m), 5.14-5.26 (2H, m), 5.35 (2H, s), 6.47-6.48 (1H, d, J = 2.47 Hz), 7.03-7.10 (4H, m), 7.26 (1H, d, J = 3.29 Hz), 7.38 (1H, s), 7.41 (1H, d, J = 0.82 Hz) MS (ESI$^+$): 440 [M + 1]$^+$ |

TABLE 2-2-continued

| Example 21 | 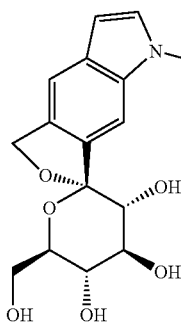 | ¹H-NMR (CD₃OD) δ: 1.22 (3H, t, J = 7.69 Hz), 2.74 (2H, q, J = 7.41, 7.69 Hz), 3.50 (1H, dd, J = 8.51, 9.88 Hz), 3.65-3.90 (5H, m), 5.14-5.26 (2H, m), 5.46 (2H, s), 6.45-6.46 (1H, m), 6.59-6.61 (1H, m), 6.79 (1H, d, J = 3.29 Hz), 7.27 (1H, d, J = 3.29 Hz), 7.40 (1H, d, J = 0.82 Hz), 7.46 (1H, s)<br>MS (ESI⁺): 432 [M + 1]⁺ |
|---|---|---|
| Example 22 | 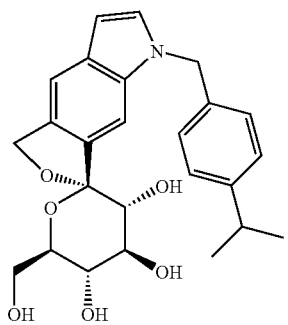 | ¹H-NMR (CD₃OD) δ: 1.21 (6H, d, J = 6.93 Hz), 2.85 (1H, quin, J = 6.77 Hz), 3.44-3.50 (1H, m), 3.62-3.69 (1H, m), 3.75-3.87 (4H, m), 5.15-5.27 (2H, m), 5.37 (2H, s), 6.49 (1H, dd, J = 0.82, 3.30 Hz), 7.06-7.09 (2H, m), 7.13-7.18 (2H, m), 7.28 (1H, d, J = 3.14 Hz), 7.40-7.44 (2H, m)<br>MS (ESI⁺): 440 [M + 1]⁺ |

TABLE 2-3

| Example 23 | 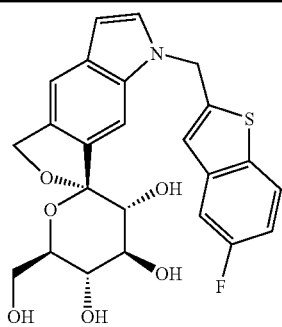 | ¹H-NMR (CD₃OD) δ: 3.45-3.52 (1H, m), 3.62-3.69 (1H, m), 3.75-3.90 (4H, m), 5.20-5.23 (2H, m), 5.71 (2H, s), 6.55 (1H, dd, J = 0.82, 3.30 Hz), 6.98-7.05 (1H, m), 7.22-7.31 (2H, m), 7.40 (1H, d, J = 3.30 Hz), 7.45-7.47 (1H, m), 7.51-7.59 (2H, m)<br>MS (ESI⁺): 472 [M + 1]⁺ |
|---|---|---|
| Example 24 | 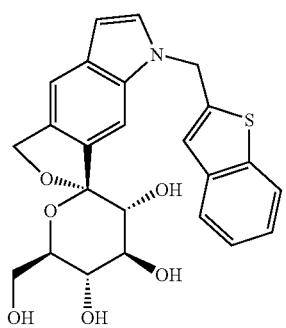 | ¹H-NMR (CD₃OD) δ: 3.47 (1H, t, J = 9.5 Hz), 3.65 (1H, dd, J = 12.1, 5.5 Hz), 3.74-3.89 (4H, m), 5.20 (2H, dd, J = 29.8, 11.5 Hz), 5.67 (2H, s), 6.53 (1H, d, J = 2.6 Hz), 7.16 (1H, s), 7.23-7.31 (2H, m), 7.38 (1H, d, J = 3.3 Hz), 7.47 (2H, d, J = 24.2 Hz), 7.71 (2H, dd, J = 23.2, 7.1 Hz)<br>MS (ESI⁺): 454 [M + 1]⁺ |

TABLE 2-3-continued

| Example 25 | 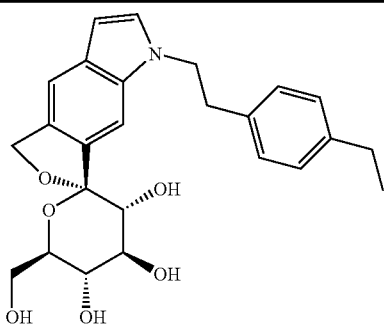 | ¹H-NMR (CD₃OD) δ: 1.19 (3H, t, J = 7.7 Hz), 2.59 (2H, q, J = 7.7 Hz), 3.06 (2H, t, J = 7.1 Hz), 3.54 (1H, dd, J = 9.9, 8.8 Hz), 3.68-3.95 (5H, m), 4.35-4.41 (2H, m), 5.21 (2H, dd, J = 24.7, 11.5 Hz), 6.32 (1H, d, J = 2.6 Hz), 6.98-7.09 (5H, m), 7.38 (1H, s), 7.46 (1H, s)<br>MS (ESI⁺): 440 [M + 1]⁺ |
|---|---|---|
| Example 26 | 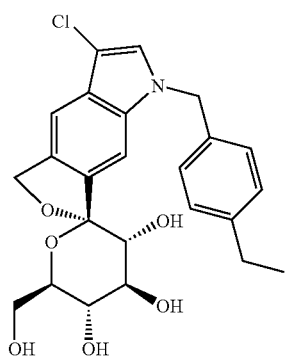 | ¹H-NMR (CD₃OD) δ: 1.19 (3H, t, J = 7.5 Hz), 2.60 (2H, q, J = 7.5 Hz), 3.44-3.52 (1H, m), 3.61-3.72 (1H, m), 3.74-3.88 (4H, m), 5.16-5.30 (2H, m), 5.35 (2H, s), 7.06-7.18 (4H, m) 7.53 (1H, s), 7.41 (1H, s), 7.47 (1H, s)<br>MS (ESI⁺): 460 [M + 1]⁺ |

The compounds listed in Table 3 can be easily produced in the same manner as described in Example 3 or in the production processes, or by making slight modifications to such methods that would be obvious to a person skilled in the art.

TABLE 3

| Example 27 | 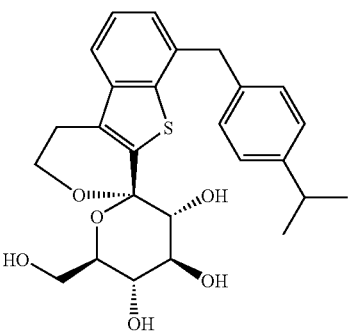 | ¹H-NMR (CD₃OD) δ: 1.21 (6H, d, J = 6.86 Hz), 2.73-2.85 (2H, m), 2.96-3.07 (1H, m), 3.36-3.42 (1H, m), 3.63-3.86 (5H, m), 4.11-4.23 (4H, m), 7.08-7.18 (5H, m), 7.31-7.37 (1H, m), 7.57 (1H, d, J = 7.14 Hz)<br>MS (ESI⁺): 471 [M + 1]⁺ |
|---|---|---|
| Example 28 | 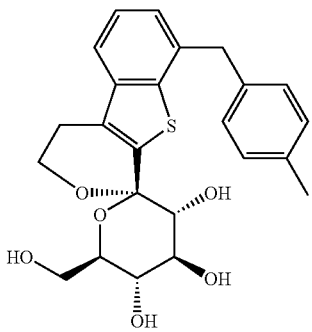 | ¹H-NMR (CD₃OD) δ: 2.27 (3H, s), 2.73-2.80 (1H, m), 2.96-3.07 (1H, m), 3.36-3.42 (1H, m), 3.61-3.86 (5H, m), 4.13-4.21 (4H, m), 7.02-7.11 (4H, m), 7.17 (1H, d, J = 7.14 Hz), 7.31-7.36 (1H, m), 7.56-7.59 (1H, m)<br>MS (ESI⁺): 443 [M + 1]⁺ |

Example 29

(3'R,4'S,5S,5'S,6'R)-3-[(4-ethylphenyl)methyl]-6'-hydroxymethyl-3',4',5',6'-tetrahydro-, spiro[furo[3,4,f]indazole-5(1H,7H),2'-[2H]pyran]-3',4',5'-triol 1) Synthesis of (1S,3'R,4'S,5'S,6'R)-6-acetyl-3',4',5'-tris-benzyloxy-6'-benzyloxymethyl-5-fluoro-3',4',5',6'-tetrahydro-spiro[isobenzofuro-1(3H), 2'-[2H]pyran]

[Formula 63]

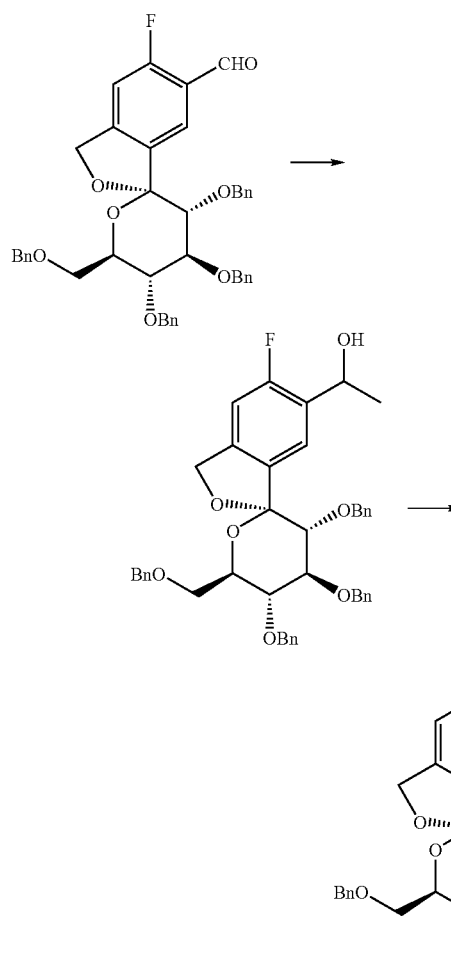

A solution of (1S,3'R,4'S,5'S,6'R)-3',4',5'-tris-benzyloxy-6'-benzyloxymethyl-5-fluoro-6-formyl-3',4,5',6'-tetrahydro-spiro[isobenzofuro-1(3H), 2'-[2H]pyran] (3.6 g, 5.33 mmol) in diethyl ether (10.6 mL) and tetrahydrofuran (3.5 mL) was added dropwise to a solution of methylmagnesium bromide in diethyl ether (0.5 M, 16.0 mL). The reaction solution was stirred for 1 hour at room temperature. Under ice-cooling, saturated aqueous ammonium chloride was added thereto. The resultant mixture was extracted with diethyl ether. The organic layer was then concentrated under reduced pressure, to thereby obtain a crude alcohol product (3.66 g).

This crude alcohol product (3.66 g, 5.29 mmol) was then dissolved in dichloromethane (66 mL), and 4 Å molecular sieve powder (9.2 g) and manganese dioxide (18.4 g, 211.6 mmol) were added thereto. The resultant mixture was stirred for 3.5 hours at room temperature. After filtering, the filtrate was concentrated under reduced pressure, to thereby obtain the titled compound (3.25 mg, 89%).

$^1$H-NMR (CDCl$_3$) δ: 2.61 (3H, d, J=5.1 Hz), 3.62 (1H, dd, J=11.0, 1.8 Hz), 3.75 (1H, dd, J=11.0, 4.0 Hz), 3.82 (1H, t, J=9.7 Hz), 3.88 (1H, d, J=9.5 Hz), 4.06 (1H, dq, J=10.3, 1.8 Hz), 4.13 (1H, t, J=9.3 Hz), 4.21 (1H, d, J=11.4 Hz), 4.45 (1H, d, J=12.1 Hz), 4.56 (1H, d, J=12.4 Hz), 4.62 (3H, t, J=10.4 Hz), 4.87 (1H, d, J=11.0 Hz), 4.92 (2H, s), 5.18 (2H, s), 6.80 (2H, d, J=6.2 Hz), 7.00 (1H, d, J=10.6 Hz), 7.07-7.33 (5H, m), 7.10 (4H, dt, J=14.0, 4.6 Hz), 7.71 (1H, d, J=6.6 Hz).

MS (ESI$^+$): 711 [M 23]$^+$.

2) Synthesis of (1S,3'R,4'S,5'S,6'R)-6-[2-(4-ethylphenyl)-1-oxoethyl]-3',4',5'-tris-benzyloxy-6'-benzyloxymethyl-5-fluoro-3',4',5',6'-tetrahydro-spiro[isobenzofuro-1(3H), 2'-[2H]pyran]

[Formula 64]

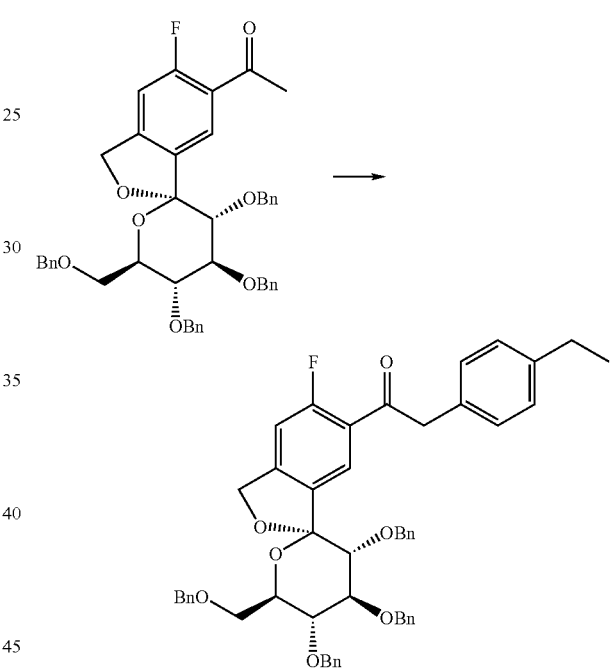

(1S,3'R,4'S,5'S,6'R)-6-acetyl-3',4',5'-tris-benzyloxy-6'-benzyloxymethyl-5-fluoro-3',4',5',6'-tetrahydro-spiro[isobenzofuro-1(3H), 2'-[2H]pyran] (1.2 g, 1.74 mmol) and 4-ethylbromobenzene (0.51 g, 2.78 mmol) were dissolved in toluene (8.7 mL). To the resultant solution were added potassium phosphate (1.29 g, 6.09 mmol), palladium acetate (28.1 mg, 0.12 mmol) and Xantphos (157.2 mg, 0.271 mmol). The mixture was then stirred for 2 hours at 80° C., under a nitrogen atmosphere. The reaction solution was then purified by silica gel flash column chromatography (developing solution=ethyl acetate:n-hexane (1:7)), to thereby obtain the titled compound (0.54 g, 39%).

$^1$H-NMR (CDCl$_3$) δ: 1.17 (3H, t, J=7.7 Hz), 2.55 (2H, q, J=7.4 Hz), 3.62 (1H, d, J=11.0 Hz), 3.75 (1H, dd, J=11.0, 4.0 Hz), 3.80-3.85 (2H, m), 4.04-4.10 (3H, m), 4.21 (2H, d, J=2.2 Hz), 4.45 (1H, d, J=12.1 Hz), 4.54 (1H, d, J=4.8 Hz), 4.58-4.61 (2H, m), 4.87 (2H, d, J=10.6 Hz), 4.90 (1H, s), 5.15 (2H, s), 6.74 (2H, d, J=6.6 Hz), 7.08-7.19 (11H, m), 7.75 (1H, d, J=6.6 Hz).

MS (ESI$^+$): 810 [M+18]$^+$.

3) Synthesis of (3'R,4'S,5S,5'S,6'R)-3',4',5'-tris-benzyloxy-6'-benzyloxymethyl-3-[(4-ethylphenyl)-methyl]-3',4',5',6'-tetrahydro-spiro[furo[3,4,f]indazole-5(1H,7H),2'-[2H]pyran]

[Formula 65]

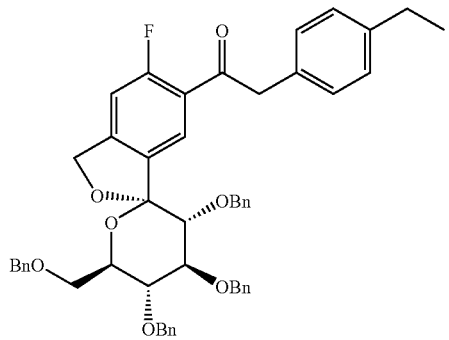

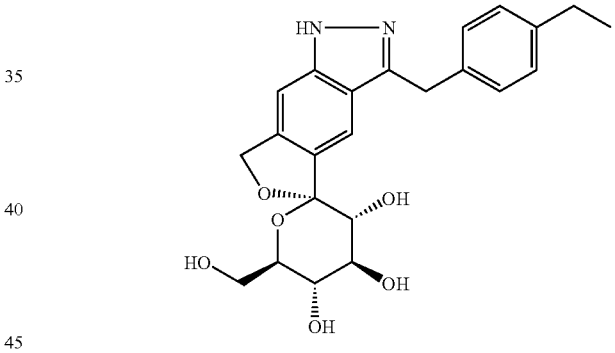

(1S,3'R,4'S,5'S,6'R)-6-[2-(4-ethylphenyl)-1-oxoethyl]-3',4',5'-tris-benzyloxy-6'-benzyloxymethyl-5-fluoro-3',4',5',6'-tetrahydro-spiro[isobenzofuro-1(3H), 2'-[2H]pyran] (0.20 g, 0.252 mmol) and hydrazine (64.3 mg, 2.00 mmol) were stirred in ethylene glycol (0.63 mL) for 4.5 hours at 165° C. Water was added thereto, and the resultant mixture was extracted with ethyl acetate. The organic layer was concentrated under reduced pressure. The resulting residue was purified by silica gel flash column chromatography (developing solution=ethyl acetate:n-hexane (1:3)), to thereby obtain the titled compound (46.1 g, 53%).

$^1$H-NMR (CDCl$_3$) δ: 1.10 (3H, t, J=7.5 Hz), 2.47 (2H, q, J=7.7 Hz), 3.65 (1H, d, J=11.0 Hz), 3.80 (1H, dd, J=11.2, 3.8 Hz), 3.84-3.93 (3H, m), 4.10-4.14 (2H, m), 4.24 (1H, d, J=15.7 Hz), 4.29 (1H, d, J=15.0 Hz), 4.43 (1H, d, J=6.2 Hz), 4.45 (1H, d, J=7.3 Hz), 4.58 (1H, d, J=12.1 Hz), 4.63 (1H, d, J=11.0 Hz), 4.88-4.90 (3H, m), 5.20 (1H, d, J=13.2 Hz), 5.25 (1H, d, J=13.2 Hz), 6.61 (2H, d, J=7.7 Hz), 6.97-6.99 (3H, m), 7.05-7.33 (21H, m).

MS (ESI$^+$): 787 [M+1]$^+$.

4) Synthesis of (3'R,4'S,5S,5'S,6'R)-3-[(4-ethylphenyl)methyl]-6'-hydroxymethyl-3',4,5',6'-tetrahydro-spiro[furo[3,4,f]indazole-5(1H,7H),2'-[2H]pyran]-3',4',5'-triol

[Formula 66]

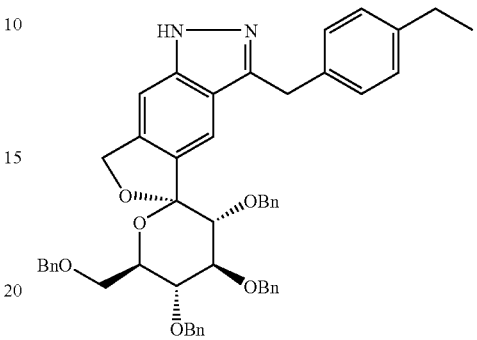

(3'R,4'S,5S,5'S,6'R)-3',4',5'-tris-benzyloxy-6'-benzyloxymethyl-1-[(4-ethylphenyl)-methyl]-3',4',5',6'-tetrahydro-spiro[furo[3,4,f]indazole-5(1H,7H),2'-[2H]pyran] (53.3 mg, 0.067 mmol) was dissolved in dichloromethane (2.25 mL). Pentamethylbenzene (0.15 g, 1.01 mmol) was added thereto, and then the mixture was cooled to −78° C. A solution of boron trichloride in dichloromethane (1.0 M, 0.55 mL) was added dropwise thereto. The mixture was stirred for 3 hours, and then methanol (5 mL) was added. The temperature of the mixture was raised to room temperature, and the reaction mixture was then concentrated under reduced pressure. The resulting residue was purified by silica gel flash column chromatography (developing solution=methanol:dichloromethane (1:6)), to thereby obtain the titled compound (17.8 mg, 61%).

$^1$H-NMR (CD$_3$OD) δ: 1.18 (3H, t, J=7.7 Hz), 2.57 (2H, q, J=7.6 Hz), 3.47 (1H, t, J=9.0 Hz), 3.65 (1H, dd, J=11.9, 5.7 Hz), 3.76-3.83 (4H, m), 4.27 (2H, s), 5.19 (2H, dd, J=27.6, 13.0 Hz), 7.08 (2H, d, J=8.1 Hz), 7.18 (2H, d, J=8.1 Hz), 7.32 (1H, s), 7.57 (1H, s).

MS (ESI$^+$): 427 [M+1]$^+$.

Example 30

(3'R,4'S,5S,5'S,6'R)-3-[(4-ethylphenyl)methyl]-6'-hydroxymethyl-3',4,5',6'-tetrahydro-spiro[furo[3,4,f]benzoisoxazole-5(7H),2'-[2H]pyran]-3',4',5'-triol

1) Synthesis of (3'R,4'S,5S,5'S,6'R)-3',4',5'-tris-benzyloxy-6'-benzyloxymethyl-3-[(4-ethylphenyl)methyl]-3',4',5',6'-tetrahydro-spiro[furo[3,4,f]benzoisoxazole-5(7H),2'-[2H]pyran]

[Formula 67]

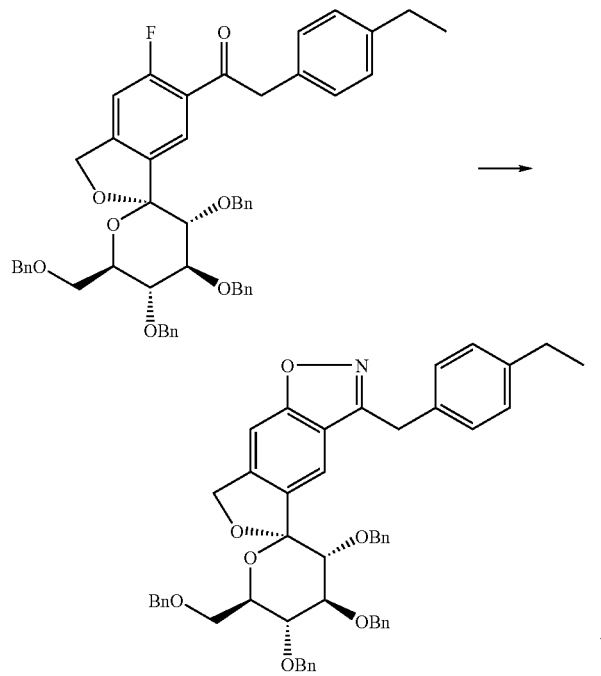

(1S,3'R,4'S,5'S,6'R)-6-[2-(4-ethylphenyl)-1-oxoethyl]-3',4',5'-tris-benzyloxy-6'-benzyloxymethyl-5-fluoro-3',4',5',6'-tetrahydro-spiro[isobenzofuro-1(3H), 2'-[2H]pyran] (0.25 g, 0.315 mmol) was dissolved in pyridine (0.6 mL). Hydroxylamine hydrochloride (35.0 mg, 0.504 mmol) was added thereto, and the mixture was then stirred for 2 hours at 115° C. The solution was cooled to room temperature, and then ethanol (0.8 mL) and potassium hydroxide (112.0 mg, 1.98 mmol) were added thereto. The resultant solution was stirred for 1 hour at 78° C. The reaction solution was purified by silica gel flash column chromatography (developing solution=ethyl acetate:n-hexane (1:6)), to thereby obtain the titled compound (74.9 mg, 30%).

$^1$H-NMR (CDCl$_3$) δ: 1.06 (3H, t, J=7.7 Hz), 2.43 (2H, q, J=7.4 Hz), 3.60 (1H, d, J=11.0 Hz), 3.76 (2H, dd, J=9.5, 4.0 Hz), 3.80-3.85 (2H, m), 4.04 (1H, d, J=9.5 Hz), 4.10 (1H, t, J=9.3 Hz), 4.18 (1H, d, J=15.4 Hz), 4.25 (1H, d, J=16.1 Hz), 4.42 (2H, t, J=10.4 Hz), 4.53 (1H, d, J=12.1 Hz), 4.60 (1H, d, J=10.6 Hz), 4.85-4.88 (3H, m), 5.19 (1H, d, J=13.5 Hz), 5.22 (1H, d, J=14.3 Hz), 6.54 (2H, d, J=7.3 Hz), 6.97 (3H, t, J=7.0 Hz), 7.02-7.09 (2H, m), 7.14-7.17 (5H, m), 7.23-7.33 (14H, m).

MS (ESI$^+$): 788 [M+1]$^+$.

2) Synthesis of (3'R,4'S,5S,5'S,6'R)-3-[(4-ethylphenyl)methyl]-6'-hydroxymethyl-3',4',5',6'-tetrahydrospiro[furo[3,4,f]benzoisoxazole-5(7H),2'-[2H]pyran]-3',4',5'-triol

[Formula 68]

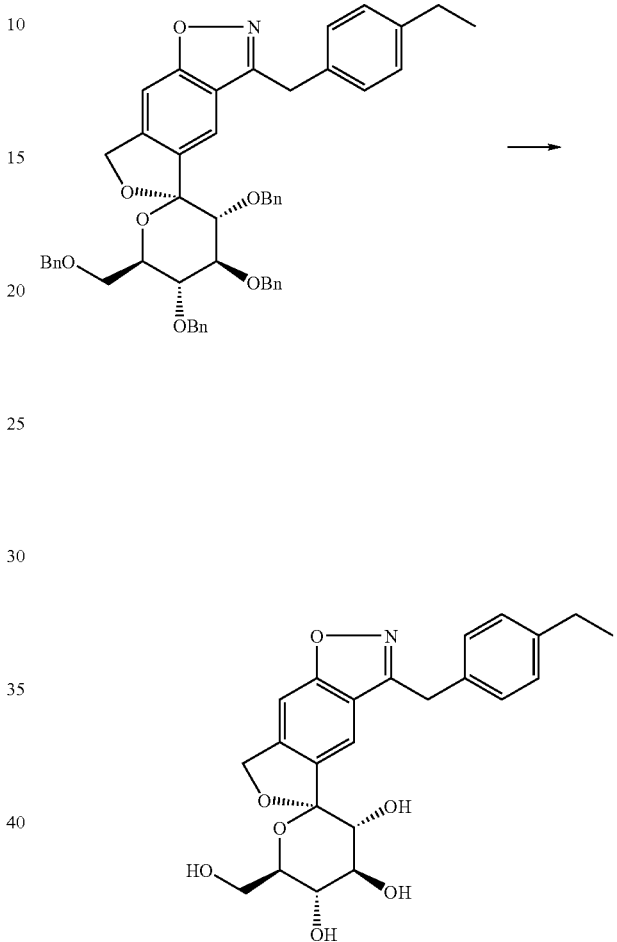

(3'R,4'S,5S,5'S,6'R)-3',4',5'-tris-benzyloxy-6'-benzyloxymethyl-3-[(4-ethylphenyl)methyl]-3',4',5',6'-tetrahydro-spiro[furo[3,4,f]benzoisoxazole-5(7H),2'-[2H]pyran] (86.9 mg, 0.110 mmol) was dissolved in dichloromethane (3.7 mL). Pentamethylbenzene (0.245 g, 1.65 mmol) was added thereto, and then this solution was cooled to –78° C. A solution of boron trichloride in dichloromethane (1.0 M, 0.55 mL) was added dropwise thereto. The resulting mixture was stirred for 2 hours, and then methanol (2.5 mL) was added thereto. The temperature of the mixture was raised to room temperature. The reaction mixture was concentrated under reduced pressure. The resulting residue was purified by silica gel flash column chromatography (developing solution=methanol:dichloromethane (1:12)), to thereby obtain the titled compound (23.0 mg, 48%).

$^1$H-NMR (CD$_3$OD) δ: 1.19 (3H, t, J=7.5 Hz), 2.59 (2H, q, J=7.6 Hz), 3.44-3.49 (1H, m), 3.65 (1H, dd, J=12.1, 5.5 Hz), 3.74-3.82 (4H, m), 4.29 (2H, s), 5.18 (1H, d, J=13.5 Hz), 5.24 (1H, d, J=13.5 Hz), 7.14 (2H, d, J=7.7 Hz), 7.25 (2H, d, J=8.1 Hz), 7.48 (1H, s), 7.59 (1H, s).

MS (ESI$^+$): 428 [M+1]$^+$.

Example 31

(3'R,4'S,5S,5'S,6'R)-3-[(4-ethylphenyl)methyl]-6'-hydroxymethyl-3',4',5',6'-tetrahydro-spiro[furo[3,4,f]benzoisothiazole-5(7H),2'-[2H]pyran]-3',4',5'-triol 1) Synthesis of (1S,3'R,4'S,5'S,6'R)-6-acetyl-3',4',5'-tris-benzyloxy-6'-benzyloxymethyl-5-methylthio-3',4',5',6'-tetrahydro-spiro[isobenzofuro-1(3H), 2'-[2H]pyran]

[Formula 69]

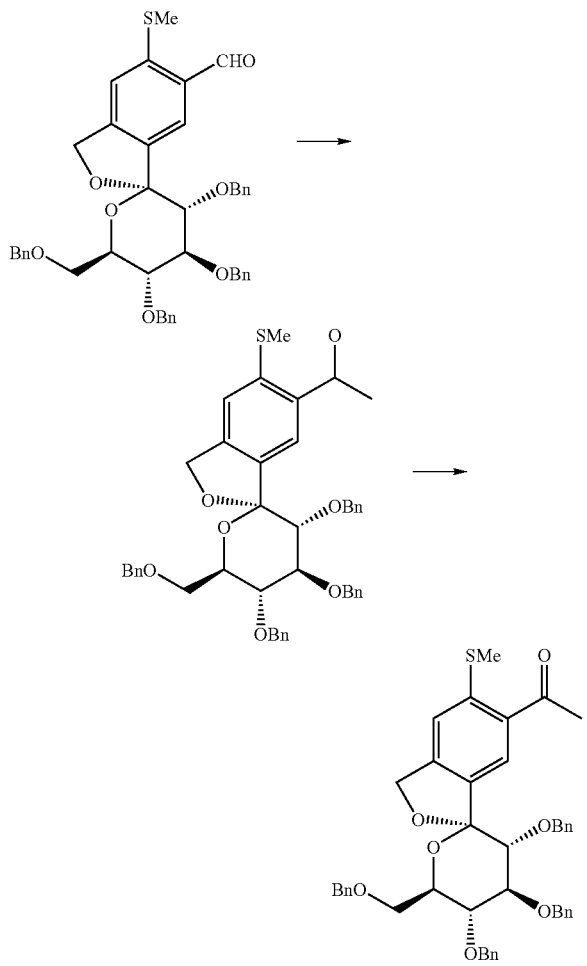

A solution of (1S,3'R,4'S,5'S,6'R)-3',4',5'-tris-benzyloxy-6'-benzyloxymethyl-6-formyl-5-methylthio-3',4',5',6'-tetrahydro-spiro[isobenzofuro-1(3H), 2'-[2H]pyran] (0.25 g, 0.355 mmol) in diethyl ether (0.7 mL) and tetrahydrofuran (0.3 mL) was added dropwise to a solution of methylmagnesium bromide in diethyl ether (0.5 M, 1.08 mL). The reaction mixture was stirred for 4 hours at room temperature. Under ice-cooling, saturated aqueous ammonium chloride was added thereto, and the resultant mixture was extracted with ethyl acetate. The organic layer was then concentrated under reduced pressure, to thereby obtain a crude alcohol product (0.27 g).

This crude alcohol product (3.66 g, 5.29 mmol) was then dissolved in dichloromethane (4.5 mL), and 4 Å molecular sieve powder (0.15 g) and manganese dioxide (1.20 g, 13.8 mmol) were added thereto. The resultant mixture was stirred for 2.5 hours at room temperature. After filtering, the filtrate was concentrated under reduced pressure, and the resulting residue was purified by silica gel flash column chromatography (developing solution=ethyl acetate:n-hexane (1:4.5)), to thereby obtain the titled compound (165.5 mg, 64%).

$^1$H-NMR (CDCl$_3$) δ: 2.43 (3H, s), 2.44 (3H, s), 3.62 (1H, d, J=9.2 Hz), 3.78 (1H, dd, J=11.0, 3.7 Hz), 3.84 (2H, t, J=10.4 Hz), 4.05-4.17 (2H, m), 4.28 (1H, d, J=11.7 Hz), 4.45 (1H, d, J=12.1 Hz), 4.54 (1H, d, J=12.1 Hz), 4.60 (1H, d, J=5.1 Hz), 4.63 (1H, d, J=4.4 Hz), 4.87 (1H, d, J=10.6 Hz), 4.94 (2H, s), 5.19 (2H, s), 6.75 (2H, d, J=7.0 Hz), 7.01-7.10 (3H, m), 7.15-7.19 (3H, m), 7.24-7.33 (41H, m), 7.44 (1H, s).

MS (ESI$^+$): 717 [M+1]$^+$.

2) Synthesis of (1S,3'R,4'S,5'S,6'R)-6-[2-(4-ethylphenyl)-1-oxoethyl]-3',4',5'-tris-benzyloxy-6'-benzyloxymethyl-5-methylthio-3',4',5',6'-tetrahydro-spiro[isobenzofuro-1(3H), 2'-[2H]pyran]

[Formula 70]

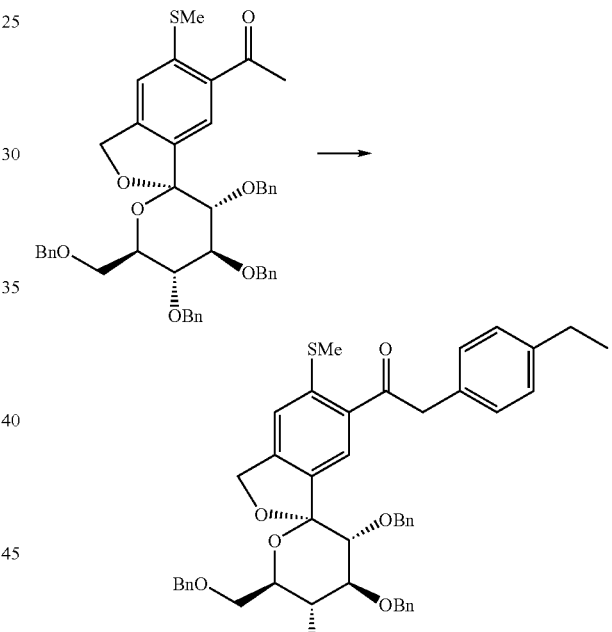

(1S,3'R,4'S,5'S,6'R)-6-acetyl-3',4',5'-tris-benzyloxy-6'-benzyloxymethyl-5-methylthio-3',4',5',6'-tetrahydro-spiro[isobenzofuro-1(3H), 2'-[2H]pyran] (0.165 g, 0.230 mmol) and 4-ethylbromobenzene (68.3 mg, 0.369 mmol) were dissolved in toluene (1.1 mL). To the resultant solution were added potassium phosphate (0.177 g, 0.807 mmol), palladium acetate (3.8 mg, 0.016 mmol) and Xantphos (20.8 mg, 0.036 mmol). The mixture was then stirred for 2 hours at 80° C. under a nitrogen atmosphere. The reaction mixture was then purified by silica gel flash column chromatography (developing solution=ethyl acetate:n-hexane (1:4)), to thereby obtain the titled compound (61.3 mg, 32%).

$^1$H-NMR (CDCl$_3$) δ: 1.11 (3H, t, J=7.7 Hz), 2.44 (3H, s), 2.48 (2H, q, J=22.7 Hz), 3.66 (1H, d, J=9.2 Hz), 3.79-3.83 (2H, m), 3.87 (1H, d, J=9.9 Hz), 3.92 (1H, d, J=11.4 Hz), 4.11-4.16 (4H, m), 4.48 (2H, dd, J=11.7, 4.0 Hz), 4.59 (1H, d, J=12.1 Hz), 4.66 (1H, d, J=10.6 Hz), 4.90-4.93 (3H, m), 5.18-5.19 (2H, m), 6.67 (1H, d, J=7.0 Hz), 7.03-7.23 (11H, m), 7.31-7.34 (13H, m), 7.66 (1H, s).

MS (ESI+): 821 [M+1]+.

3) Synthesis of (3'R,4'S,5S,5'S,6'R)-3',4',5'-tris-benzyloxy-6'-benzyloxymethyl-3-[(4-ethylphenyl)-methyl]-3',4',5',6'-tetrahydro-spiro[furo[3,4,f]benzothiazole-5(7H),2'-[2H]pyran]

[Formula 71]

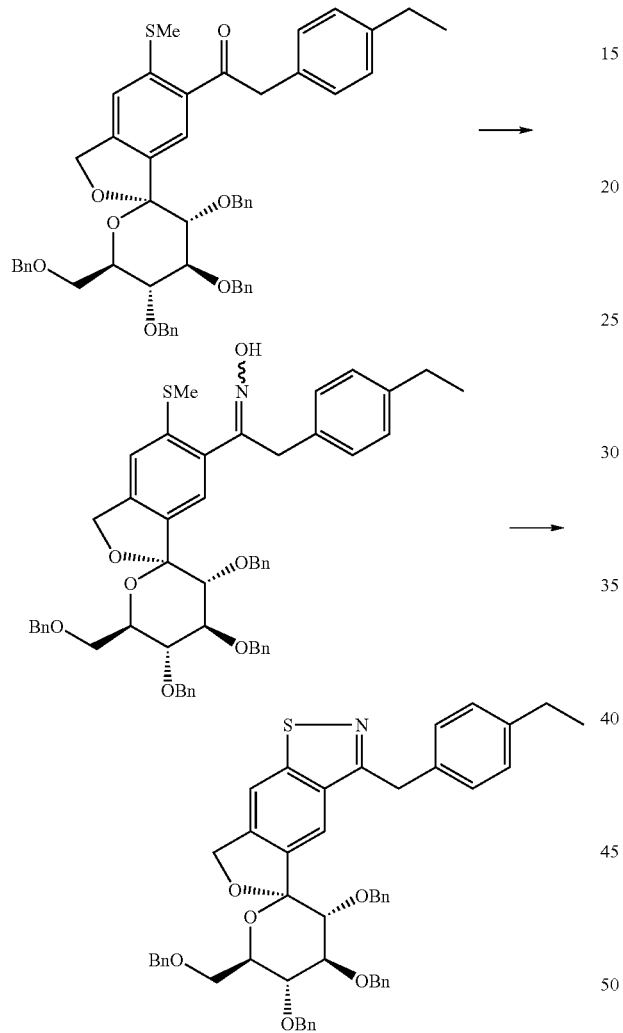

(1S,3'R,4'S,5'S,6'R)-6-[2-(4-ethylphenyl)-1-oxoethyl]-3', 4',5'-tris-benzyloxy-6'-benzyloxymethyl-5-methylthio-3',4', 5',6'-tetrahydro-spiro[isobenzofuro-1(3H), 2'-[2H]pyran] (0.060 g, 0.073 mmol) was dissolved in pyridine (0.15 mL). Hydroxylamine hydrochloride (9.0 mg, 0.124 mmol) was added thereto, and the mixture was then stirred for 2 hours at 115° C. The reaction mixture was washed with 1 N hydrochloric acid, and the resultant mixture was extracted with dichloromethane. The organic layer was then concentrated under reduced pressure, to thereby obtain a crude oxime product. To this crude oxime product was added acetic anhydride (0.030 mL, 0.31 mmol), and the resultant solution was stirred for 18 hours at 115° C. The solution was cooled to room temperature, and then saturated aqueous sodium hydrogen chloride was added thereto. The resultant mixture was extracted with dichloromethane. The organic layer was then concentrated under reduced pressure, and the resulting residue was purified by silica gel flash column chromatography (developing solution=ethyl acetate:n-hexane (1:5)), to thereby obtain the titled compound (6.7 mg, 11%).

$^1$H-NMR (CDCl$_3$) δ: 1.08 (3H, t, J=7.5 Hz), 2.44 (2H, q, J=7.7 Hz), 3.65 (1H, d, J=9.5 Hz), 3.81 (1H, dd, J=11.0, 3.7 Hz), 3.84-3.92 (3H, m), 4.11-4.16 (2H, m), 4.33-4.47 (4H, m), 4.57 (1H, d, J=12.1 Hz), 4.65 (1H, d, J=10.6 Hz), 4.90-4.91 (3H, m), 5.27 (2H, s), 6.53 (1H, d, J=7.0 Hz), 6.95 (4H, dd, J=15.6, 7.9 Hz), 7.14 (2H, d, J=8.1 Hz), 7.20-7.33 (18H, m), 7.73 (1H, s).

MS (ESI+): 804 [M+1]+.

4) Synthesis of (3'R,4'S,5S,5'S,6'R)-3-[(4-ethylphenyl)methyl]-6'-hydroxymethyl-3',4',5',6'-tetrahydro-spiro[furo[3,4,f]benzoisothiazole-5(7H),2'-[2H]pyran]-3',4',5'-triol

[Formula 72]

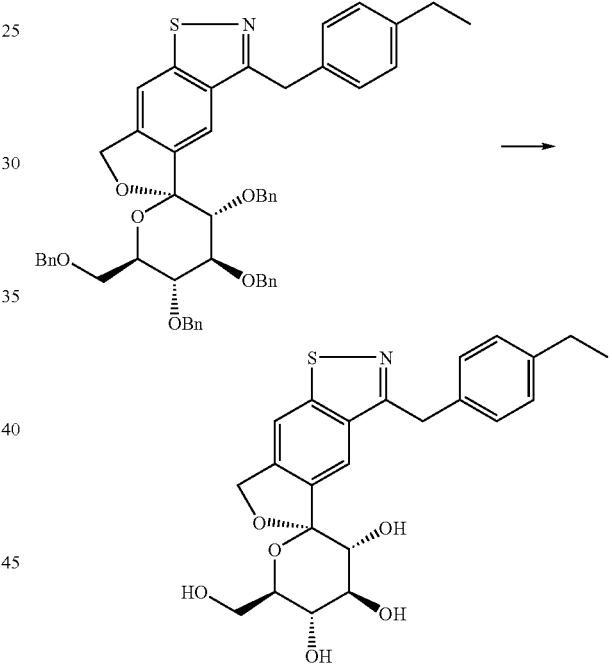

(3'R,4'S,5S,5'S,6'R)-3',4',5'-tris-benzyloxy-6'-benzyloxymethyl-3-[(4-ethylphenyl)-methyl]-3',4',5',6'-tetrahydro-spiro[furo[3,4,f]benzothiazole-5(7H),2'-[2H]pyran] (6.7 mg, 0.013 mmol) was dissolved in dichloromethane (0.45 mL). To the resultant solution was added pentamethylbenzene (30.2 mg, 0.204 mmol), and then the mixture was cooled to −78° C. A solution of boron trichloride in dichloromethane (1.0 M, 0.11 mL) was added dropwise thereto. The mixture was stirred for 2 hours, and then methanol (0.3 mL) was added thereto. The temperature of the mixture was raised to room temperature. The reaction mixture was then concentrated under reduced pressure, and the resulting residue was purified by silica gel flash column chromatography (developing solution=methanol:dichloromethane (1:12)), to thereby obtain the titled compound (2.0 mg, 33%).

$^1$H-NMR (CD$_3$OD) δ: 1.18 (3H, t, J=7.7 Hz), 2.58 (2H, q, J=7.6 Hz), 3.51 (1H, t, J=9.5 Hz), 3.67 (1H, dd, J=11.7, 5.5

Hz), 3.77-3.88 (4H, m), 4.45 (2H, s), 5.21 (1H, d, J=13.5 Hz), 5.27 (1H, d, J=13.5 Hz), 7.10 (2H, d, J=7.0 Hz), 7.21 (2H, d, J=7.0 Hz), 7.91 (1H, s), 8.06 (1H, s).

MS (ESI$^+$): 444 [M+1]$^+$.

Example 32

(3S,3'R,4'S,5'S,6'R)-5-[(4-ethylphenyl)methyl]-6'-hydroxymethyl-3',4',5',6'-tetrahydro-spiro[benz[g]isobenzofuro-3(1H),2'-[2H]pyran]-3',4',5'-triol

1) Synthesis of naphthalene-1,4-dicarboxylic acid diisopropyl ester

[Formula 73]

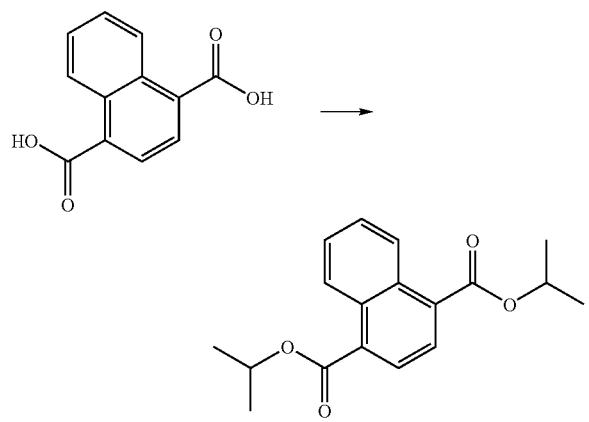

Under a nitrogen stream, sulfuric acid (8 mL) was added dropwise over 3 hours to a solution of naphthalene-1,4-dicarboxylic acid (1.107 g, 5.12 mmol) in 2-propanol (60 mL) while heating to reflux. The resultant solution was cooled to room temperature and then saturated aqueous sodium carbonate was added thereto. The mixture was then stirred for 10 minutes at room temperature. The resultant mixture was twice extracted with dichloromethane. After drying the organic layer over anhydrous magnesium sulfate, solvent was removed by distillation under reduced pressure. The resulting residue was purified by silica gel column chromatography (developing solution=ethyl acetate:n-hexane (15:85)), to thereby obtain the titled compound (588 mg, 38%).

$^1$H-NMR (CDCl$_3$) δ: 1.46 (12H, d, J=6.31 Hz), 5.35-5.43 (2H, m), 7.60-7.65 (2H, m), 8.03 (2H, s), 8.77-8.81 (2H, m).

2) Synthesis of 2-trimethylsilanyl-naphthalene-1,4-dicarboxylic acid diisopropyl ester

[Formula 74]

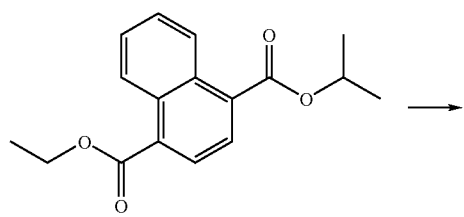

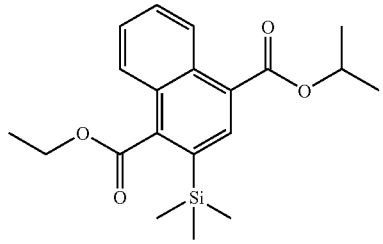

Under a nitrogen stream, to a solution of tetramethylpiperidine (0.39 mL, 2.311 mmol) in THF (1.8 mL) was added a solution of n-butyllithium in n-hexane (2.67 M, 0.87 mL, 2.323 mmol) under ice cooling, and the resultant solution was stirred for 10 minutes at the same temperature. The solution was cooled to −78° C., and then chlorotrimethylsilane (2.47 mL, 19.325 mmol) and a solution of naphthalene-1,4-dicarboxylic acid diisopropyl ester (0.58 g, 1.931 mmol) in THF (2 mL) were added thereto. The temperature of the solution was raised over 1 hour to room temperature, and then to the solution was added saturated aqueous ammonium chloride to stop the reaction. The resultant mixture was twice extracted with dichloromethane. After drying the organic layer over anhydrous magnesium sulfate, solvent was removed by distillation under reduced pressure. The resulting residue was purified by silica gel column chromatography (developing solution=ethyl acetate:n-hexane (1:9)), to thereby obtain the titled compound (246 mg, 34%).

$^1$H-NMR (CDCl$_3$) δ: 0.40 (9H, s), 1.45-1.50 (12H, m), 5.34-5.46 (2H, m), 7.51-7.63 (2H, m), 7.87-7.90 (1H, m), 8.22 (1H, s), 8.76-8.79 (1H, m)

3) Synthesis of 2-bromo-naphthalene-1,4-dicarboxylic acid diisopropyl ester

[Formula 75]

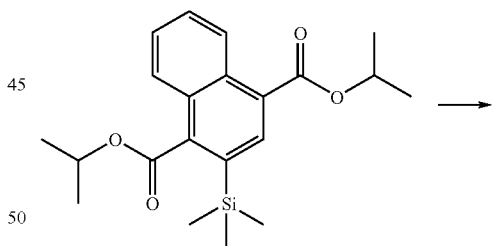

Under a nitrogen stream, a mixture of diisopropyl 2-trimethylsilanyl-naphthalene-1,4-dicarboxylic acid diisopropyl ester (0.25 g, 0.671 mmol), N-bromosuccinimide (179 mg, 1.006 mmol) and acetonitrile (12.5 mL) was stirred for 30 minutes at 150° C. under microwave irradiation. The reaction mixture was concentrated under reduced pressure, and the resulting residue was purified by silica gel flash column chromatography (developing solution=ethyl acetate:n-hexane (1:9)), to thereby obtain the titled compound (209 mg, 82%).

$^1$H-NMR (CDCl$_3$) δ: 1.44-1.49 (12H, m), 5.32-5.54 (2H, m), 7.56-7.67 (2H, m), 7.74-7.78 (1H, m), 8.20 (1H, s), 8.42-8.87 (1H, m).

4) Synthesis of (2-bromo-4-hydroxymethyl-naphthalene-1-yl)-methanol

[Formula 76]

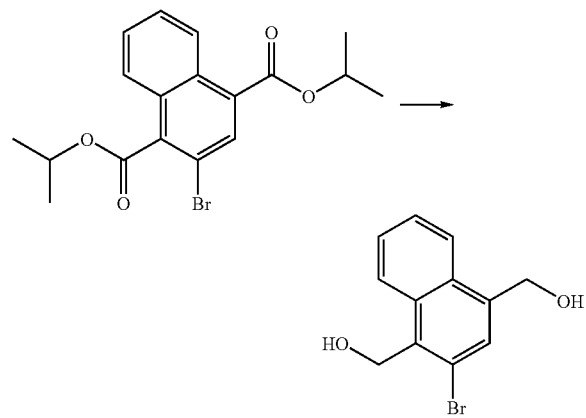

Under a nitrogen stream, to a solution of 2-bromo-naphthalene-1,4-dicarboxylic acid diisopropyl ester (191.5 mg, 0.505 mmol) in dichloromethane (1.9 mL) was added a solution of diisobutylaluminum hydride in toluene (1.04 M, 4.9 mL, 5.096 mmol) at −78° C. The temperature of the resultant mixture was raised over 2 hours to 0° C., and then to the solution was added saturated aqueous ammonium chloride to stop the reaction. The resultant mixture was twice extracted with ethyl acetate. After drying the organic layer over anhydrous magnesium sulfate, solvent was removed by distillation under reduced pressure. The resulting residue was purified by silica gel column chromatography (developing solution=ethyl acetate:n-hexane (1:1)), to thereby obtain the titled compound (124 mg, 87%).

$^1$H-NMR (CD$_3$OD) δ: 5.05 (2H, d, J=1.10 Hz), 5.24 (2H, s), 7.53-7.62 (2H, m), 7.74 (1H, s), 8.04-8.07 (1H, m), 8.28-8.32 (1H, m).

5) Synthesis of 2-bromo-1,4-bis-[(1-methoxy-1-methylethoxy)methyl]-naphthalene

[Formula 77]

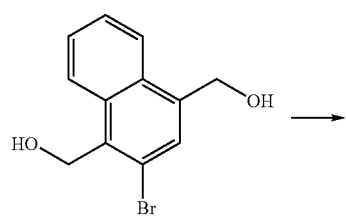

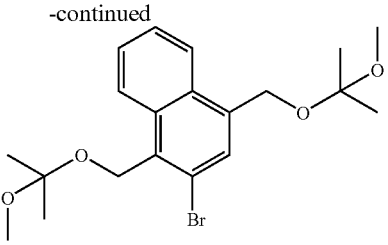

Under a nitrogen stream, to a solution of (2-bromo-4-hydroxymethyl-naphthalen-1-yl)-methanol (124 mg, 0.464 mmol) and pyridinium p-toluenesulfonate (3 mg, 0.012 mmol) in THF (5 mL) was added 2-methoxypropene (0.134 mL, 1.399 mmol) under ice cooling, and the resultant mixture was stirred at the same temperature for 1 hour. Saturated aqueous potassium carbonate was added thereto, and the resultant mixture was twice extracted with ethyl acetate. The organic layer was washed with saturated brine and dried (anhydrous magnesium sulfate). Solvent was then removed by distillation under reduced pressure, to thereby obtain the titled compound (191 mg, 100%).

$^1$H-NMR (CDCl$_3$) δ: 1.51 (6H, s), 1.52 (6H, s), 3.27 (3H, s), 3.38 (3H, s), 4.92 (2H, d, J=0.82 Hz), 5.11 (2H, s), 7.51-7.59 (2H, m), 7.77 (1H, s), 7.94-7.97 (1H, m), 8.20-8.23 (1H, m).

6) Synthesis of (3S,3'R,4'S,5'S,6'R)-3',4',5'-tris-benzyloxy-6'-benzyloxymethyl-5-hydroxymethyl-3',4',5',6'-tetrahydro-spiro[benz[g]isobenzofuro-3(1H),2'-[2H]pyran]

[Formula 78]

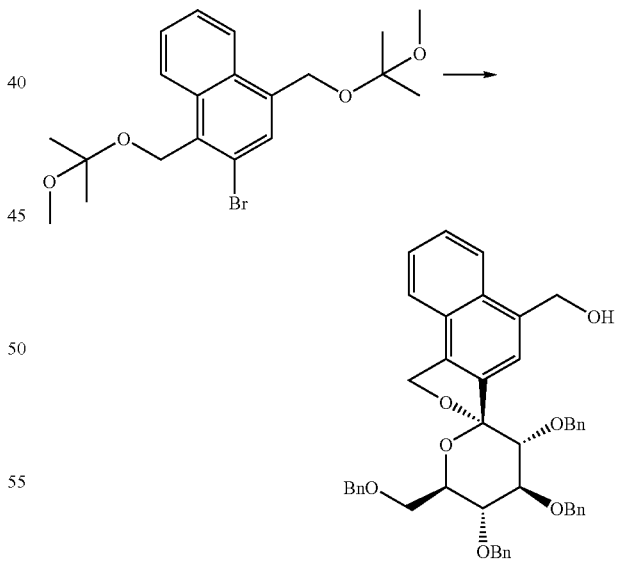

Under a nitrogen stream, a solution of 2-bromo-1,4-bis-[(1-methoxy-1-methylethoxy)methyl]-naphthalene (191 mg, 0.464 mmol) in THF (2 mL) was cooled to −78° C., and a solution of n-butyllithium in n-hexane (2.67 M, 0.21 mL, 0.561 mmol) was added dropwise thereto. The reaction mixture was stirred for 10 minutes at the same temperature. A solution (1 mL) of 3,4,5-tris-benzyloxy-6-(benzyloxymethyl)-tetrahydro-pyran-2-one (0.35 g, 0.65 mmol) in THF was added dropwise to the solution at −78° C. The resultant mixture was stirred for 2 hours at the same temperature, and then saturated aqueous ammonium chloride (3 mL) and water (1 mL) were added thereto to stop the reaction. The resultant mixture was extracted with ethyl acetate. The organic layer was washed with saturated aqueous ammonium chloride (40 mL) and then dried over sodium sulfate. Solvent was then removed by distillation under reduced pressure. To the resulting residue were added THF (1 mL), methanol (1 mL) and p-toluenesulfonic acid (18 mg, 0.095 mmol), and the resultant solution was heated to reflux for 2 hours. Solvent was then removed by distillation under reduced pressure, and the resulting residue was purified by silica gel flash column chromatography (developing solution=ethyl acetate:n-hexane (3:7)), to thereby obtain the titled compound (183 mg, 56%).

$^1$H-NMR (CDCl$_3$) δ: 3.66 (1H, d, J=9.33 Hz), 3.80-4.25 (6H, m), 4.43-4.67 (4H, m), 4.90-5.07 (5H, m), 5.57 (2H, s), 6.65 (2H, d, J=6.86 Hz), 6.86-6.91 (2H, m), 7.01-7.06 (1H, m), 7.20-7.34 (16H, m), 7.59-7.70 (3H, m), 8.15 (1H, d, J=9.33 Hz).

7) Synthesis of (3S,3'R,4'S,5'S,6'R)-3',4',5'-tris-benzyloxy-6'-benzyloxymethyl-5-chloromethyl-3',4',5',6'-tetrahydro-spiro[benz[g]isobenzofuro-3(1H),2'-[2H]pyran]

[Formula 79]

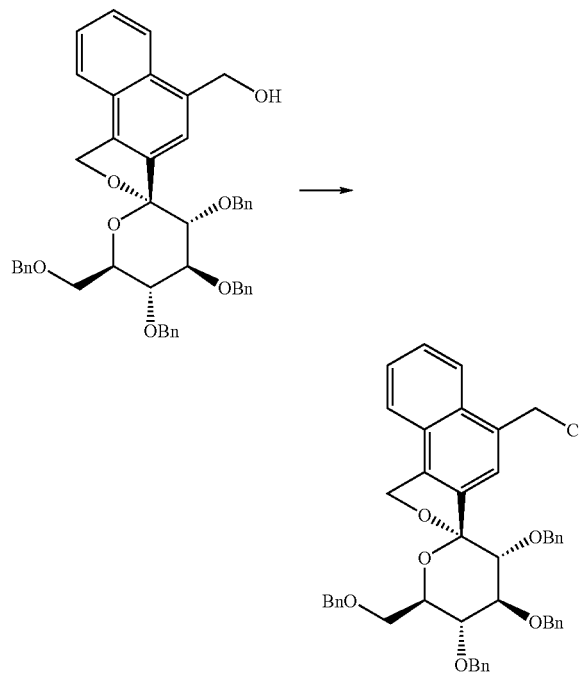

Under a nitrogen stream, to a solution of (3S,3'R,4'S,5'S,6'R)-3',4',5'-tris-benzyloxy-6'-benzyloxymethyl-5-hydroxymethyl-3',4',5',6'-tetrahydro-spiro[benz[g]isobenzofuro-3(1H),2'-[2H]pyran] (183 mg, 0.258 mmol) in dichloromethane (3 mL) were added triphenylphosphine (0.34 g, 1.296 mmol) and carbon tetrachloride (0.12 mL, 1.244 mmol) at room temperature. The resultant mixture was then stirred for 1.5 hours at the same temperature. Solvent was removed by distillation under reduced pressure, and the resulting residue was purified by silica gel flash column chromatography (developing solution=ethyl acetate:n-hexane (1:3)), to thereby obtain the titled compound (156 mg, 83%).

$^1$H-NMR (CDCl$_3$) δ: 3.66 (1H, dd, J=1.65, 10.98 Hz), 3.80-3.99 (3H, m), 4.12-4.24 (3H, m), 4.46-4.68 (4H, m), 4.90-5.06 (5H, m), 5.56 (2H, dd, J=13.17, 15.37 Hz), 6.64-6.67 (2H, m), 6.88-6.94 (2H, m), 7.02-7.07 (1H, m), 7.20-7.37 (16H, m), 7.58-7.70 (3H, m), 8.19-8.22 (1H, m).

8) Synthesis of (3S,3'R,4'S,5'S,6'R)-3',4',5'-tris-benzyloxy-6'-benzyloxymethyl-5-[(4-ethylphenyl)methyl]-3',4',5',6'-tetrahydro-spiro[benz[g]isobenzofuro-3(1H),2'-[2H]pyran]

[Formula 80]

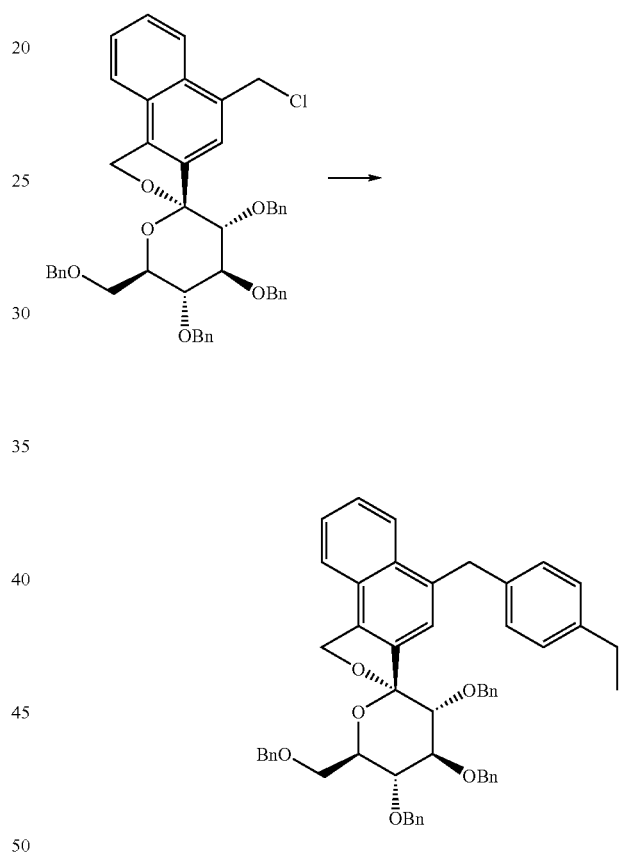

Under a nitrogen stream, a mixture of (3S,3'R,4'S,5'S,6'R)-3',4',5'-tris-benzyloxy-6'-benzyloxymethyl-5-chloromethyl-3',4',5',6'-tetrahydro-spiro[benz[g]isobenzofuro-3(1H),2'-[2H]pyran] (81 mg, 0.111 mmol), 4-ethylphenylboronic acid (33 mg, 0.22 mmol), sodium carbonate (35 mg, 0.330 mmol), tetrakis triphenylphosphine palladium(0) (6 mg, 0.005 mmol), tetrabutylammonium bromide (7 mg, 0.022 mmol), N,N-dimethylformamide (0.51 mL) and water (27 μL) was stirred for 20 minutes at 140° C. under microwave irradiation. The reaction mixture was purified by silica gel flash column chromatography (developing solution=ethyl acetate:n-hexane (1:4)), to thereby obtain the titled compound (61 mg, 69%).

$^1$H-NMR (CDCl$_3$) δ: 1.17 (3H, t, J=7.55 Hz), 2.56 (2H, q, J=7.55 Hz), 3.66-3.70 (1H, m), 3.81-4.23 (6H, m), 4.41-4.68 (6H, m), 4.89-4.97 (3H, m), 5.58 (2H, dd, J=12.63, 18.66 Hz), 6.65 (2H, d, J=7.14 Hz), 6.91-7.09 (7H, m), 7.20-7.33 (16H, m), 7.50-7.56 (2H, m), 7.66-7.69 (1H, m), 8.05-8.08 (1H, m).

9) Synthesis of (3S,3'R,4'S,5'S,6'R)-5-[(4-ethylphenyl)methyl]-6'-hydroxymethyl-3',4',5',6'-tetrahydro-spiro[benz[g]isobenzofuro-3(1H),2'-[2H]pyran]-3',4',5'-triol

[Formula 81]

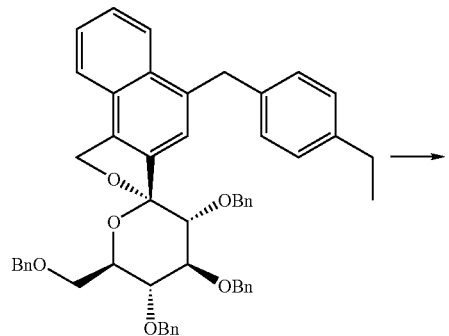

Under a nitrogen stream, to a solution of (3S,3'R,4'S,5'S,6'R)-3',4',5'-tris-benzyloxy-6'-benzyloxymethyl-5-[(4-ethylphenyl)methyl]-3',4',5',6'-tetrahydro-spiro[benz[g]isobenzofuro-3(1H),2'-[2H]pyran] (61 mg, 0.077 mmol) and pentamethylbenzene (113 mg, 0.762 mmol) in dichloromethane (4.2 mL) was added a solution of boron trichloride in dichloromethane (1.0 M, 0.38 mL, 0.38 mmol) at −78° C., and the resultant mixture was stirred for 2 hours at the same temperature. Methanol (4.2 mL) was added thereto, and then the temperature of the solution was raised to room temperature. Saturated aqueous sodium hydrogen carbonate was added thereto, and the resultant mixture was extracted with ethyl acetate. After drying (anhydrous potassium carbonate), solvent was removed by distillation under reduced pressure. The resulting residue was purified by silica gel column chromatography (developing solution=dichloromethane:methanol (9:1)), to thereby obtain the titled compound (25 mg, 76%).

$^1$H-NMR (CD$_3$OD) δ: 1.18 (3H, t, J=7.69 Hz), 2.57 (2H, q, J=7.69 Hz), 3.47-3.53 (1H, m), 3.66-3.93 (5H, m), 4.44 (2H, s), 5.48-5.58 (2H, m), 7.07 (4H, dd, J=8.23, 14.27 Hz), 7.36 (1H, s), 7.44-7.53 (2H, m), 7.70-7.73 (1H, m), 8.05-8.08 (1H, m).

MS (ESI$^+$): 436 [M+1]$^+$.

HPLC retention time: 12.5 minutes
<HPLC Measurement Conditions>
Column: YMC-Pack ODS-A 6.0×150 mm, 5 μm Mobile phase: Eluted under gradient from 0.1% TFA/MeCN (5%)+0.1% TFA/H$_2$O (95%) to 0.1% TFA/MeCN (100%) over 20 minutes, and then under the same conditions (0.1% TFA/MeCN (100%)) for 5 minutes.

Flow rate: 1.5 mL/min

Column temperature: Room temperature

Detection conditions: Total plot over all wavelengths from 230 to 400 nm

Example 33

(3'R,4'S,5'S,6'R,8S)-1-[(4-ethylphenyl)methyl]-6'-hydroxymethyl-3',4',5',6'-tetrahydro-spiro[furo[3,4,g]naphthalene-8(6H),2'-[2H]pyran]-3',4',5'-triol 1) Synthesis of methyl 5-[(4-ethylphenyl)methyl]-3-hydroxy-2-naphthoate

[Formula 82]

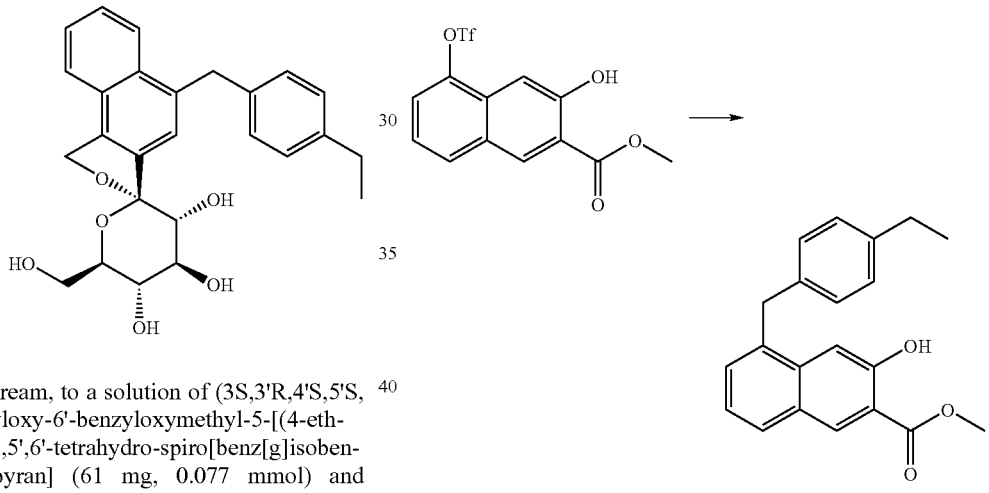

Under a nitrogen stream, the known compound methyl 3-hydroxy-5-trifluoromethanesulfonyloxy-2-naphthoate (Bull. Korean Chem. Soc. 2000, 21, 757; 82.3 mg, 0.23 mmol), diphenylphosphino ferrocene palladium dichloride (17.3 mg, 0.021 mmol), 2-[(4-ethylphenyl)methyl]-4,4,5,5-tetramethyl-[1,3,2]dioxaborane (57.8 mg, 0.24 mmol) and cesium carbonate (228.6 mg, 0.70 mmol) were dissolved in tetrahydrofuran (2.0 mL). Water (0.2 mL) was added thereto, and then the mixture was stirred for 30 minutes at 100° C. in a microwave apparatus. Water was added thereto, and the resultant mixture was extracted with ethyl acetate. The organic layer was washed with 1 N hydrochloric acid and saturated brine, dried over anhydrous magnesium sulfate, and then concentrated under reduced pressure. The resulting residue was purified by silica gel flash column chromatography (developing solution=ethyl acetate:n-hexane (1:20)), to thereby obtain the titled compound (55.8 mg, 74%).

$^1$H-NMR (DMSO) δ: 1.13 (3H, t, J=7.6 Hz), 2.53 (2H, q, J=7.6 Hz), 3.32 (3H, s), 4.28 (2H, s), 7.10 (2H, d, J=8.4 Hz), 7.12 (2H, d, J=8.4 Hz), 7.32 (1H, dd, J=7.8, 7.8 Hz), 7.40-7.45 (2H, m), 7.87 (1H, d, J=7.8 Hz), 8.48 (1H, s), 10.22 (1H, s).

2) Synthesis of methyl 5-[(4-ethylphenyl)methyl]-3-trifluoromethanesulfonyloxy-2-naphthoate

[Formula 83]

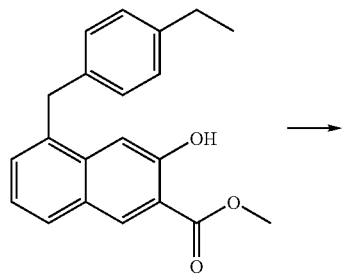

↓

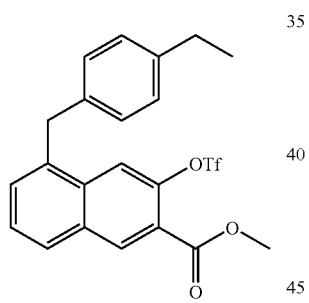

Under a nitrogen stream, methyl 5-[(4-ethylphenyl)methyl]-3-hydroxy-2-naphthoate (680.1 mg, 2.12 mmol) was dissolved in dichloromethane (12.0 mL). To this solution were then added pyridine (0.35 mL, 4.24 mmol) and trifluoromethanoic acid anhydride (0.43 mL, 2.54 mmol) at 0° C. The resultant solution was stirred for 17 hours while the temperature was allowed to spontaneously rise, and was then 1 N hydrochloric acid was added thereto. The resultant mixture was extracted with dichloromethane. The organic layer was washed with saturated aqueous sodium hydrogen carbonate and saturated brine, dried over anhydrous magnesium sulfate, and then concentrated under reduced pressure. The resulting residue was purified by silica gel flash column chromatography (developing solution=ethyl acetate:n-hexane (1:20)), to thereby obtain the titled compound (791.1 mg, 82%).

$^1$H-NMR (DMSO) δ: 1.11 (3H, t, J=7.7 Hz), 2.52 (2H, q, J=7.7 Hz), 3.92 (3H, s), 4.43 (2H, s), 7.08-7.13 (4H, m), 7.70-7.74 (2H, m), 8.03 (1H, s), 8.15-8.18 (1H, m), 8.80 (1H, s).

3) Synthesis of methyl 5-[(4-ethylphenyl)methyl]-3-(4,4,5,5-tetramethyl-[1,3,2]dioxaboran-2-yl)-2-naphthoate

[Formula 84]

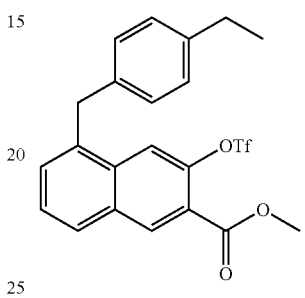

↓

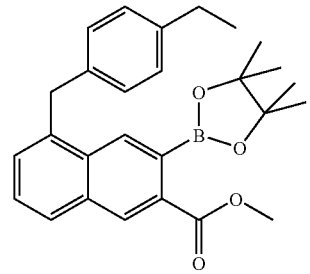

Under a nitrogen stream, methyl 5-[(4-ethylphenyl)methyl]-3-trifluoromethanesulfonyloxy-2-naphthoate (791.1 mg, 1.75 mmol), diphenylphosphino ferrocene palladium dichloride (42.7 mg, 0.052 mmol) and triethylamine (0.73 mL, 5.25 mmol) were dissolved in dioxane (15.0 mL). To the resultant solution was added 4,4,5,5-tetramethyl-[1,3,2]dioxaborane (0.76 mL, 5.25 mmol), and then this mixture was stirred for 3 hours at 100° C. The reaction mixture was passed through silica gel, and then concentrated under reduced pressure. The resulting residue was purified by silica gel flash column chromatography (developing solution=ethyl acetate: n-hexane (1:10)), to thereby obtain the titled compound (594.5 mg, 79%).

$^1$H-NMR (CDCl$_3$) δ: 1.21 (3H, t, J=7.5 Hz), 1.42 (12H, s), 2.61 (2H, q, J=7.5 Hz), 3.96 (3H, s), 4.43 (2H, s), 7.10 (2H, d,

J=8.4 Hz), 7.13 (2H, d, J=8.4 Hz), 7.32 (1H, d, J=7.6 Hz), 7.44 (1H, dd, J=7.6, 7.6 Hz), 7.79 (1H, d, J=7.6 Hz), 8.18 (1H, s), 8.49 (1H, s).

4) Synthesis of methyl 3-bromo-5-[(4-ethylphenyl)methyl]-2-naphthoate

[Formula 85]

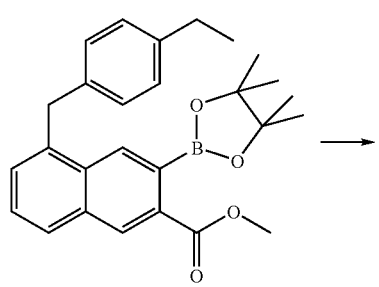

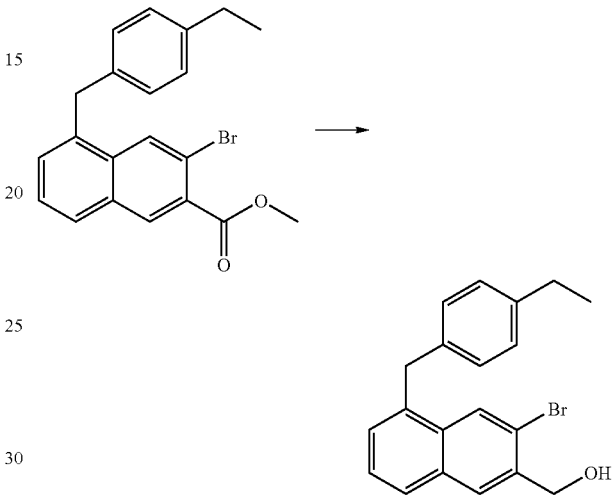

Under a nitrogen stream, methyl 5-[(4-ethylphenyl)methyl]-3-(4,4,5,5-tetramethyl-[1,3,2]dioxaboran-2-yl)-2-naphthoate (594.5 mg, 1.38 mmol) was dissolved in methanol (15.0 mL). To the resultant solution were added cupric bromide (926.1 mg, 4.14 mmol) and water (15.0 mL), and then this mixture was heated to reflux for 18 hours at 90° C. The reaction solution was extracted with ethyl acetate. The organic layer was washed with saturated brine, dried over anhydrous magnesium sulfate and then concentrated under reduced pressure. The resulting residue was purified by silica gel flash column chromatography (developing solution=ethyl acetate:n-hexane (1:10)), to thereby obtain the titled compound (420.6 mg, 79%).

$^1$H-NMR (CDCl$_3$) δ: 1.22 (3H, t, J=7.6 Hz), 2.62 (2H, q, J=7.6 Hz), 3.98 (3H, s), 4.37 (2H, s), 7.09 (2H, d, J=8.3 Hz), 7.13 (2H, d, J=8.3 Hz), 7.37 (1H, d, J=7.6 Hz), 7.48 (1H, dd, J=7.6, 7.6 Hz), 7.77 (1H, d, J=7.6 Hz), 8.33 (1H, s), 8.35 (1H, s).

5) Synthesis of [3-bromo-5-[(4-ethylphenyl)methyl]-naphthalen-2-yl]-methanol

[Formula 86]

Under a nitrogen stream, methyl 3-bromo-5-[(4-ethylphenyl)methyl]-2-naphthoate (334.1 mg, 0.87 mmol) was dissolved in diethyl ether (10.0 mL). To the resultant mixture was added lithium aluminum hydride (39.7 mg, 1.04 mmol) under ice-cooling, and the resultant mixture was stirred for 30 minutes. Water was added thereto, and the resultant mixture was extracted with dichloromethane. The organic layer was washed with saturated brine, dried over anhydrous magnesium sulfate and then concentrated under reduced pressure, to thereby obtain the titled compound (305.8 mg, 89%).

$^1$H-NMR (DMSO) δ: 1.13 (3H, t, J=7.5 Hz), 2.53 (2H, q, J=7.5 Hz), 4.36 (2H, s), 4.62 (2H, d, J=5.4 Hz), 5.55 (1H, t, J=5.4 Hz), 7.09-7.13 (4H, m), 7.39 (1H, d, J=7.6 Hz), 7.50 (1H, dd, J=7.6, 7.6 Hz), 7.85 (1H, d, J=7.6 Hz), 8.02 (1H, s), 8.23 (1H, s).

6) Synthesis of 7-bromo-1-[(4-ethylphenyl)methyl]-6-[(1-methoxy-1-methylethoxy)methyl]-naphthalene

[Formula 87]

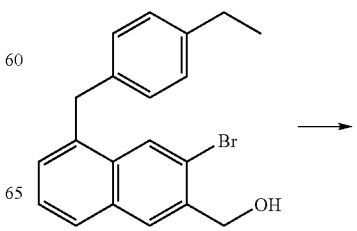

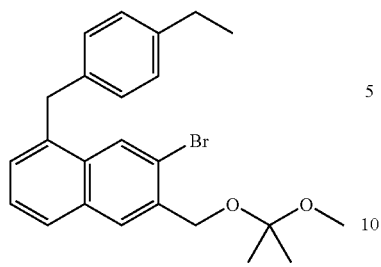

Under a nitrogen stream, to a solution of [3-bromo-5-[(4-ethylphenyl)methyl]-naphthalen-2-yl]-methanol (326.2 mg, 0.92 mmol) and pyridinium p-toluenesulfonate (4.6 mg, 0.02 mmol) in THF (3.0 mL) was added 2-methoxypropene (0.44 mL, 4.6 mmol) under ice-cooling, and the resultant mixture was stirred at the same temperature for 1.5 hours. Saturated aqueous sodium hydrogen carbonate was added thereto. The resultant mixture was extracted with ethyl acetate. The organic layer was dried over anhydrous magnesium sulfate and then concentrated under reduced pressure, to thereby obtain the titled compound (393.2 mg, 100%).

$^1$H-NMR (CDCl$_3$) δ: 1.22 (3H, t, J=7.6 Hz), 2.17 (6H, s), 2.62 (2H, q, J=7.6 Hz), 3.49 (3H, s), 4.36 (2H, s), 4.88 (2H, brs), 7.10-7.12 (4H, m), 7.28 (1H, d, J=8.5 Hz), 7.43 (1H, dd, J=7.6, 8.5 Hz), 7.73 (1H, d, J=7.6 Hz), 7.93 (1H, s), 8.24 (1H, s).

7) Synthesis of (3'R,4'S,5'S,6R,8S)-1-[(4-ethylphenyl)methyl]-6'-hydroxymethyl-3',4',5',6'-tetrahydro-spiro[furo[3,4 g]naphthalen-8(6H),2'-[2H]pyran]-3', 4',5'-triol

[Formula 88]

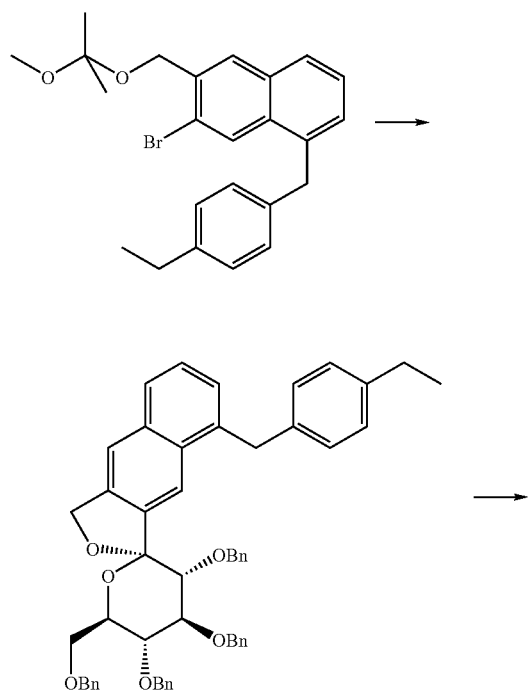

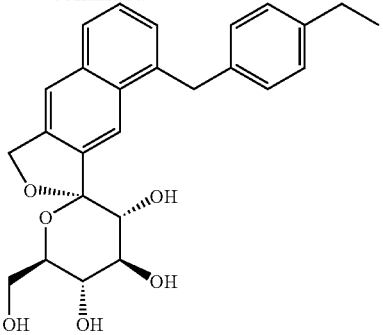

Under a nitrogen stream, to a solution of 7-bromo-1-[(4-ethylphenyl)methyl]-6-[(1-methoxy-1-methylethoxy)methyl]-naphthalene (136.5 mg, 0.32 mmol) in toluene (2.0 mL) was added a solution of s-butyllithium in n-hexane/cyclohexane (0.99 M, 0.39 mL, 0.38 mmol) under ice cooling, and the resultant mixture was stirred for 15 minutes. The reaction solution was added dropwise to a solution of 3,4,5-tris-benzyloxy-6-(benzyloxymethyl)-tetrahydro-pyran-2-one (227.0 mg, 0.42 mmol) in toluene (2.0 mL) that had been cooled to −78° C. The resultant mixture was stirred for 2.5 hours, and then saturated aqueous ammonium chloride was added thereto. The resultant mixture was extracted with ethyl acetate. The organic layer was washed with saturated brine, dried over sodium sulfate, and then concentrated under reduced pressure. To the resulting residue were added THF (3.0 mL), methanol (3.0 mL) and p-toluenesulfonic acid (18.0 mg, 0.10 mmol), and the resultant solution was heated to reflux for 3 hours. Solvent was then removed by distillation under reduced pressure, and the resulting residue was purified by silica gel flash column chromatography (developing solution=ethyl acetate:n-hexane (1:10)), to thereby obtain a crude product (3'R,4'S,5'S,6'R,8S)-3',4',5'-tris-benzyloxy-6-benzyloxymethyl-1-[(4-ethylphenyl)methyl]-3',4',5',6'-tetrahydro-spiro[furo[3,4,g]naphthalen-8(6H),2'-[2H]pyran] (175.6 mg). This crude product (40.6 mg) was then dissolved in dichloromethane (1.0 mL). Pentamethylbenzene (117.6 mg, 0.79 mmol) was added thereto, and then this solution was cooled to −78° C. Boron trichloride (1.0 M dichloromethane solution, 0.25 mL, 0.25 mmol) was added dropwise thereto. The solution was stirred for 3 hours, and then methanol (1.0 mL) was added thereto to stop the reaction. The temperature of the mixture was raised to room temperature, and the reaction mixture was then concentrated under reduced pressure. The resulting residue was purified by silica gel flash column chromatography (developing solution=methanol:dichloromethane (1:10)), to thereby obtain the titled compound (3.3 mg, 15%).

$^1$H-NMR (CD$_3$OD) δ: 1.20 (3H, t, 3=7.6 Hz), 2.60 (2H, q, J=7.6 Hz), 3.51 (1H, dd, J=8.6, 9.9 Hz), 3.61-3.70 (1H, m), 3.77-3.93 (4H, m), 4.44 (2H, s), 5.25 (1H, d, J=13.0 Hz), 5.32 (1H, d, J=13.0 Hz), 7.10 (2H, d, J=8.2 Hz), 7.14 (2H, d, J=8.2 Hz), 7.22 (1H, d, J=6.9 Hz), 7.40 (1H, dd, J=6.9, 8.3 Hz), 7.75-7.77 (2H, m), 8.13 (1H, s).

MS (ESI$^+$): 437 [M+1]$^+$.

HPLC retention time: 18.7 minutes

<HPLC Measurement Conditions>

Column: YMC-Pack ODS-A 6.0×150 mm, 5 μm

Mobile phase: Eluted under gradient from 10 mM AcONH$_4$/MeOH (5%)+10 mM AcONH$_4$/H$_2$O 95%) to 10 mM AcONH$_4$/MeOH (100%) over 20 minutes, and then under the same conditions (10 mM AcONH$_4$/MeOH (100%)) for 5 minutes.

Flow rate: 1.5 mL/min
Column temperature: Room temperature
Detection conditions: Total plot over all wavelengths from 230 to 400 nm Test Example 1

Evaluation of Inhibitory Activity Against Methyl-α-D-Glucopyranoside Uptake of Human Na$^+$-Glucose Cotransporter (SGLT1 and SGLT2)

1) Construction of Human SGLT1 Expression Vector

Human SGLT1 cDNA was amplified by PCR with a cDNA library derived from human small intestine (Clontech) as a template, synthetic DNA primers and KOD+ DNA Polymerase (Toyobo Co., Ltd., Japan). The amplified cDNA was inserted into pcRII-Topo vector by using a Topo TA Cloning Dual Promoter kit (Invitrogen). E. coli competent cells (Invitrogen, TOP10) were transformed with the plasmid vector, cultured in LB medium containing ampicillin (50 mg/L) to grow ampicillin-resistant clones. The plasmid vector containing human SGLT1 cDNA was purified from the clone in a standard manner (see Maniatis et al., Molecular Cloning). Human SGLT1 cDNA added restriction enzyme recognition sites (Eco RI at 5'-end, Hind III at 3'-end) was amplified by PCR with the plasmid vector as a template, synthetic DNA primers containing an additional restriction enzyme recognition site, and KOD+ DNA Polymerase. This amplified cDNA was digested with Eco RI and Hind III and ligated into expression vector pcDNA3.1(−) (Invitrogen) digested with Eco RI and Hind III by a Rapid DNA Ligation kit (Roche Diagonostics). E. coli competent cells (Invitrogen, DH5α) were transformed with the ligated expression vector and grown in ampicillin-containing LB medium. Human SGLT1 expression vector was purified from the ampicillin-resistant clone in a standard manner.

2) Construction of Human SGLT2 Expression Vector

Human SGLT2 cDNA was amplified by PCR with a cDNA library derived from human kidney (Clontech) as a template, synthetic DNA primers and KOD+ DNA Polymerase. The amplified cDNA was inserted into pcRII-Topo vector by using a Topo TA Cloning Dual Promoter kit. E. coli competent cells (TPO10) were transformed with the plasmid vector, cultured in LB medium containing ampicillin (50 mg/L) to grow ampicillin-resistant clones. The plasmid vector containing human SGLT2 cDNA was purified from the clone in a standard manner. Human SGLT2 cDNA added restriction enzyme recognition sites (Xho I at 5'-end, Hind III at 3'-end) was amplified by PCR with the plasmid vector as a template, synthetic DNA primers containing an additional restriction enzyme recognition site and KOD+ DNA Polymerase. This amplified cDNA was digested with Xho I and Hind III, and ligated into expression vector pcDNA3.1(−) digested with Xho I and Hind III by using a Rapid DNA Ligation kit. E. coli competent cells (DH5α) were transformed with the ligated expression vector and grown in ampicillin-containing LB medium. Human SGLT2 expression vector was purified from the ampicillin-resistant clone in a standard manner.

3) Establishment of Cell Lines Stably Expressing Human SGLT1 or Human SGLT2

The human SGLT1 expression vector or the human SGLT2 expression vector was digested with the restriction enzyme Pvu I and transfected into CHO-K1 cells with FuGENE (Roche Diagonostics). After the transfection, the cells were cultured at 37° C. in the presence of 5% $CO_2$ for about 3 weeks in DMEM medium (Gibco) containing penicillin (50 U/mL, SIGMA), streptomycin (50 mg/L, SIGMA), geneticin (200 mg/L, Nacalai Tesque, Inc., Japan) and 20% fetal bovine serum to obtain geneticin-resistant clones. Among these clones, clones stably expressing human SGLT1 or human SGLT2 were selected by the evaluating the sodium-dependent uptake activity of sugar (methyl-α-D-glucopyranoside).

4) Evaluation of Inhibitory Activity Against Methyl-α-D-Glucopyranoside Uptake

Cell lines stably expressing human SGLT1 or human SGLT2 CHO were seeded in 96-well culture plates at a density of 30000 to 40000 cells/well and cultured for 4 to 6 days. The medium in these plates was removed and replaced by 150 μL/well pretreatment buffer (i.e., a buffer containing 140 mM choline chloride, 2 mM potassium chloride, 1 mM calcium chloride, 1 mM magnesium chloride, 10 mM 2-[4-(2-hydroxyethyl)-1-piperazinyl]ethanesulfonic acid and tris(hydroxymethyl)aminomethane, pH 7.4), and the plates were incubated at 37° C. for 20 minutes. The pretreatment buffer in the plates was removed, replaced by 50 μL/well fresh pretreatment buffer, and the plates were incubated at 37° C. for 20 minutes. Methyl-α-D-(U-$^{14}$C)glucopyranoside (6.3 mL, Amersham Pharmacia Biotech, 200 mCi/L) was added to and mixed with 100 mL buffer (i.e., a buffer containing 140 mM sodium chloride, 2 mM potassium chloride, 1 mM calcium chloride, 1 mM magnesium chloride, 1 mM methyl-α-D-glucopyranoside, 10 mM [4-(2-hydroxyethyl)-1-piperazinyl]ethanesulfonic acid and tris(hydroxymethyl)aminomethane, pH 7.4), which was used as uptake buffer. Test compounds were dissolved into uptake buffer and these test compound solutions were used for evaluating inhibitory activity. Uptake buffer without a test compound was used as a control solution. Moreover, for use in measuring baseline uptake in the absence of sodium, sodium-free solution was prepared in the same manner to contain 140 mM choline chloride instead of sodium chloride. The pretreatment buffer was removed from each well of the plates and replaced by 35 μL/well test compound solutions, control solution or sodium-free solution, and the plates were incubated at 37° C. for 45 minutes. The solutions were removed and replaced by 300 μL/well washing buffer (i.e., a buffer containing 140 mM choline chloride, 2 mM potassium chloride, 1 mM calcium chloride, 1 mM magnesium chloride, 10 mM methyl-α-D-glucopyranoside, 10 mM 2-[4-(2-hydroxyethyl)-1-piperazinyl]ethanesulfonic acid and tris(hydroxymethyl)aminomethane, pH 7.4). The washing buffer was removed immediately. This washing procedure was repeated once again, and a cell lysis solution (1 M sodium hydroxide, 0.1% sodium lauryl sulfate) was added in a volume of 30 μL per well to solubilize the cells. 2 M hydrochloric acid (15 μL) was added to the cell lysate in each well, and 40 μL of the resulting solution was transferred to a LumaPlate (Packard). The LumaPlate were left overnight at room temperature to evaporate the solvent. The samples on the plate were measured for their radioactivity with a TopCount NXT(Packard). Assuming that the value obtained by subtracting the baseline uptake level from the uptake level of the control sample was set to 100%, the concentration required for a test compounds to cause 50% inhibition of the uptake level ($IC_{50}$ value) were calculated from the concentration-dependent inhibition curve using ELfit ver. 3. As a result, the compounds of the present invention were found to show a remarkable inhibitory effect on SGLT2. The $IC_{50}$ values for the inhibition of SGLT2 of the representative compounds of the present invention are shown in Table 4.

TABLE 4

| Test Compound | Ic$_{50}$ value (nM) |
|---|---|
| Example 1 | 3.9 |
| Example 2 | 2.0 |
| Example 3 | 5.1 |

Industrial Applicability

According to the present invention, a fused ring spiroketal derivative compound or a prodrug thereof or a pharmaceutically acceptable salt thereof is provided which exhibits excellent SGLT2 inhibitory action. Further, the compound according to the present invention is effective in the prevention or treatment of diabetes, diabetes-related disorders or diabetic complications.

The invention claimed is:

1. A compound represented by Formula (I):

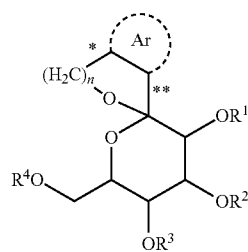

(I)

wherein $R^1$, $R^2$, $R^3$, and $R^4$ are each independently selected from a hydrogen atom, a $C_{1-6}$ alkyl group which may be substituted with one or more Ra, a $C_{7-14}$ aralkyl group which may be substituted with one or more Rb and —C(=O)Rx;

Rx is a $C_{1-6}$ alkyl group which may be substituted with one or more Ra, a aryl group which may be substituted with one or more Rb, a heteroaryl group which may be substituted with one or more Rb or a $C_{1-6}$ alkoxy group which may be substituted with one or more Ra;

n is an integer selected from 1 and 2;

Ra is each independently selected from a halogen atom, a hydroxyl group, a cyano group, a nitro group, a carboxy group, a $C_{1-6}$ alkoxy group which may be substituted with one or more Rc, an aryl group which may be substituted with one or more Rd, an aryloxy group which may be substituted with one or more Rd, a heteroaryl group which may be substituted with one or more Rd, a heteroaryloxy group which may be substituted with one or more Rd, a mercapto group, a $C_{1-6}$ alkylthio group which may be substituted with one or more Rc, a $C_{1-6}$ alkylsulfinyl group which may be substituted with one or more Rc, a $C_{1-6}$ alkylsulfonyl group which may be substituted with one or more Rc, a $C_{1-6}$ alkoxycarbonyl group which may be substituted with one or more Rc and a $C_{1-6}$ alkylcarbonyl group which may be substituted with one or more Rc;

Rb is each independently selected from a $C_{1-6}$ alkyl group which may be substituted with one or more Rc, a $C_{3-8}$ cycloalkyl group which may be substituted with one or more Rc, a $C_{2-6}$ alkenyl group which may be substituted with one or more Rc, a $C_{2-6}$ alkynyl group which may be substituted with one or more Rc, a $C_{7-14}$ aralkyl group which may be substituted with one or more Rd, a halogen atom, a hydroxyl group, a cyano group, a nitro group, a carboxy group, a $C_{1-6}$ alkoxy group which may be substituted with one or more Rc, an aryl group which may be substituted with one or more Rd, an aryloxy group which may be substituted with one or more Rd, a heteroaryl group which may be substituted with one or more Rd, a heteroaryloxy group which may be substituted with one or more Rd, a mercapto group, a $C_{1-6}$ alkylthio group which may be substituted with one or more Rc, a $C_{1-6}$ alkylsulfinyl group which may be substituted with one or more Rc, a $C_{1-6}$ alkylsulfonyl group which may be substituted with one or more Rc, a $C_{1-6}$ alkylcarbonyl group which may be substituted with one or more Rc, a $C_{1-6}$ alkoxycarbonyl group which may be substituted with one or more Rc, a $C_{1-3}$ alkylenedioxy group, a heterocyclyl group and a heterocyclyloxy group;

Rc is each independently selected from a halogen atom, a hydroxyl group, a cyano group, a nitro group, a carboxy group, a $C_{1-6}$ alkoxy group, an aryl group which may be substituted with one or more Rd, an aryloxy group which may be substituted with one or more Rd, a heteroaryl group which may be substituted with one or more Rd, a heteroaryloxy group which may be substituted with one or more Rd, an amino group, a $C_{1-6}$ alkylamino group and a di($C_{1-6}$ alkyl)amino group;

Rd is each independently selected from a $C_{1-6}$ alkyl group which may be substituted with one or more halogen atoms, a $C_{7-14}$ aralkyl group, a halogen atom, a hydroxyl group, a cyano group, a nitro group, an amino group, a $C_{1-6}$ alkylamino group and a di($C_{1-6}$ alkyl)amino group;

ring Ar is selected from the groups represented by the following Formula (a) to (f),

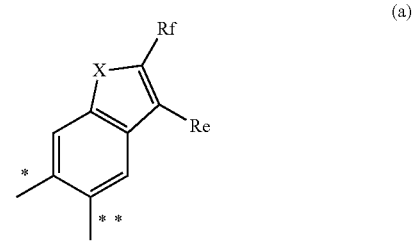

(a)

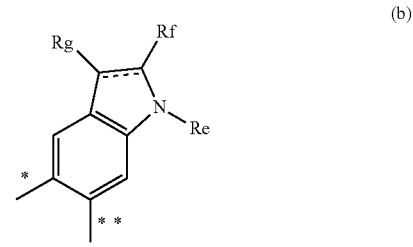

(b)

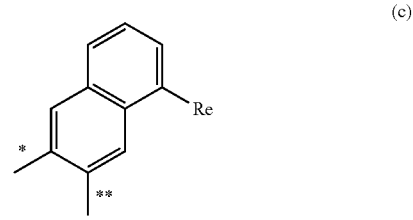

(c)

(d)
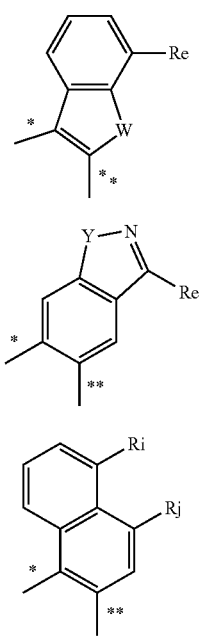

(e)

(f)

wherein X is N—Rh, O or S;
Re is a $C_{7-14}$ aralkyl group which may be substituted with one or more Rb or a $C_{5-12}$ heteroarylalkyl group which may be substituted with one or more Rb;
Rf and Rg are each independently selected from a hydrogen atom, a halogen atom and a $C_{1-6}$ alkyl group;
W is S, O or N—Rh;
Y is N—Rh, O or S;
Rh is a hydrogen atom or a $C_{1-6}$ alkyl group;
Ri and Rj are a hydrogen atom, a $C_{7-14}$ aralkyl group which may be substituted with one or more Rb or a $C_{5-12}$ heteroarylalkyl group which may be substituted with one or more Rb;
provided that, one of Ri or Rj must be a hydrogen atom;
except where both Ri and Rj are a hydrogen atom; and $\overline{------}$ represents a single bond or a double bond, and * and ** respectively represent a bonding site,
or a pharmaceutically acceptable salt thereof.

2. The compound according to claim 1, wherein the ring Ar is represented by the following Formula (g) to (i), (g)

(h)
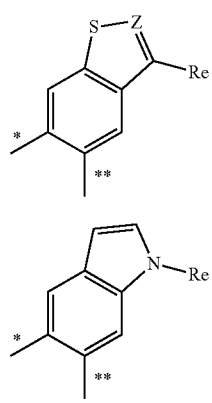

(i)
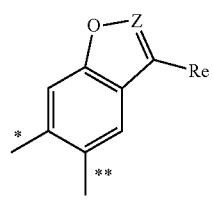

wherein Z is CH or N; and
Re is a $C_{7-14}$ aralkyl group which may be substituted with one or more Rb or a $C_{5-12}$ heteroarylalkyl group which may be substituted with one or more Rb,
or a pharmaceutically acceptable salt thereof.

3. The compound according to claim 1, wherein $R^1$, $R^2$, $R^3$, and $R^4$ are each independently selected from a hydrogen atom and —C(=O)Rx, and Rx is a $C_{1-6}$ alkyl group which may be substituted with one or more Ra or a $C_{1-6}$ alkoxy group which may be substituted with one or more Ra, or a pharmaceutically acceptable salt thereof.

4. The compound according to claim 3, wherein $R^1$, $R^2$, $R^3$, and $R^4$ are a hydrogen atom, or a pharmaceutically acceptable salt thereof.

5. The compound according to claim 1, wherein n is 1, or a pharmaceutically acceptable salt thereof.

6. The compound according to claim 1, wherein n is 2, or a pharmaceutically acceptable salt thereof.

7. A compound selected from the group consisting of:
(3'R,4'S,5S,5'S,6'R)-3-[(4-ethylphenyl)methyl]-6'-hydroxymethyl-3',4',5',6'-tetrahydro-spiro[thieno[2,3,f]isobenzofuran-5(7H),2'-[2H]pyran]-3',4',5'-triol;
(3'R,4'S,5'S,6'R,7S)-1-[(4-ethylphenyl)methyl]-6'-hydroxymethyl-3',4',5',6'-tetrahydro-spiro[furo[3,4,f]indole-7(5H),2'-[2H]pyran]-3',4',5'-triol;
(1S,3'R,4'S,5'S,6'R)-8-[(4-ethylphenyl)methyl]-3,3',4,4',5',6'-hexahydro-6'-hydroxymethyl-spiro[2-oxa-9-thia-fluorene-1,2'-[2H]pyran]-3',4',5'-triol;
(3'R,4'S,5S,5'S,6'R)-6'-hydroxymethyl-3',4',5',6'-tetrahydro-3-[(4-trifluoromethylphenyl)methyl]-spiro[thieno[2,3,f]isobenzofuran-5(7H),2'-[2H]pyran]-3',4',5'-triol;
(3'R,4'S,5S,5'S,6'R)-6'-hydroxymethyl-3',4',5',6'-tetrahydro-3-[(4-trifluoromethoxyphenyl)methyl]-spiro[thieno[2,3,f]isobenzofuran-5(7H),2'-[2H]pyran]-3',4',5'-triol;
(3'R,4'S,5S,5'S,6'R)-3-[(4-fluorophenyl)methyl]-6'-hydroxymethyl-3',4',5',6'-tetrahydro-spiro[thieno[2,3,f]isobenzofuran-5(7H),2'-[2H]pyran]-3',4',5'-triol;
(3'R,4'S,5S,5'S,6'R)-3-[(4-cyclopropylphenyl)methyl]-6'-hydroxymethyl-3',4',5',6'-tetrahydro-spiro[thieno[2,3,f]isobenzofuran-5(7H),2'-[2H]pyran]-3',4',5'-triol;
(3'R,4'S,5S,5'S,6'R)-6'-hydroxymethyl-3-[(4-methylphenyl)methyl]-3',4',5',6'-tetrahydro-spiro[thieno[2,3,f]isobenzofuran-5(7H),2'-[2H]pyran]-3',4',5'-triol;
(3'R,4'S,5S,5'S,6'R)-6'-hydroxymethyl-3-[(4-isopropylphenyl)methyl]-3',4',5',6'-tetrahydro-spiro[thieno[2,3,f]isobenzofuran-5(7H),2'-[2H]pyran]-3',4',5'-triol;
(3'R,4'S,5S,5'S,6'R)-3-[(5-ethylthiophen-2-yl)methyl]-6'-hydroxymethyl-3',4',5',6'-tetrahydro-spiro[thieno[2,3,f]isobenzofuran-5(7H),2'-[2H]pyran]-3',4',5'-triol;
(3'R,4'S,5S,5'S,6'R)-3-[(benzothiophen-2-yl)methyl]-6'-hydroxymethyl-3',4',5',6'-tetrahydro-spiro[thieno[2,3,f]isobenzofuran-5(7H),2'-[2H]pyran]-3',4',5'-triol;
(3'R,4'S,5S,5'S,6'R)-3-[(4-ethylphenyl)methyl]-6'-hydroxymethyl-2-methyl-3',4',5',6'-tetrahydro-spiro[thieno[2,3,f]isobenzofuran-5(7H),2'-[2H]pyran]-3',4',5'-triol;

(3'R,4'S,5S,5'S,6'R)-2-chloro-3-[(4-ethylphenyl)methyl]-6'-hydroxymethyl-3',4',5',6'-tetrahydro-spiro[thieno[2,3,f]isobenzofuran-5(7H),2'-[2H]pyran]-3',4',5'-triol;

(3'R,4'S,5S,5'S,6'R)-3-(4-ethylphenyl)-6'-hydroxymethyl-3',4',5',6'-tetrahydro-spiro[thieno[2,3,f]isobenzofuran-5(7H),2'-[2H]pyran]-3',4',5'-triol;

(3'R,4'S,5'S,6'R,7S)-6'-hydroxymethyl-3',4',5',6'-tetrahydro-1-[(4-trifluoromethoxyphenyl)methyl]-spiro[furo[3,4,f]indole-7(5H),2'-[2H]pyran]-3',4',5'-triol;

(3'R,4'S,5'S,6'R,7S)-1-[(4-fluorophenyl)methyl]-6'-hydroxymethyl-3',4',5',6'-tetrahydro-spiro[furo[3,4,f]indole-7(5H),2'-[2H]pyran]-3',4',5'-triol;

(3'R,4'S,5'S,6'R,7S)-6'-hydroxymethyl-3',4',5',6'-tetrahydro-1-[(4-trifluoromethylphenyl)methyl]-spiro[furo[3,4,f]indole-7(5H),2'-[2H]pyran]-3',4',5'-triol;

(3'R,4'S,5'S,6'R,7S)-6'-hydroxymethyl-1-[(4-methylphenyl)methyl]-3',4',5',6'-tetrahydro-spiro[furo[3,4,f]indole-7(5H),2'-[2H]pyran]-3',4',5'-triol;

(3'R,4'S,5'S,6'R,7S)-1-[(4-cyclopropylphenyl)methyl]-6'-hydroxymethyl-3',4',5',6'-tetrahydro-spiro[furo[3,4,f]indole-7(5H),2'-[2H]pyran]-3',4',5'-triol;

(3'R,4'S,5'S,6'R,7S)-6'-hydroxymethyl-1-[(4-n-propylphenyl)methyl]-3',4',5',6'-tetrahydro-spiro[furo[3,4,f]indole-7(5H),2'-[2H]pyran]-3',4',5'-triol;

(3'R,4'S,5'S,6'R,7S)-1-[(5-ethylthiophen-2-yl)methyl]-6'-hydroxymethyl-3',4',5',6'-tetrahydro-spiro[furo[3,4,f]indole-7(5H),2'-[2H]pyran]-3',4',5'-triol;

(3'R,4'S,5'S,6'R,7S)-6'-hydroxymethyl-1-[(4-isopropylphenyl)methyl]-3',4',5',6'-tetrahydro-spiro[furo[3,4,f]indole-7(5H),2'-[2H]pyran]-3',4',5'-triol;

(3'R,4'S,5'S,6'R,7S)-1-[(5-fluorobenzothiophen-2-yl)methyl]-6'-hydroxymethyl-3',4',5',6'-tetrahydro-spiro[furo[3,4,f]indole-7(5H),2'-[2H]pyran]-3',4',5'-triol;

(3'R,4'S,5'S,6'R,7S)-1-[(benzothiophen-2-yl)methyl]-6'-hydroxymethyl-3',4',5',6'-tetrahydro-spiro[furo[3,4,f]indole-7(5H),2'-[2H]pyran]-3',4',5'-triol;

(3'R,4'S,5'S,6'R,7S)-1-[2-(4-ethylphenyl)ethyl]-6'-hydroxymethyl-3',4',5',6'-tetrahydro-spiro[furo[3,4,f]indole-7(5H),2'-[2H]pyran]-3',4',5'-triol;

(3'R,4'S,5'S,6'R,7S)-3-chloro-1-[(4-ethylphenyl)methyl]-6'-hydroxymethyl-3',4',5',6'-tetrahydro-spiro[furo[3,4,f]indole-7(5H),2'-[2H]pyran]-3',4',5'-triol;

(1S,3'R,4'S,5'S,6'R)-3,3',4,4',5',6'-hexahydro-6'-hydroxymethyl-8-[(4-isopropylphenyl)methyl]-spiro[2-oxa-9-thia-fluorene-1,2'-[2H]pyran]-3',4',5'-triol;

(1S,3'R,4'S,5'S,6'R)-3,3',4,4',5',6'-hexahydro-6'-hydroxymethyl-8-[(4-methylphenyl)methyl]-spiro[2-oxa-9-thia-fluorene-1,2'-[2H]pyran]-3',4',5'-triol;

(3'R,4'S,5S,5'S,6'R)-3-[(4-ethylphenyl)methyl]-6'-hydroxymethyl-3',4',5',6'-tetrahydro-spiro[furo[3,4,f]indazole-5(1H,7H),2'-[2H]pyran]-3',4',5'-triol;

(3'R,4'S,5S,5'S,6'R)-3-[(4-ethylphenyl)methyl]-6'-hydroxymethyl-3',4',5',6'-tetrahydro-spiro[furo[3,4,f]benzoisoxazole-5(7H),2'-[2H]pyran]-3',4',5'-triol;

(3'R,4'S,5S,5'S,6'R)-3-[(4-ethylphenyl)methyl]-6'-hydroxymethyl-3',4',5',6'-tetrahydro-spiro[furo[3,4,f]benzoisothiazole-5(7H),2'-[2H]pyran]-3',4',5'-triol;

(3S,3'R,4'S,5'S,6'R)-5-[(4-ethylphenyl)methyl]-6'-hydroxymethyl-3',4',5',6'-tetrahydro-spiro[benz[g]isobenzofuro-3(1H),2'-[2H]pyran]-3',4',5'-triol; and (3'R,4'S,5'S,6'R,8S)-1-[(4-ethylphenyl)methyl]-6'-hydroxymethyl-3',4',5',6'-tetrahydro-spiro[furo[3,4,g]naphthalene-8(6H),2'-[2H]pyran]-3',4',5'-triol;

or a pharmaceutically acceptable salt thereof.

8. A compound represented by Formula (Ia):

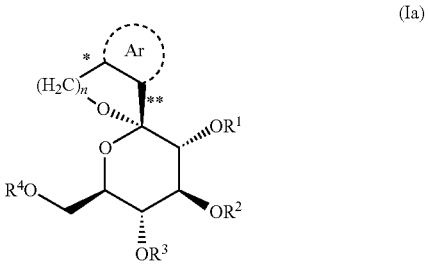

(Ia)

wherein $R^1$, $R^2$, $R^3$, and $R^4$ are each independently selected from a hydrogen atom, a $C_{1-6}$ alkyl group which may be substituted with one or more Ra, a $C_{7-14}$ aralkyl group which may be substituted with one or more Rb and —C(=O)Rx;

Rx is a $C_{1-6}$ alkyl group which may be substituted with one or more Ra, a aryl group which may be substituted with one or more Rb, a heteroaryl group which may be substituted with one or more Rb or a $C_{1-6}$ alkoxy group which may be substituted with one or more Ra;

n is an integer selected from 1 and 2;

Ra is each independently selected from a halogen atom, a hydroxyl group, a cyano group, a nitro group, a carboxy group, a $C_{1-6}$ alkoxy group which may be substituted with one or more Rc, an aryl group which may be substituted with one or more Rd, an aryloxy group which may be substituted with one or more Rd, a heteroaryl group which may be substituted with one or more Rd, a heteroaryloxy group which may be substituted with one or more Rd, a mercapto group, a $C_{1-6}$ alkylthio group which may be substituted with one or more Rc, a $C_{1-6}$ alkylsulfinyl group which may be substituted with one or more Rc, a $C_{1-6}$ alkylsulfonyl group which may be substituted with one or more Rc, a $C_{1-6}$ alkoxycarbonyl group which may be substituted with one or more Rc and a $C_{1-6}$ alkylcarbonyl group which may be substituted with one or more Rc;

Rb is each independently selected from a $C_{1-6}$ alkyl group which may be substituted with one or more Rc, a $C_{3-8}$ cycloalkyl group which may be substituted with one or more Rc, a $C_{2-6}$ alkenyl group which may be substituted with one or more Rc, a $C_{2-6}$ alkynyl group which may be substituted with one or more Rc, a $C_{7-14}$ aralkyl group which may be substituted with one or more Rd, a halogen atom, a hydroxyl group, a cyano group, a nitro group, a carboxy group, a $C_{1-6}$ alkoxy group which may be substituted with one or more Rc, an aryl group which may be substituted with one or more Rd, an aryloxy group which may be substituted with one or more Rd, a heteroaryl group which may be substituted with one or more Rd, a heteroaryloxy group which may be substituted with one or more Rd, a mercapto group, a $C_{1-6}$ alkylthio group which may be substituted with one or more Rc, a $C_{1-6}$ alkylsulfinyl group which may be substituted with one or more Rc, a $C_{1-6}$ alkylsulfonyl group which may be substituted with one or more Rc, a $C_{1-6}$ alkylcarbonyl group which may be substituted with one or more Rc and a $C_{1-6}$ alkoxycarbonyl group which may be substituted with one or more Rc, a $C_{1-3}$ alkylenedioxy group, a heterocyclyl group and a heterocyclyloxy group;

Rc is each independently selected from a halogen atom, a hydroxyl group, a cyano group, a nitro group, a carboxy group, a $C_{1-6}$ alkoxy group, an aryl group which may be substituted with one or more Rd, an aryloxy group which may be substituted with one or more Rd, a heteroaryl group which may be substituted with one or more Rd, a heteroaryloxy group which may be substituted with one or more Rd, an amino group, a $C_{1-6}$ alkylamino group and a di ($C_{1-6}$ alkyl)amino group;

Rd is each independently selected from a $C_{1-6}$ alkyl group which may be substituted with one or more halogen atoms, a $C_{7-14}$ aralkyl group, a halogen atom, a hydroxyl group, a cyano group, a nitro group, an amino group, a $C_{1-6}$ alkylamino group and a di ($C_{1-6}$ alkyl)amino group;

ring Ar is selected from the groups represented by the following Formula (a) to (f):

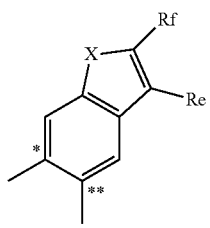

(a)

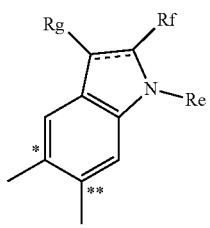

(b)

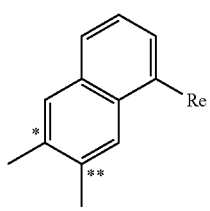

(c)

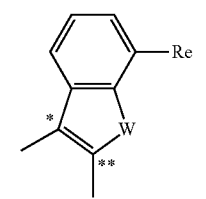

(d)

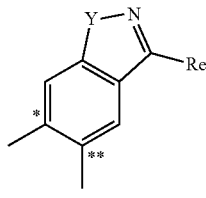

(e)

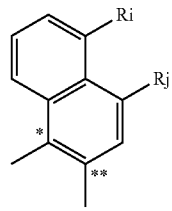

(f)

wherein X is N—Rh, O or S;

Re is a $C_{7-14}$ aralkyl group which may be substituted with one or more Rb or a $C_{5-12}$ heteroarylalkyl group which may be substituted with one or more Rb;

Rf and Rg are each independently selected from a hydrogen atom, a halogen atom and a $C_{1-6}$ alkyl group;

W is N—Rh, O or S;

Y is N—Rh, O or S;

Rh is a hydrogen atom or a $C_{1-6}$ alkyl group;

Ri and Rj are a hydrogen atom, a $C_{7-14}$ aralkyl group which may be substituted with one or more Rb or a $C_{5-12}$ heteroarylalkyl group which may be substituted with one or more Rb;

provided that, one of Ri or Rj must be a hydrogen atom; except where both Ri and Rj are a hydrogen atom; and ------- represents a single bond or a double bond, and * and ** respectively represent a bonding site, or a pharmaceutically acceptable salt thereof.

9. A pharmaceutical composition comprising a compound, or a pharmaceutically acceptable salt thereof, according to claim 1.

10. A method of inhibiting an Na$^+$-glucose cotransporter which comprises contacting an Na$^+$-glucose cotransporter, in vitro or in vivo, with an inhibitory amount of a compound, or a pharmaceutically acceptable salt thereof, according to claim 1.

11. A method of treating diabetes, hyperglycemia, diabetic complications or obesity which comprises administering to a subject in need thereof a therapeutically effective amount of a pharmaceutical composition according to claim 9.

12. The method according to claim 11, wherein the diabetes is insulin-dependent diabetes (Type 1 diabetes) or non-insulin-dependent diabetes (Type 2 diabetes).

13. A pharmaceutical composition comprising a compound, or a pharmaceutically acceptable salt thereof, according to claim 8.

14. A method of inhibiting an Na$^+$-glucose cotransporter which comprises contacting an Na$^+$-glucose cotransporter, in vitro or in vivo, with an inhibitory amount of a compound, or a pharmaceutically acceptable salt thereof, according to claim 8.

15. A method of treating diabetes, hyperglycemia, diabetic complications or obesity which comprises administering to a subject in need thereof a therapeutically effective amount of a pharmaceutical composition according to claim 13.

16. The method according to claim 15, wherein the diabetes is insulin-dependent diabetes (Type 1 diabetes) or non-insulin-dependent diabetes (Type 2 diabetes).

* * * * *